US011236318B2

(12) United States Patent
Mizumura et al.

(10) Patent No.: US 11,236,318 B2
(45) Date of Patent: *Feb. 1, 2022

(54) RECOMBINANT FACTOR C AND METHOD FOR PRODUCING THE SAME, AND METHOD FOR MEASURING ENDOTOXIN

(71) Applicant: SEIKAGAKU CORPORATION, Tokyo (JP)

(72) Inventors: Hikaru Mizumura, Tokyo (JP); Toshio Oda, Tokyo (JP); Shun-ichiro Kawabata, Fukuoka (JP)

(73) Assignee: SEIKAGAKU CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/399,386

(22) Filed: Apr. 30, 2019

(65) Prior Publication Data
US 2019/0270977 A1  Sep. 5, 2019

Related U.S. Application Data

(63) Continuation of application No. 15/983,725, filed on May 18, 2018, now Pat. No. 10,982,202, which is a continuation of application No. 14/650,767, filed as application No. PCT/JP2013/083082 on Dec. 10, 2013, now Pat. No. 10,144,923.

(30) Foreign Application Priority Data

Dec. 10, 2012  (JP) ................................. 2012-269840

(51) Int. Cl.
*C12N 9/64* (2006.01)
*G01N 33/569* (2006.01)
*C12Q 1/37* (2006.01)
*C12N 15/85* (2006.01)
*G01N 33/579* (2006.01)

(52) U.S. Cl.
CPC .... *C12N 9/6408* (2013.01); *C12Y 304/21069* (2013.01); *C12Y 304/21084* (2013.01); *G01N 33/56911* (2013.01); *G01N 33/579* (2013.01); *G01N 2333/96411* (2013.01)

(58) Field of Classification Search
None
See application file for complete search history.

(56) References Cited

U.S. PATENT DOCUMENTS

| 5,712,144 | A | 1/1998 | Ding et al. |
| 5,716,834 | A | 2/1998 | Ding et al. |
| 5,795,962 | A | 8/1998 | Iwanaga et al. |
| 5,840,510 | A | 11/1998 | Tanaka et al. |
| 5,858,706 | A | 1/1999 | Ding et al. |
| 6,077,946 | A | 1/2000 | Iwanaga et al. |
| 6,645,724 | B1 | 11/2003 | Ding et al. |
| 10,144,923 | B2 * | 12/2018 | Mizumura .......... C12N 9/6408 |
| 2002/0068325 | A1 * | 6/2002 | Ng ................. C12Y 302/01096 435/69.1 |
| 2003/0054432 | A1 | 3/2003 | Chen et al. |
| 2004/0235080 | A1 | 11/2004 | Chen et al. |
| 2008/0131929 | A1 | 6/2008 | Prentice et al. |
| 2009/0208995 | A1 | 8/2009 | Tamura et al. |
| 2010/0086967 | A1 | 4/2010 | Kaufmann et al. |
| 2013/0295613 | A1 | 11/2013 | Kishishita et al. |
| 2014/0024062 | A1 | 1/2014 | Mizumura et al. |
| 2014/0249082 | A1 | 9/2014 | Cottingham et al. |

FOREIGN PATENT DOCUMENTS

| JP | 2005-500520 A | 1/2005 |
| JP | 2006-87435 A | 4/2006 |
| JP | 2008-520250 A | 6/2008 |
| JP | 2008520250 A | 6/2008 |
| JP | 2010-516264 A | 5/2010 |
| JP | 2010516264 A | 5/2010 |
| SG | 94673 A1 | 3/2003 |
| WO | 9915676 A1 | 4/1999 |
| WO | 2008/004674 A1 | 1/2008 |
| WO | 2012091124 A1 | 7/2012 |
| WO | 2012/118226 A1 | 9/2012 |

OTHER PUBLICATIONS

Bram Blomme et al., "Alteration of protein glycosylation in liver diseases", Journal of Hepatology, 2009, vol. 50, pp. 592-603 (12 pages total).
Office Action dated Feb. 12, 2020 issued in U.S. Appl. No. 15/983,725.
Stephanie Holst et al., "Profiling of different pancreatic cancer cells used as models for metastatic behaviour shows large variation in their N-glycosylation" Scientific Reports, Nov. 30, 2017, vol. 7, No. 16623, pp. 1-15 (15 pages total).
Communication dated Apr. 19, 2017, from the State Intellectual Property Office of the P.R.C., in counterpart Chinese application No. 201380064649.3.
Communication dated Aug. 7, 2018 issued by the Japanese Patent Office in counterpart application No. 2014-552048.
Communication dated Aug. 7, 2018, from the Japanese Patent Office in counterpart application No. 2014-552048.
Communication dated Jul. 29, 2016 from the State Intellectual Property Office of the P.R.C. in counterpart application No. 201380064649.3.
Communication dated Jul. 5, 2016, from the European Patent Office in counterpart European Application No. 13862466.3.

(Continued)

*Primary Examiner* — David Steadman
(74) *Attorney, Agent, or Firm* — Sughrue Mion, PLLC

(57) ABSTRACT

A horseshoe crab Factor C protein having activity of Factor C, wherein the horseshoe crab is selected from *Tachypleus tridentatus*, *Limulus polyphemus*, and *Carcinoscorpius rotundicauda*, and wherein the horseshoe crab Factor C protein is produced through being recombinantly expressed from a Chinese Hamster Ovary (CHO) DG44 cell or HEK cell.

21 Claims, 10 Drawing Sheets

Specification includes a Sequence Listing.

(56) References Cited

OTHER PUBLICATIONS

Extended European Search Report dated Jan. 10, 2019 issued by the European Patent Office in counterpart application No. 18190686.8.
International Search Report for PCT/JP2013/083082 dated Feb. 10, 2012.
Jeak L. Ding et al., "A new era in pyrogen testing", TRENDS in Biotechnology, Aug. 2001, pp. 277-281, vol. 19, No. 8.
Jeak Ling Ding et al., "Chapter 9, Endotoxin Detection—from Limulus Amebocyte Lysate to Recombinant Factor C", Endotoxins: Structure, Function and Recognition Series : Subcellular Biochemistry in: Subcellular Biochemistry: Reviews and Essays Dealing With the Function, Genetics, Biogenesis and Evolution of Sub-Cellular Components, vol. 53, Jan. 1, 2010, XP009510157, 22 pages total.
Jing Wang et al., "Functional expression of full length Limulus Factor C in stably transformed Sf9 cells", Biotechnology Letters, 2001, pp. 71-76, vol. 23.
Jing Wang et al., "Modular Arrangement and Secretion of a Multidomain Serine Protease", The Journal of Biological Chemistry, Sep. 27, 2002, pp. 36363-36372, vol. 277, No. 39.
Mizumura, et al., Genetic engineering approach to develop next-generation reagents for endotoxin quantification; Innate Immunity, vol. 23, No. 2, pp. 136-146, 2017.
Nakamura T. et al. "Lipopolysaccharide-sensitive serine-protease zymogen (factor C) found in Limulus hemocytes" European Journal of Biochemistry vol. 154, 1986; pp. 511-521.
Office Action issued in the corresponding European Application No. 13862466.3 dated Nov. 30, 2017.
Roopashree S. Dwarakanath et al., "Recombinant COS-1 cells espress Carcinoscorpius rotundicauda Factor C", Biotechnology Letters, Apr. 1997, pp. 357-361, vol. 19, No. 4.
Sadaaki Iwanaga, "The limulus clotting reaction", Current Opinion in Immunology 1993, pp. 74-82, vol. 5.
Shengwu Wuli Jinzhan vol. 31, No. 8, p. 736-740, 2004.
Takanori Nakamura et al., "Purification and Properties of Intracellular Clotting Factor, Factor B, from Horseshoe Crab (*Tachypleus tridentatus*) Hemocytes", J. Biochem, 1986, vol. 99, No. 3.
Tokunaga F. et al. "Lipopolysaccharide-sensitive serine-protease zymogen factor C of horseshoe crab hemocytes identification and alignment of proteolytic fragments produced during the activation show that it is a novel type of serine protease" European Journal of Biochemistry vol. 167 No. 3, 1987; pp. 405-416.
Xiangjun et al., "Role of domains in factor C from Tachypleus tridentatus in neutralization endotoxin", "Accession:2006:239467" File CAPLUS, 2003.
Xiangjun et al., "Role of domains in factor C from Tachypleus tridentatus in neutralization endotoxin", "Accession:2006:239467" File CAPLUS [online],Retrived from the STN on the Web, [retrieved on Jan. 29, 2014], Shengwu Huaxue Yu Shengwu Wuli Jinzhan vol. 31, No. 8, p. 736-740, 2004.
Office Action dated Apr. 27, 2020 issued by the USPTO in U.S. Appl. No. 16/399,575.
Office Action dated May 21, 2020 issued by the USPTO in U.S. Appl. No. 15/983,725.
Strategies for Protein Purification Handbook, GE Healthcare, Sep. 2010, 167 pages.
Koshiba et al., "A Structural Perspective on the Interaction between Lipopolysaccharide and Factor C, a Receptor Involved in Recognition of Gram-negative Bacteria", J. Biol. Chem., 282, 3962-3967, 2007 (13 pages in total).
Current Protocols in Molecular Biology (1993) 16.23.1-16.23.13, John Wiley and Sons, Inc., 2002.
Slade et al., "Identifying the CHO Secretome using Mucin-type O-Linked Glycosylation and Click-chemistry", J. Prot. Res., 11,:6175-6186, 2012.
International Preliminary Report on Patentability in International Application No. PCT/JP2013/083082 dated Jun. 16, 2015 and dated Jun. 25, 2015.
Written Opinion for PCT/JP2013/083082 dated Feb. 10, 2014.
International Search Report for PCT/JP2013/083082 dated Feb. 10, 2014.
Final Office Action dated Aug. 4, 2020 issued in U.S. Appl. No. 16/399,575.
Damasceno et al., "Protein secretion in *Pichia pastoris* and advances in protein production", Appl Microbiol Biotechnol (2012) 93: pp. 31-39, Published online: Nov. 2011.
Final Office Action dated Aug. 28, 2020 issued in U.S. Appl. No. 15/983,725.
Knappskog et al., "The level of synthesis and secretion of *Ganssia princeps* luciferase in transfected CHO cells is heavily dependent on the choice of signal peptide", Journal of Biotechnology, vol. 128, 2007, pp. 705-715.
Communication of Notice of Opposition dated Nov. 11, 2020, issued by the European Patent Office in EP Application No. 18190686.8.
A certified translation of the priority document JP 2012269840 filed Dec. 10, 2012.
Carlesso, E. et al., "The rule regulating pH changes during crystalloid infusion", Intensive Care Med., 2011, 37(3): 461-468.
The Wikipedia site relating to "Blood Plasma" as of Nov. 19, 2012, provided by the WayBack Machine.
The Wikipedia site relating to "Horseshoe Crab" as of Nov. 23, 2011, provided by the WayBack Machine.
Harada-Suzuki, T. et al., "Further Studies on the Chromogenic Substrate Assay Method for Bacterial Endotoxins Using Horseshoe Crab (*Tachypleus tridentatus*) Hemocyte Lysate", J. Biochem., 1982, 92(3):793-800.
Tomiya, N. et al., "Comparing N-glycan processing in mammalian cell lines to native and engineered Tepidopteran insect cell lines", Glycoconjugate Journal, 2004, 21:343-360.
Nettleship, Joanne E., "Structural Biology of Glycoproteins", Glycosylation, 2012, p. 41-62. Available from: https://www.intechopen.com/books/glycosylation/structural- biologyof- glycoproteins.
Thomas, P. and Smart, T.G., "HEK293 cell line: A vehicle for the expression of recombinant proteins", J. Pharmacol. And Toxicol. Methods, 2005, 51: 187-200.
Declaration by Dr. Hikaru Mizumura submitted to the USPTO, signed Oct. 11, 2017 in U.S. Appl. No. 14/650,767.
Excerpt from Essential Cell Biology (2nd Edition), Alberts et al., Taylor and Francis Group, New York and London, 2004 (p. 209).
Hossler, P. et al., "Optimal and consistent protein glycosylation in mammalian cell culture", Gycobiol. 19(9): 936-949, 2009.
Declaration by Dr. Hikaru Mizumura submitted to the USPTO, signed Feb. 22, 2018 in U.S. Appl. No. 14/650,767.
Inhibition data performed using a Limulus Factor C expressed in HEK 293 cells and HEK 293 GnTl-cells filed with Opposition against EP3441466B dated Nov. 5, 2020.

* cited by examiner

[Fig. 1]
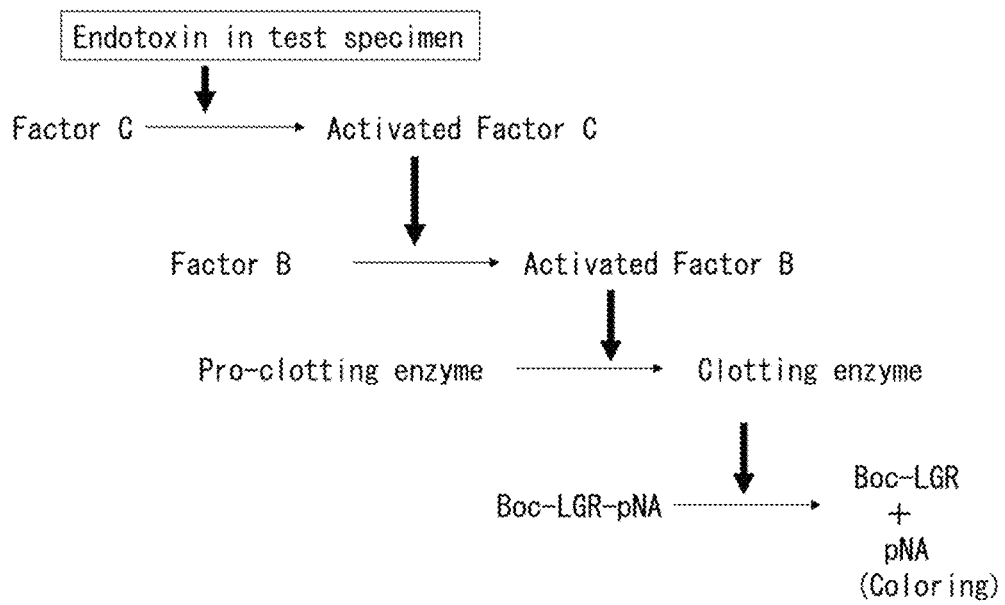
[Fig. 2]
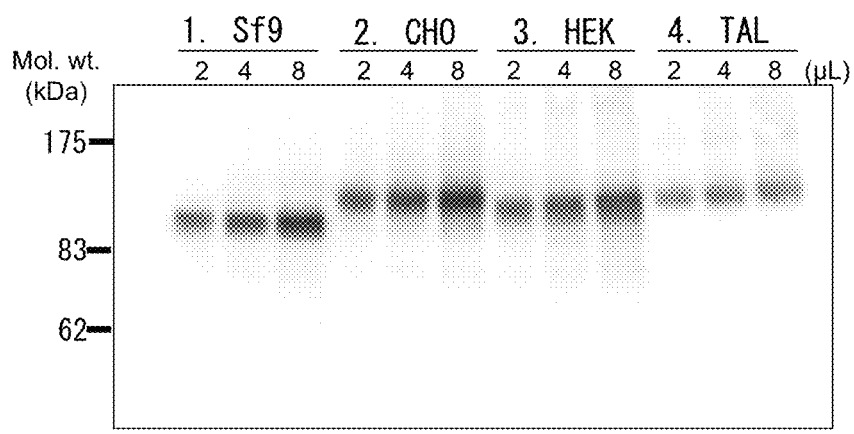
Primary antibody: Anti-factor C monoclonal antibody (2C12)
Electrophoresis conditions: non-reducing

[Fig. 3]
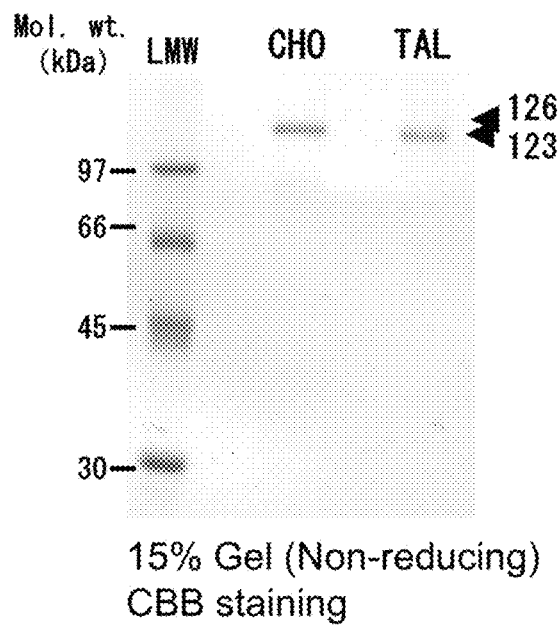
[Fig. 4]
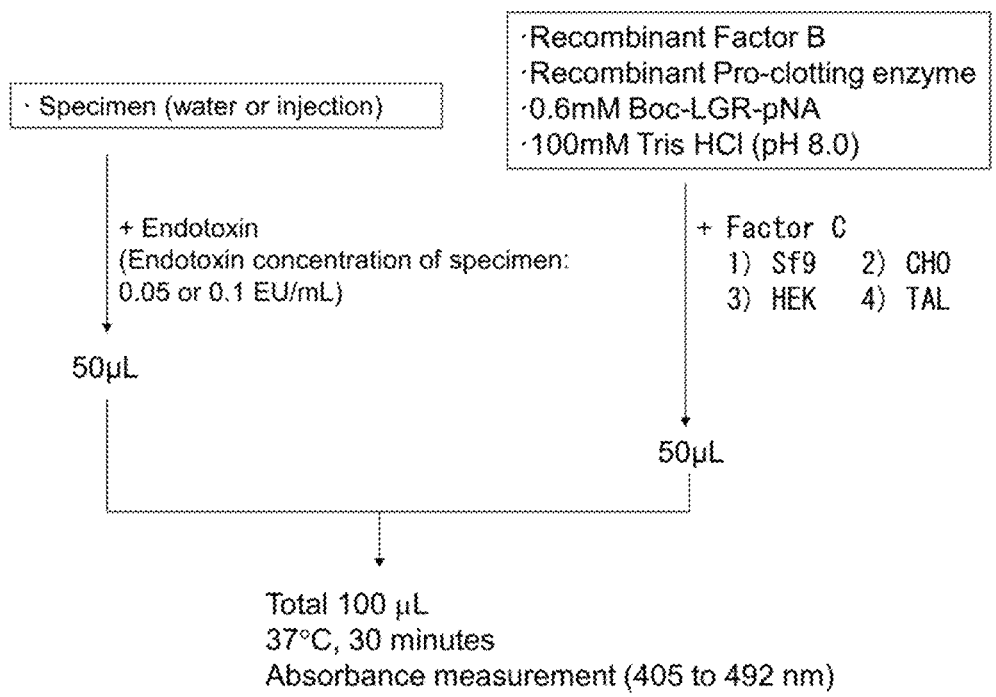

[Fig. 5]
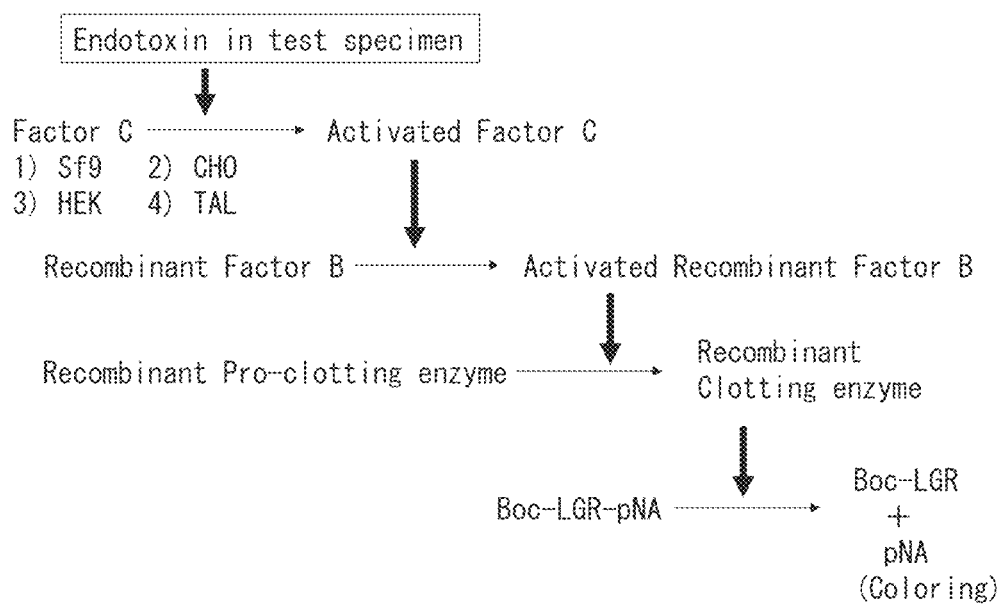

[Fig. 6]
| Host cells for Factor C | Amount of Factor C added ($\mu$L) | Endotoxin concentration (EU/mL) | Absorbance change rate (av. ± S.D.) (mAbs/min) |
|---|---|---|---|
| Sf9 | 1.5 | 0 | 0.520 ± 0.015 |
| | | 0.05 | 6.095 ± 0.108 |
| | | 0.1 | 10.795 ± 0.246 |
| CHO DG44 | 4 | 0 | 0.770 ± 0.021 |
| | | 0.05 | 7.260 ± 0.087 |
| | | 0.1 | 12.510 ± 0.255 |
| HEK293 | 8 | 0 | 0.300 ± 0.017 |
| | | 0.05 | 5.885 ± 0.125 |
| | | 0.1 | 10.685 ± 0.417 |
| TAL | 2 | 0 | 0.840 ± 0.055 |
| | | 0.05 | 7.030 ± 0.140 |
| | | 0.1 | 12.270 ± 0.255 |
n=3
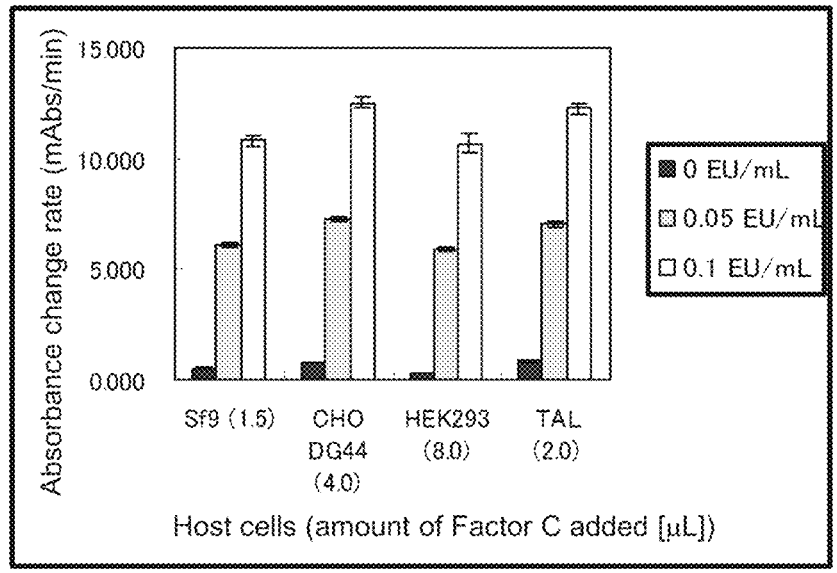

[Fig. 7]
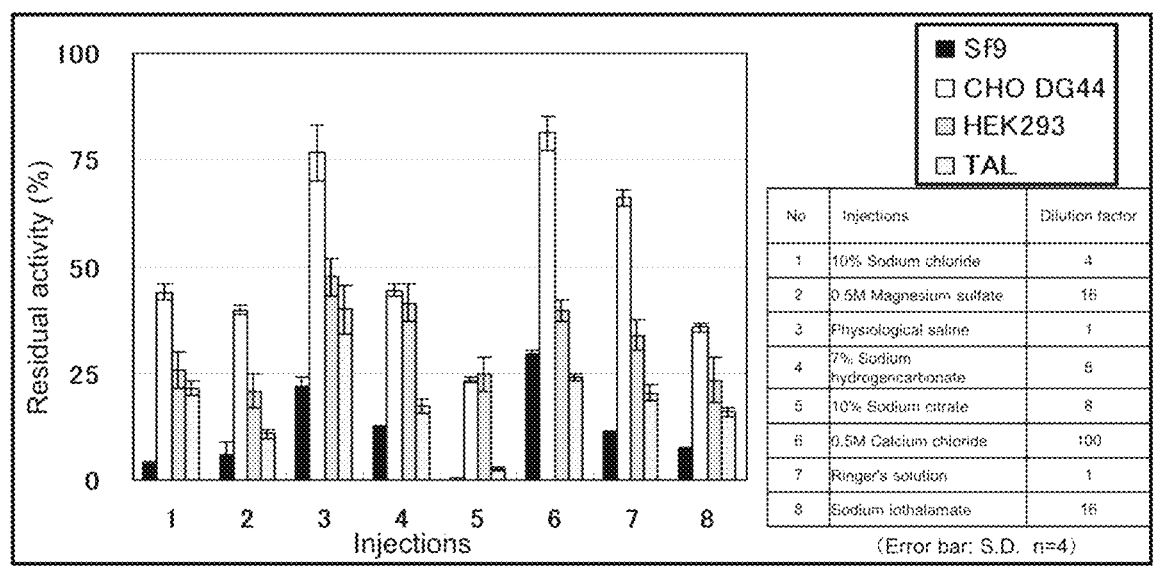

[Fig. 8]

```
TtFC       MVLASFLVSGLVLGILAQQMRPVQSRGVDLGLCDETRFECKCGDPGYVFNVPMKQCTYFY
834CrID4   MVLASFLVSGLVLGLLAQKMRPVQSKGVDLGLCDETRFECKCGDPGYVFNIPVKQCTYFY
           **************:***:******:*******************:*:*******   60

TtFC       RWRPYCKPCDDLEAKDICPKYKRCQECKAGLDSCVTCPPNKYGTWCSGECQCKNGGICDQ
834CrID4   RWRPYCKPCDDLEAKDICPKYKRCQECKAGLDSCVTCPPNKYGTWCSGECQCKNGGICDQ
           ************************************************************  120

TtFC       RTGACTCRDRYEGAHCEILKGCPLLPSDSQVQEVRNPPDNPQTIDYSCSPGFKLKGVARI
834CrID4   RTGACACRDRYEGVHCEILKGCPLLPSDSQVQEVRNPPDNPQTIDYSCSPGFKLKGMARI
           *****.*******.**********************************************:***  180

TtFC       SCLPNGGWSSFPPKCIRECAKVSSPEHGKVNAPSGNMIEGATLRFSCDSPYYLIGGETLT
834CrID4   SCLPNGGWSNFPPKCIRECAMVSSPEHGKVNALSGDMIEGATLRFSCDSPYYLIGGETLT
           *********.**********.********** **:*************************  240

TtFC       CQGNGQWSGQIPQCKKLVFCPDLDPVNHAEHQVKIGVEQKYGQFPQGTEVTYTCSGNYFL
834CrID4   CQGNGQWNGQIPQCKNLVFCPDLDPVNHAEHKVKIGVEQKYGQFPQGTEVTYTCSGNYFL
           *******.*******:**************:*****************************  300

TtFC       MGFNTLKCNPDGSWSGSQPSCVKVADREVDCDSKAVDFLDDVGEPVRIHCPAGCSLTAGT
834CrID4   MGFDTLKCNPDGSWSGSQPSCVKVADREVDCDSKAVDFLDDVGEPVRIHCPAGCSLTAGT
           ***:********************************************************  360

TtFC       VWGTAIYHELSSVCRAAIHAGKLPNSGGAVHVVNNGPYSDFLGSDLNGIKSEELKSLARS
834CrID4   VWGTAIYHELSSVCRAAIHAGKLPNSGGAVHVVNNGPYSDFLGSDLNGIKSEELKSLARS
           ************************************************************  420

TtFC       FRFDYVSSSTAGRSGCPDGWFEVEENCVYVTSKQRAWERAGGVCTNMAARLAVLDKDLIP
834CrID4   FRFDYVRSSTAGKSGCPDGWFEVDENCVYVTSKQRAWERAGGVCTNMAARLAVLDKDVIP
           ******.*****:**********:*********************************:**  480

TtFC       SSLTETLRGKGLTTTWIGLHRLDAEKPFVWELMDRSNVVLNDNLTFWASGEPGNETNCVY
834CrID4   NSLTETLRGKGLTTTWIGLHRLDAEKPFIWELMDRSNVVLNDNLTFWASGEPGNETNCVY
           .***************************:*******************************  540

TtFC       LDIRDQLQPVWKTKSCFQPSSFACMMDLSDRNKAKCDDPGPLENGHATLHGQSIDGFYAG
834CrID4   MDIQDQLQSVWKTKSCFQPSSFACMMDLSDRNKAKCDDPGSLENGHATLHGQSIDGFYAG
           :**:****.******************************.*******************  600

TtFC       SSIRYSCEVLHYLSGTETVTCTTNGTWSAPKPRCIKVITCQNPPVPSYGSVEIKPPSRTN
834CrID4   SSIRYSCEVLHYLSGTETVTCTTNGTWSAPKPRCIKVITCQNPPVPSYGSVEIKPPSRTN
           ************************************************************  660
```

[Fig. 9]

```
TtFC        SISRVGSPFLRLPRLPLPLARAAKPPPKPRSSQPSTVDLASKVKLPEGHYRVGSRAIYTC
834CrID4    SISRVGSPFLRLPRLPLPLARAAKPPPKPRSSQPSTVDLASKVKLPEGHYRVGSRAIYTC
            ************************************************************ 720

TtFC        ESRYYELLGSQGRRCDSNGNWSGRPASCIPVCGRSDSPRSPFIWNGNSTEIGGWPWQAGI
834CrID4    ESRYYELLGSQGRRCDSNGNWSGRPASCIPVCGRSDSPRSPFIWNGNSTEIGGWPWQAGI
            ************************************************************ 780

TtFC        SRWLADHNMWFLQCGGSLLNEKWIVTAAHCVTYSATAEIIDPSQFKIYLGKYYRDDSRDD
834CrID4    SRWLADHNMWFLQCGGSLLNEKWIVTAAHCVTYSATAEIIDPNQFKMYLGKYYRDDSRDD
            ******************************************.***:************ 840

TtFC        DYVQVREALEIHVNPNYDPGNLNFDIALIQLKTPVTLTTRVQPICLPTDITTREHLKEGT
834CrID4    DYVQVREALEIHVNPNYDPGNLNFDIALIQLKTPVTLTTRVQPICLPTDITTREHLKEGT
            ************************************************************ 900

TtFC        LAVVTGWGLNENNTYSEMIQQAVLPVVAASTCEEGYKEADLPLTVTENMFCAGYKKGRYD
834CrID4    LAVVTGWGLNENNTYSETIQQAVLPVVAASTCEEGYKEADLPLTVTENMFCAGYKKGRYD
            ***************** ****************************************** 960

TtFC        ACSGDSGGPLVFADDSRTERRWVLEGIVSWGSPSGCGKANQYGGFTKVNVFLSWIRQFI
834CrID4    ACSGDSGGPLVFADDSRTERRWVLEGIVSWGSPSGCGKANQYGGFTKVNVFLSWIRQFI
            *********************************************************** 1019
```

[Fig. 10]
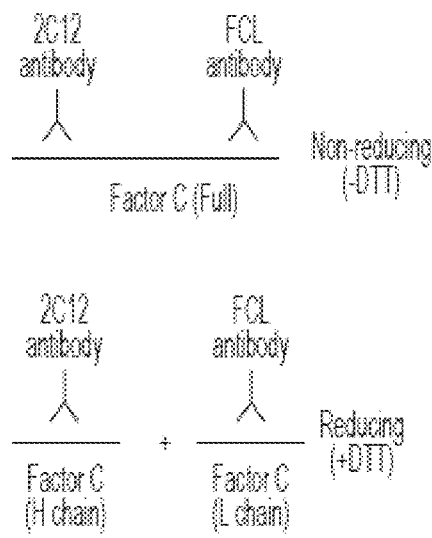
[Fig. 11]
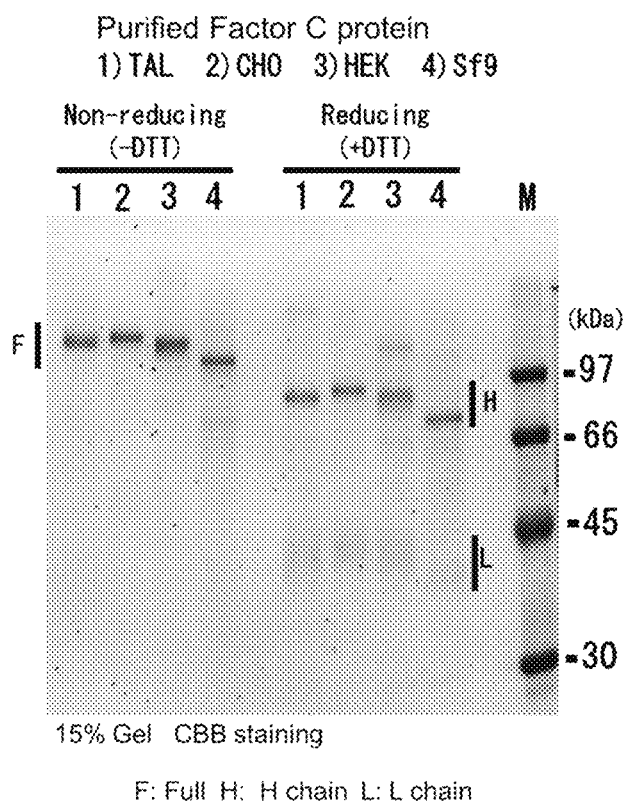

[Fig. 12]
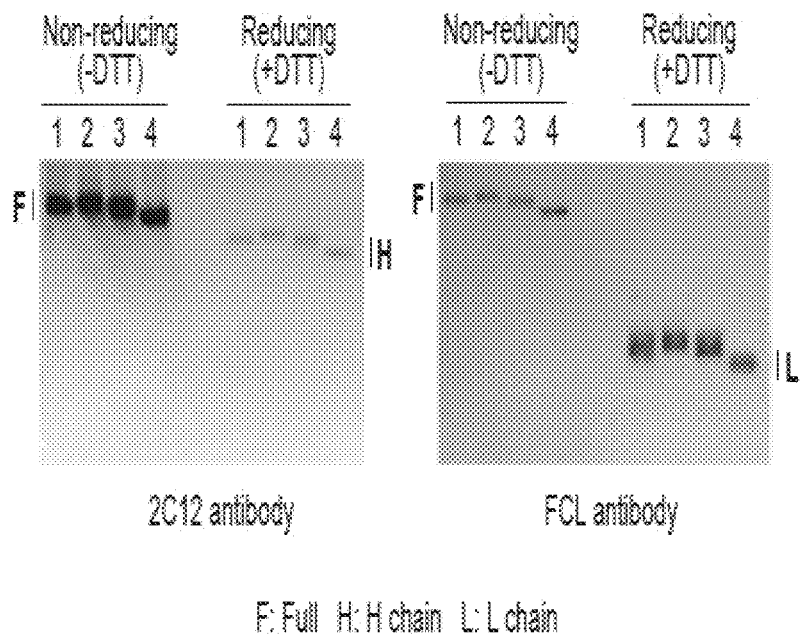
[Fig. 13]
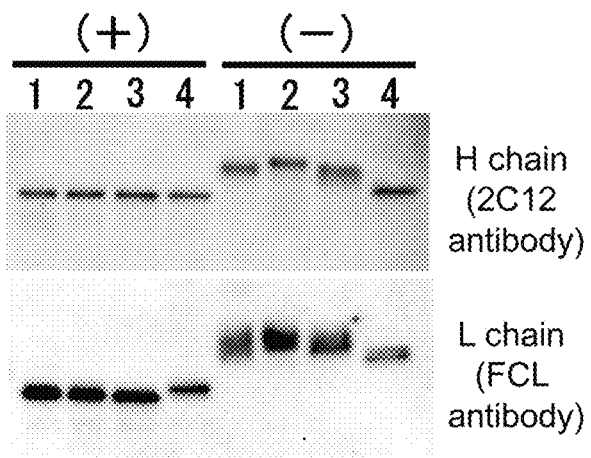

[Fig. 14]
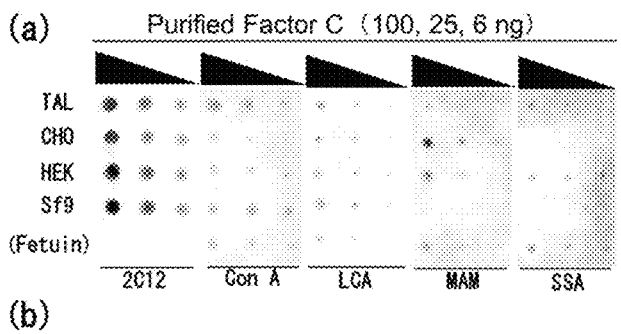
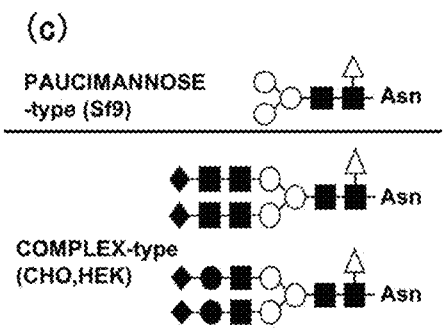

SEQUENCE LISTING

```
<160> NUMBER OF SEQ ID NOS: 10

<210> SEQ ID NO 1
<211> LENGTH: 3060
<212> TYPE: DNA
<213> ORGANISM: Tachypleus tridentatus
<220> FEATURE:
<221> NAME/KEY: CDS
<222> LOCATION: (1)..(3060)

<400> SEQUENCE: 1 atg gtc tta gcg tcg ttt ttg gtg tct ggt tta gtt cta ggg ata cta    48
Met Val Leu Ala Ser Phe Leu Val Ser Gly Leu Val Leu Gly Ile Leu
1               5                   10                  15 gcc caa caa atg cgt cca gtt cag tcc aga gga gta gat ctg ggc ttg    96
Ala Gln Gln Met Arg Pro Val Gln Ser Arg Gly Val Asp Leu Gly Leu
                20                  25                  30 tgt gat gaa acg agg ttc gag tgt aag tgt gga gat cca ggc tat gtg    144
Cys Asp Glu Thr Arg Phe Glu Cys Lys Cys Gly Asp Pro Gly Tyr Val
            35                  40                  45 ttc aac gtc cct atg aaa caa tgc acg tac ttc tat cga tgg agg cct    192
Phe Asn Val Pro Met Lys Gln Cys Thr Tyr Phe Tyr Arg Trp Arg Pro
        50                  55                  60 tat tgt aaa cca tgt gat gac ctg gag gct aag gac att tgt cca aag    240
Tyr Cys Lys Pro Cys Asp Asp Leu Glu Ala Lys Asp Ile Cys Pro Lys
65                  70                  75                  80 tac aaa cga tgt caa gag tgt aag gct ggt ctt gat agt tgt gtt act    288
Tyr Lys Arg Cys Gln Glu Cys Lys Ala Gly Leu Asp Ser Cys Val Thr
                85                  90                  95 tgt cca cct aac aaa tat ggt act tgg tgt agc ggt gaa tgt caa tgt    336
Cys Pro Pro Asn Lys Tyr Gly Thr Trp Cys Ser Gly Glu Cys Gln Cys
                100                 105                 110 aag aat gga ggt atc tgt gac cag agg aca gga gct tgt acc tgt cgt    384
Lys Asn Gly Gly Ile Cys Asp Gln Arg Thr Gly Ala Cys Thr Cys Arg
            115                 120                 125 gac aga tat gaa gga gcg cac tgt gaa att ctc aaa ggt tgt cct ctt    432
Asp Arg Tyr Glu Gly Ala His Cys Glu Ile Leu Lys Gly Cys Pro Leu
        130                 135                 140
```

-continued

| | | |
|---|---|---|
| ctt cca tcg gat tct caa gtt cag gaa gtc aga aac cca cca gat aat<br>Leu Pro Ser Asp Ser Gln Val Gln Glu Val Arg Asn Pro Pro Asp Asn<br>145                    150                    155                    160 | 480 |
| ccc caa act att gac tac agc tgt tca cca ggg ttc aag ctt aaa ggc<br>Pro Gln Thr Ile Asp Tyr Ser Cys Ser Pro Gly Phe Lys Leu Lys Gly<br>                    165                    170                    175 | 528 |
| gtg gca cga att agc tgt ctc cca aat gga cag tgg agt agc ttt cca<br>Val Ala Arg Ile Ser Cys Leu Pro Asn Gly Gln Trp Ser Ser Phe Pro<br>            180                    185                    190 | 576 |
| ccc aaa tgt att cga gaa tgt gcc aag gtt tca tct cca gaa cac ggg<br>Pro Lys Cys Ile Arg Glu Cys Ala Lys Val Ser Ser Pro Glu His Gly<br>                195                    200                    205 | 624 |
| aaa gtg aat gct cct agt ggc aat atg ata gaa ggg gct act tta cgg<br>Lys Val Asn Ala Pro Ser Gly Asn Met Ile Glu Gly Ala Thr Leu Arg<br>210                    215                    220 | 672 |
| ttc tca tgt gat agt ccc tac tac ttg att ggt caa gaa aca tta acc<br>Phe Ser Cys Asp Ser Pro Tyr Tyr Leu Ile Gly Gln Glu Thr Leu Thr<br>225                    230                    235                    240 | 720 |
| tgc cag ggt aat ggt cag tgg agt gga caa ata cca caa tgt aag aag<br>Cys Gln Gly Asn Gly Gln Trp Ser Gly Gln Ile Pro Gln Cys Lys Lys<br>                    245                    250                    255 | 768 |
| ttg gtc ttc tgt cct gac ctt gat cct gta aac cat gct gaa cac cag<br>Leu Val Phe Cys Pro Asp Leu Asp Pro Val Asn His Ala Glu His Gln<br>            260                    265                    270 | 816 |
| gtt aaa att ggt gtg gaa caa aaa tat ggt cag ttt cct caa ggc act<br>Val Lys Ile Gly Val Glu Gln Lys Tyr Gly Gln Phe Pro Gln Gly Thr<br>                275                    280                    285 | 864 |
| gaa gtg acc tat acg tgt tcg ggt aac tac ttc ttg atg ggt ttt aac<br>Glu Val Thr Tyr Thr Cys Ser Gly Asn Tyr Phe Leu Met Gly Phe Asn<br>290                    295                    300 | 912 |
| acc tta aaa tgt aac cct gat ggg tcc tgg tca gga tca cag cca tcc<br>Thr Leu Lys Cys Asn Pro Asp Gly Ser Trp Ser Gly Ser Gln Pro Ser<br>305                    310                    315                    320 | 960 |
| tgt gtt aaa gtg gca gac aga gag gtc gac tgt gac agt aaa gct gta<br>Cys Val Lys Val Ala Asp Arg Glu Val Asp Cys Asp Ser Lys Ala Val<br>                    325                    330                    335 | 1008 |
| gac ttc ttg gat gat gtt ggt gaa cct gtc agg atc cac tgt cct gct<br>Asp Phe Leu Asp Asp Val Gly Glu Pro Val Arg Ile His Cys Pro Ala<br>            340                    345                    350 | 1056 |
| ggc tgt tct ttg aca gct ggt act gtg tgg ggt aca gcc ata tac cac<br>Gly Cys Ser Leu Thr Ala Gly Thr Val Trp Gly Thr Ala Ile Tyr His<br>                355                    360                    365 | 1104 |
| gaa ctt tcc tca gtg tgt cgt gca gcc atc cat gct ggc aag ctt cca<br>Glu Leu Ser Ser Val Cys Arg Ala Ala Ile His Ala Gly Lys Leu Pro<br>370                    375                    380 | 1152 |
| aac tct gga ggg gcg gtg cat gta gtg aac aat ggc ccc tac tcg gac<br>Asn Ser Gly Gly Ala Val His Val Val Asn Asn Gly Pro Tyr Ser Asp<br>385                    390                    395                    400 | 1200 |
| ttt ctg ggt agt gac ctg aat ggg ata aaa tcg gaa gag ttg aag tct<br>Phe Leu Gly Ser Asp Leu Asn Gly Ile Lys Ser Glu Glu Leu Lys Ser<br>                    405                    410                    415 | 1248 |
| ctt gcc cgc agt ttt cga ttt gat tat gtc agt tca tcc aca gca ggt<br>Leu Ala Arg Ser Phe Arg Phe Asp Tyr Val Ser Ser Ser Thr Ala Gly<br>            420                    425                    430 | 1296 |
| aga tca gga tgt cct gat gga tgg ttt gag gta gaa gag aac tgt gtg<br>Arg Ser Gly Cys Pro Asp Gly Trp Phe Glu Val Glu Glu Asn Cys Val<br>                435                    440                    445 | 1344 |
| tac gtt aca tca aaa cag aga gcc tgg gaa aga gct caa ggt gtg tgt<br>Tyr Val Thr Ser Lys Gln Arg Ala Trp Glu Arg Ala Gln Gly Val Cys | 1392 |

-continued

|  |  |  |  |  |  |  |  |  |
|---|---|---|---|---|---|---|---|---|
|  |  | 450 |  |  | 455 |  | 460 |  |
| acc<br>Thr<br>465 | aat<br>Asn | atg<br>Met | gct<br>Ala | gct<br>Ala<br>470 | cgt<br>Arg | ctt<br>Leu | gct<br>Ala | gtg cta gac aaa gat cta att ccg<br>Val Leu Asp Lys Asp Leu Ile Pro<br>475            480 | 1440 |
| agt<br>Ser | tcc<br>Ser | ttg<br>Leu | act<br>Thr | gag<br>Glu<br>485 | act<br>Thr | cta<br>Leu | cga<br>Arg | ggg aaa ggg tta aca acc aca tgg<br>Gly Lys Gly Leu Thr Thr Thr Trp<br>490            495 | 1488 |
| ata<br>Ile | gga<br>Gly | ttg<br>Leu | cac<br>His<br>500 | aga<br>Arg | cta<br>Leu | gat<br>Asp | gct<br>Ala | gag aag ccc ttt gtt tgg gag cta<br>Glu Lys Pro Phe Val Trp Glu Leu<br>505            510 | 1536 |
| atg<br>Met | gat<br>Asp | cgt<br>Arg<br>515 | agt<br>Ser | aat<br>Asn | gtg<br>Val | gtt<br>Val<br>520 | ctg<br>Leu | aat gat aac cta aca ttc tgg gcc<br>Asn Asp Asn Leu Thr Phe Trp Ala<br>525 | 1584 |
| tct<br>Ser | ggc<br>Gly<br>530 | gaa<br>Glu | cct<br>Pro | gga<br>Gly | aat<br>Asn | gaa<br>Glu<br>535 | act<br>Thr | aac tgt gta tat ctg gac atc cga<br>Asn Cys Val Tyr Leu Asp Ile Arg<br>540 | 1632 |
| gat<br>Asp<br>545 | cag<br>Gln | ctg<br>Leu | cag<br>Gln | cct<br>Pro<br>550 | gtg<br>Val | tgg<br>Trp | aaa<br>Lys | acc aag tca tgt ttt cag ccc tca<br>Thr Lys Ser Cys Phe Gln Pro Ser<br>555            560 | 1680 |
| agc<br>Ser | ttt<br>Phe | gct<br>Ala | tgc<br>Cys<br>565 | atg<br>Met | atg<br>Met | gat<br>Asp | ttg<br>Leu | tca gac aga aat aaa gcc aaa tgc<br>Ser Asp Arg Asn Lys Ala Lys Cys<br>570            575 | 1728 |
| gat<br>Asp | gac<br>Asp | cct<br>Pro<br>580 | gga<br>Gly | cca<br>Pro | ctg<br>Leu | gaa<br>Glu | aat<br>Asn<br>585 | gga cac gcc aca ctt cat gga caa<br>Gly His Ala Thr Leu His Gly Gln<br>590 | 1776 |
| agt<br>Ser | att<br>Ile | gat<br>Asp<br>595 | ggg<br>Gly | ttc<br>Phe | tat<br>Tyr | gct<br>Ala | ggt<br>Gly<br>600 | tct tct ata agg tac agc tgt gag<br>Ser Ser Ile Arg Tyr Ser Cys Glu<br>605 | 1824 |
| gtt<br>Val | ctc<br>Leu<br>610 | cac<br>His | tac<br>Tyr | ctc<br>Leu | agt<br>Ser | gga<br>Gly<br>615 | act<br>Thr | gag acc gta act tgt aca aca aat<br>Glu Thr Val Thr Cys Thr Thr Asn<br>620 | 1872 |
| ggc<br>Gly<br>625 | aca<br>Thr | tgg<br>Trp | agt<br>Ser | gct<br>Ala<br>630 | cct<br>Pro | aaa<br>Lys | cct<br>Pro | cga tgt atc aaa gtc atc acc tgc<br>Arg Cys Ile Lys Val Ile Thr Cys<br>635            640 | 1920 |
| caa<br>Gln | aac<br>Asn | cct<br>Pro | cct<br>Pro<br>645 | gta<br>Val | cca<br>Pro | tca<br>Ser | tat<br>Tyr | ggt tct gtg gaa atc aaa ccc cca<br>Gly Ser Val Glu Ile Lys Pro Pro<br>650            655 | 1968 |
| agt<br>Ser | cgg<br>Arg | aca<br>Thr<br>660 | aac<br>Asn | tcg<br>Ser | atc<br>Ile | agt<br>Ser | cgt<br>Arg<br>665 | gtt ggg tca cct ttc ttg agg ttg<br>Val Gly Ser Pro Phe Leu Arg Leu<br>670 | 2016 |
| cca<br>Pro | cgg<br>Arg<br>675 | tta<br>Leu | ccc<br>Pro | ctc<br>Leu | cca<br>Pro | tta<br>Leu<br>680 | gcc<br>Ala | aga gca gcc aaa cct cct cca aaa<br>Arg Ala Ala Lys Pro Pro Pro Lys<br>685 | 2064 |
| cct<br>Pro | aga<br>Arg<br>690 | tcc<br>Ser | tca<br>Ser | caa<br>Gln | ccc<br>Pro<br>695 | tct<br>Ser | act<br>Thr | gtg gac ttg gct tct aaa gtt aaa<br>Val Asp Leu Ala Ser Lys Val Lys<br>700 | 2112 |
| cta<br>Leu<br>705 | cct<br>Pro | gaa<br>Glu | ggt<br>Gly | cat<br>His<br>710 | tac<br>Tyr | cgg<br>Arg | gta<br>Val | ggg tct cga gcc att tac acg tgc<br>Gly Ser Arg Ala Ile Tyr Thr Cys<br>715            720 | 2160 |
| gag<br>Glu | tcg<br>Ser | aga<br>Arg | tac<br>Tyr<br>725 | tac<br>Tyr | gaa<br>Glu | cta<br>Leu | ctt<br>Leu | gga tct caa ggc aga aga tgt gac<br>Gly Ser Gln Gly Arg Arg Cys Asp<br>730            735 | 2208 |
| tct<br>Ser | aat<br>Asn | gga<br>Gly<br>740 | aac<br>Asn | tgg<br>Trp | agt<br>Ser | ggt<br>Gly | cgg<br>Arg<br>745 | ccc gct agc tgt att cca gtt tgt<br>Pro Ala Ser Cys Ile Pro Val Cys<br>750 | 2256 |
| gga<br>Gly | cgg<br>Arg<br>755 | tca<br>Ser | gac<br>Asp | tct<br>Ser | cct<br>Pro | cgt<br>Arg<br>760 | tct<br>Ser | cct ttc atc tgg aat ggg aat tct<br>Pro Phe Ile Trp Asn Gly Asn Ser<br>765 | 2304 |
| aca<br>Thr | gaa<br>Glu | ata<br>Ile | ggt<br>Gly | cag<br>Gln | tgg<br>Trp | ccg<br>Pro | tgg<br>Trp | cag gca gga atc tct cga tgg ctt<br>Gln Ala Gly Ile Ser Arg Trp Leu | 2352 |

```
Thr Glu Ile Gly Gln Trp Pro Trp Gln Ala Gly Ile Ser Arg Trp Leu
    770             775                 780 gca gac cac aat atg tgg ttt ctc cag tgt gga gga tcc cta ttg aat    2400
Ala Asp His Asn Met Trp Phe Leu Gln Cys Gly Gly Ser Leu Leu Asn
785             790                 795                 800 gag aaa tgg atc gtc act gct gcc cac tgt gtc acc tac tct gct act    2448
Glu Lys Trp Ile Val Thr Ala Ala His Cys Val Thr Tyr Ser Ala Thr
                805                 810                 815 gct gag ata att gat ccc agt cag ttt aaa atc tat ctg ggc aag tac    2496
Ala Glu Ile Ile Asp Pro Ser Gln Phe Lys Ile Tyr Leu Gly Lys Tyr
            820                 825                 830 tac cgt gat gac agt aga gac gat gac tac gta caa gta aga gag gct    2544
Tyr Arg Asp Asp Ser Arg Asp Asp Asp Tyr Val Gln Val Arg Glu Ala
        835                 840                 845 ctc gag atc cac gta aat cct aac tac gac ccc ggc aat ctc aac ttt    2592
Leu Glu Ile His Val Asn Pro Asn Tyr Asp Pro Gly Asn Leu Asn Phe
    850                 855                 860 gac ata gcc cta att caa ctg aaa act cct gtt act ttg aca aca cga    2640
Asp Ile Ala Leu Ile Gln Leu Lys Thr Pro Val Thr Leu Thr Thr Arg
865                 870                 875                 880 gtc caa cca atc tgt ctg cct act gac atc aca aca aga gaa cac ttg    2688
Val Gln Pro Ile Cys Leu Pro Thr Asp Ile Thr Thr Arg Glu His Leu
                885                 890                 895 aag gag gga aca tta gca gtg gtg aca ggt tgg ggt ttg aat gaa aac    2736
Lys Glu Gly Thr Leu Ala Val Val Thr Gly Trp Gly Leu Asn Glu Asn
            900                 905                 910 aac aca tat tca gag atg att caa caa gct gtg cta cct gtt gtt gca    2784
Asn Thr Tyr Ser Glu Met Ile Gln Gln Ala Val Leu Pro Val Val Ala
        915                 920                 925 gca agc acc tgt gaa gag ggg tac aag gaa gca gac tta cca ctg aca    2832
Ala Ser Thr Cys Glu Glu Gly Tyr Lys Glu Ala Asp Leu Pro Leu Thr
    930                 935                 940 gta aca gag aac atg ttc tgt gca ggt tac aag aag gga cgt tat gat    2880
Val Thr Glu Asn Met Phe Cys Ala Gly Tyr Lys Lys Gly Arg Tyr Asp
945                 950                 955                 960 gcc tgc agt ggg gac agt gga gga cca tta gtg ttt gct gat gat tcc    2928
Ala Cys Ser Gly Asp Ser Gly Gly Pro Leu Val Phe Ala Asp Asp Ser
                965                 970                 975 cgt acc gaa agg cgg tgg gtc ttg gaa ggg att gtc agc tgg ggc agt    2976
Arg Thr Glu Arg Arg Trp Val Leu Glu Gly Ile Val Ser Trp Gly Ser
            980                 985                 990 ccc agt gga tgt ggc aag gct aac cag tat ggg ggc ttc act aaa gtt    3024
Pro Ser Gly Cys Gly Lys Ala Asn Gln Tyr Gly Gly Phe Thr Lys Val
        995                 1000                1005 aac gtt ttt cta tca tgg att agg cag ttc att tga                    3060
Asn Val Phe Leu Ser Trp Ile Arg Gln Phe Ile
    1010                1015

<210> SEQ ID NO 2
<211> LENGTH: 1019
<212> TYPE: PRT
<213> ORGANISM: Tachypleus tridentatus

<400> SEQUENCE: 2

Met Val Leu Ala Ser Phe Leu Val Ser Gly Leu Val Leu Gly Ile Leu
1               5                   10                  15

Ala Gln Gln Met Arg Pro Val Gln Ser Arg Gly Val Asp Leu Gly Leu
            20                  25                  30

Cys Asp Glu Thr Arg Phe Glu Cys Lys Cys Gly Asp Pro Gly Tyr Val
        35                  40                  45
```

-continued

```
Phe Asn Val Pro Met Lys Gln Cys Thr Tyr Phe Tyr Arg Trp Arg Pro
    50              55                  60

Tyr Cys Lys Pro Cys Asp Asp Leu Glu Ala Lys Asp Ile Cys Pro Lys
65              70                  75                  80

Tyr Lys Arg Cys Gln Glu Cys Lys Ala Gly Leu Asp Ser Cys Val Thr
                85                  90                  95

Cys Pro Pro Asn Lys Tyr Gly Thr Trp Cys Ser Gly Glu Cys Gln Cys
                100                 105                 110

Lys Asn Gly Gly Ile Cys Asp Gln Arg Thr Gly Ala Cys Thr Cys Arg
            115                 120                 125

Asp Arg Tyr Glu Gly Ala His Cys Glu Ile Leu Lys Gly Cys Pro Leu
    130                 135                 140

Leu Pro Ser Asp Ser Gln Val Gln Glu Val Arg Asn Pro Pro Asp Asn
145                 150                 155                 160

Pro Gln Thr Ile Asp Tyr Ser Cys Ser Pro Gly Phe Lys Leu Lys Gly
                165                 170                 175

Val Ala Arg Ile Ser Cys Leu Pro Asn Gly Gln Trp Ser Ser Phe Pro
                180                 185                 190

Pro Lys Cys Ile Arg Glu Cys Ala Lys Val Ser Ser Pro Glu His Gly
            195                 200                 205

Lys Val Asn Ala Pro Ser Gly Asn Met Ile Glu Gly Ala Thr Leu Arg
    210                 215                 220

Phe Ser Cys Asp Ser Pro Tyr Tyr Leu Ile Gly Gln Glu Thr Leu Thr
225                 230                 235                 240

Cys Gln Gly Asn Gly Gln Trp Ser Gly Gln Ile Pro Gln Cys Lys Lys
                245                 250                 255

Leu Val Phe Cys Pro Asp Leu Asp Pro Val Asn His Ala Glu His Gln
                260                 265                 270

Val Lys Ile Gly Val Glu Gln Lys Tyr Gly Gln Phe Pro Gln Gly Thr
    275                 280                 285

Glu Val Thr Tyr Thr Cys Ser Gly Asn Tyr Phe Leu Met Gly Phe Asn
    290                 295                 300

Thr Leu Lys Cys Asn Pro Asp Gly Ser Trp Ser Gly Ser Gln Pro Ser
305                 310                 315                 320

Cys Val Lys Val Ala Asp Arg Glu Val Asp Cys Asp Ser Lys Ala Val
                325                 330                 335

Asp Phe Leu Asp Asp Val Gly Glu Pro Val Arg Ile His Cys Pro Ala
                340                 345                 350

Gly Cys Ser Leu Thr Ala Gly Thr Val Trp Gly Thr Ala Ile Tyr His
            355                 360                 365

Glu Leu Ser Ser Val Cys Arg Ala Ala Ile His Ala Gly Lys Leu Pro
    370                 375                 380

Asn Ser Gly Gly Ala Val His Val Val Asn Asn Gly Pro Tyr Ser Asp
385                 390                 395                 400

Phe Leu Gly Ser Asp Leu Asn Gly Ile Lys Ser Glu Glu Leu Lys Ser
                405                 410                 415

Leu Ala Arg Ser Phe Arg Phe Asp Tyr Val Ser Ser Ser Thr Ala Gly
                420                 425                 430

Arg Ser Gly Cys Pro Asp Gly Trp Phe Glu Val Glu Glu Asn Cys Val
            435                 440                 445

Tyr Val Thr Ser Lys Gln Arg Ala Trp Glu Arg Ala Gln Gly Val Cys
    450                 455                 460
```

-continued

Thr Asn Met Ala Ala Arg Leu Ala Val Leu Asp Lys Asp Leu Ile Pro
465                 470                 475                 480

Ser Ser Leu Thr Glu Thr Leu Arg Gly Lys Gly Leu Thr Thr Thr Trp
        485                 490                 495

Ile Gly Leu His Arg Leu Asp Ala Glu Lys Pro Phe Val Trp Glu Leu
            500                 505                 510

Met Asp Arg Ser Asn Val Val Leu Asn Asp Asn Leu Thr Phe Trp Ala
        515                 520                 525

Ser Gly Glu Pro Gly Asn Glu Thr Asn Cys Val Tyr Leu Asp Ile Arg
530                 535                 540

Asp Gln Leu Gln Pro Val Trp Lys Thr Lys Ser Cys Phe Gln Pro Ser
545                 550                 555                 560

Ser Phe Ala Cys Met Met Asp Leu Ser Asp Arg Asn Lys Ala Lys Cys
                565                 570                 575

Asp Asp Pro Gly Pro Leu Glu Asn Gly His Ala Thr Leu His Gly Gln
            580                 585                 590

Ser Ile Asp Gly Phe Tyr Ala Gly Ser Ser Ile Arg Tyr Ser Cys Glu
        595                 600                 605

Val Leu His Tyr Leu Ser Gly Thr Glu Thr Val Thr Cys Thr Thr Asn
        610                 615                 620

Gly Thr Trp Ser Ala Pro Lys Pro Arg Cys Ile Lys Val Ile Thr Cys
625                 630                 635                 640

Gln Asn Pro Pro Val Pro Ser Tyr Gly Ser Val Glu Ile Lys Pro Pro
                645                 650                 655

Ser Arg Thr Asn Ser Ile Ser Arg Val Gly Ser Pro Phe Leu Arg Leu
            660                 665                 670

Pro Arg Leu Pro Leu Pro Leu Ala Arg Ala Ala Lys Pro Pro Pro Lys
        675                 680                 685

Pro Arg Ser Ser Gln Pro Ser Thr Val Asp Leu Ala Ser Lys Val Lys
        690                 695                 700

Leu Pro Glu Gly His Tyr Arg Val Gly Ser Arg Ala Ile Tyr Thr Cys
705                 710                 715                 720

Glu Ser Arg Tyr Tyr Glu Leu Leu Gly Ser Gln Gly Arg Arg Cys Asp
                725                 730                 735

Ser Asn Gly Asn Trp Ser Gly Arg Pro Ala Ser Cys Ile Pro Val Cys
            740                 745                 750

Gly Arg Ser Asp Ser Pro Arg Ser Pro Phe Ile Trp Asn Gly Asn Ser
        755                 760                 765

Thr Glu Ile Gly Gln Trp Pro Trp Gln Ala Gly Ile Ser Arg Trp Leu
770                 775                 780

Ala Asp His Asn Met Trp Phe Leu Gln Cys Gly Gly Ser Leu Leu Asn
785                 790                 795                 800

Glu Lys Trp Ile Val Thr Ala Ala His Cys Val Thr Tyr Ser Ala Thr
                805                 810                 815

Ala Glu Ile Ile Asp Pro Ser Gln Phe Lys Ile Tyr Leu Gly Lys Tyr
            820                 825                 830

Tyr Arg Asp Asp Ser Arg Asp Asp Tyr Val Gln Val Arg Glu Ala
        835                 840                 845

Leu Glu Ile His Val Asn Pro Asn Tyr Asp Pro Gly Asn Leu Asn Phe
        850                 855                 860

Asp Ile Ala Leu Ile Gln Leu Lys Thr Pro Val Thr Leu Thr Thr Arg
865                 870                 875                 880

Val Gln Pro Ile Cys Leu Pro Thr Asp Ile Thr Thr Arg Glu His Leu

```
                    885                 890                 895
Lys Glu Gly Thr Leu Ala Val Val Thr Gly Trp Gly Leu Asn Glu Asn
                900                 905                 910

Asn Thr Tyr Ser Glu Met Ile Gln Gln Ala Val Leu Pro Val Val Ala
            915                 920                 925

Ala Ser Thr Cys Glu Glu Gly Tyr Lys Glu Ala Asp Leu Pro Leu Thr
        930                 935                 940

Val Thr Glu Asn Met Phe Cys Ala Gly Tyr Lys Lys Gly Arg Tyr Asp
945                 950                 955                 960

Ala Cys Ser Gly Asp Ser Gly Gly Pro Leu Val Phe Ala Asp Asp Ser
                965                 970                 975

Arg Thr Glu Arg Arg Trp Val Leu Glu Gly Ile Val Ser Trp Gly Ser
            980                 985                 990

Pro Ser Gly Cys Gly Lys Ala Asn  Gln Tyr Gly Gly Phe  Thr Lys Val
        995                 1000                1005

Asn Val  Phe Leu Ser Trp Ile  Arg Gln Phe Ile
    1010                 1015

<210> SEQ ID NO 3
<211> LENGTH: 3060
<212> TYPE: DNA
<213> ORGANISM: Carcinoscorpius rotundicauda
<220> FEATURE:
<221> NAME/KEY: CDS
<222> LOCATION: (1)..(3060)

<400> SEQUENCE: 3 atg gtc tta gcg tcg ttt ttg gtg tct ggt tta gtt cta ggg cta cta    48
Met Val Leu Ala Ser Phe Leu Val Ser Gly Leu Val Leu Gly Leu Leu
1               5                   10                  15 gcc caa aaa atg cgc cca gtt cag tcc aaa gga gta gat cta ggc ttg    96
Ala Gln Lys Met Arg Pro Val Gln Ser Lys Gly Val Asp Leu Gly Leu
            20                  25                  30 tgt gat gaa acg agg ttc gag tgt aag tgt ggc gat cca ggc tat gtg   144
Cys Asp Glu Thr Arg Phe Glu Cys Lys Cys Gly Asp Pro Gly Tyr Val
        35                  40                  45 ttc aac att cca gtg aaa caa tgt aca tac ttt tat cga tgg agg ccg   192
Phe Asn Ile Pro Val Lys Gln Cys Thr Tyr Phe Tyr Arg Trp Arg Pro
    50                  55                  60 tat tgt aaa cca tgt gat gac ctg gag gct aag gat att tgt cca aag   240
Tyr Cys Lys Pro Cys Asp Asp Leu Glu Ala Lys Asp Ile Cys Pro Lys
65                  70                  75                  80 tac aaa cga tgt caa gag tgt aag gct ggt ctt gat agt tgt gtt act   288
Tyr Lys Arg Cys Gln Glu Cys Lys Ala Gly Leu Asp Ser Cys Val Thr
                85                  90                  95 tgt cca cct aac aaa tat ggt act tgg tgt agc ggt gaa tgt cag tgt   336
Cys Pro Pro Asn Lys Tyr Gly Thr Trp Cys Ser Gly Glu Cys Gln Cys
            100                 105                 110 aag aat gga ggt atc tgt gac cag agg aca gga gct tgt gca tgt cgt   384
Lys Asn Gly Gly Ile Cys Asp Gln Arg Thr Gly Ala Cys Ala Cys Arg
        115                 120                 125 gac aga tat gaa ggg gtg cac tgt gaa att ctc aaa ggt tgt cct ctt   432
Asp Arg Tyr Glu Gly Val His Cys Glu Ile Leu Lys Gly Cys Pro Leu
    130                 135                 140 ctt cca tcg gat tct cag gtt cag gaa gtc aga aat cca cca gat aat   480
Leu Pro Ser Asp Ser Gln Val Gln Glu Val Arg Asn Pro Pro Asp Asn
145                 150                 155                 160 ccc caa act att gac tac agc tgt tca cca ggg ttc aag ctt aag ggt   528
Pro Gln Thr Ile Asp Tyr Ser Cys Ser Pro Gly Phe Lys Leu Lys Gly
```

```
                  165                 170                  175
atg gca cga att agc tgt ctc cca aat gga cag tgg agt aac ttt cca      576
Met Ala Arg Ile Ser Cys Leu Pro Asn Gly Gln Trp Ser Asn Phe Pro
        180                 185                 190 ccc aaa tgt att cga gaa tgt gcc atg gtt tca tct cca gaa cat ggg      624
Pro Lys Cys Ile Arg Glu Cys Ala Met Val Ser Ser Pro Glu His Gly
        195                 200                 205 aaa gtg aat gct ctt agt ggt gat atg ata gaa ggg gct act tta cgg      672
Lys Val Asn Ala Leu Ser Gly Asp Met Ile Glu Gly Ala Thr Leu Arg
    210                 215                 220 ttc tca tgt gat agt ccc tac tac ttg att ggt caa gaa aca tta acc      720
Phe Ser Cys Asp Ser Pro Tyr Tyr Leu Ile Gly Gln Glu Thr Leu Thr
225                 230                 235                 240 tgt cag ggt aat ggt cag tgg aat gga cag ata cca caa tgt aag aac      768
Cys Gln Gly Asn Gly Gln Trp Asn Gly Gln Ile Pro Gln Cys Lys Asn
                245                 250                 255 ttg gtc ttc tgt cct gac ctg gat cct gta aac cat gct gaa cac aag      816
Leu Val Phe Cys Pro Asp Leu Asp Pro Val Asn His Ala Glu His Lys
            260                 265                 270 gtt aaa att ggt gtg gaa caa aaa tat ggt cag ttt cct caa ggc act      864
Val Lys Ile Gly Val Glu Gln Lys Tyr Gly Gln Phe Pro Gln Gly Thr
        275                 280                 285 gaa gtg acc tat acg tgt tcg ggt aac tac ttc ttg atg ggt ttt gac      912
Glu Val Thr Tyr Thr Cys Ser Gly Asn Tyr Phe Leu Met Gly Phe Asp
    290                 295                 300 acc tta aaa tgt aac cct gat ggg tct tgg tca gga tca cag cca tcc      960
Thr Leu Lys Cys Asn Pro Asp Gly Ser Trp Ser Gly Ser Gln Pro Ser
305                 310                 315                 320 tgt gtt aaa gtg gca gac aga gag gtc gac tgt gac agt aaa gct gta     1008
Cys Val Lys Val Ala Asp Arg Glu Val Asp Cys Asp Ser Lys Ala Val
                325                 330                 335 gac ttc ttg gat gat gtt ggt gaa cct gtc agg atc cac tgt cct gct     1056
Asp Phe Leu Asp Asp Val Gly Glu Pro Val Arg Ile His Cys Pro Ala
            340                 345                 350 ggc tgt tct ttg aca gct ggt act gtg tgg ggt aca gcc ata tac cat     1104
Gly Cys Ser Leu Thr Ala Gly Thr Val Trp Gly Thr Ala Ile Tyr His
        355                 360                 365 gaa ctt tcc tca gtg tgt cgt gca gcc atc cat gct ggc aag ctt cca     1152
Glu Leu Ser Ser Val Cys Arg Ala Ala Ile His Ala Gly Lys Leu Pro
    370                 375                 380 aac tct gga gga gcg gtg cat gtt gtg aac aat ggc ccc tac tcg gac     1200
Asn Ser Gly Gly Ala Val His Val Val Asn Asn Gly Pro Tyr Ser Asp
385                 390                 395                 400 ttt ctg ggt agt gac ctg aat ggg ata aaa tcg gaa gag ttg aag tct     1248
Phe Leu Gly Ser Asp Leu Asn Gly Ile Lys Ser Glu Glu Leu Lys Ser
                405                 410                 415 ctt gcc cgg agt ttc cga ttc gat tat gtc cgt tcc tcc aca gca ggt     1296
Leu Ala Arg Ser Phe Arg Phe Asp Tyr Val Arg Ser Ser Thr Ala Gly
            420                 425                 430 aaa tca gga tgt cct gat gga tgg ttt gag gta gac gag aac tgt gtg     1344
Lys Ser Gly Cys Pro Asp Gly Trp Phe Glu Val Asp Glu Asn Cys Val
        435                 440                 445 tac gtt aca tca aaa cag aga gcc tgg gaa aga gct caa ggt gtg tgt     1392
Tyr Val Thr Ser Lys Gln Arg Ala Trp Glu Arg Ala Gln Gly Val Cys
    450                 455                 460 acc aat atg gct gct cgt ctt gct gtg ctg gac aaa gat gta att cca     1440
Thr Asn Met Ala Ala Arg Leu Ala Val Leu Asp Lys Asp Val Ile Pro
465                 470                 475                 480 aat tcg ttg act gag act cta cga ggg aaa ggg tta aca acc acg tgg     1488
```

```
                Asn Ser Leu Thr Glu Thr Leu Arg Gly Lys Gly Leu Thr Thr Thr Trp
                                485                 490                 495 ata gga ttg cac aga cta gat gct gag aag ccc ttt att tgg gag tta          1536
Ile Gly Leu His Arg Leu Asp Ala Glu Lys Pro Phe Ile Trp Glu Leu
            500                 505                 510 atg gat cgt agt aat gtg gtt ctg aat gat aac cta aca ttc tgg gcc          1584
Met Asp Arg Ser Asn Val Val Leu Asn Asp Asn Leu Thr Phe Trp Ala
            515                 520                 525 tct ggc gaa cct gga aat gaa act aac tgt gta tat atg gac atc caa          1632
Ser Gly Glu Pro Gly Asn Glu Thr Asn Cys Val Tyr Met Asp Ile Gln
530                 535                 540 gat cag ttg cag tct gtg tgg aaa acc aag tca tgt ttt cag ccc tca          1680
Asp Gln Leu Gln Ser Val Trp Lys Thr Lys Ser Cys Phe Gln Pro Ser
545                 550                 555                 560 agt ttt gct tgc atg atg gat ctg tca gac aga aat aaa gcc aaa tgc          1728
Ser Phe Ala Cys Met Met Asp Leu Ser Asp Arg Asn Lys Ala Lys Cys
                565                 570                 575 gat gat cct gga tca ctg gaa aat gga cac gcc aca ctt cat gga caa          1776
Asp Asp Pro Gly Ser Leu Glu Asn Gly His Ala Thr Leu His Gly Gln
            580                 585                 590 agt att gat ggg ttc tat gct ggt tct tct ata agg tac agc tgt gag          1824
Ser Ile Asp Gly Phe Tyr Ala Gly Ser Ser Ile Arg Tyr Ser Cys Glu
            595                 600                 605 gtt ctc cac tac ctc agt gga act gaa acc gta act tgt aca aca aat          1872
Val Leu His Tyr Leu Ser Gly Thr Glu Thr Val Thr Cys Thr Thr Asn
            610                 615                 620 ggc aca tgg agt gct cct aaa cct cga tgt atc aaa gtc atc acc tgc          1920
Gly Thr Trp Ser Ala Pro Lys Pro Arg Cys Ile Lys Val Ile Thr Cys
625                 630                 635                 640 caa aac ccc cct gta cca tca tat ggt tct gtg gaa atc aaa ccc cca          1968
Gln Asn Pro Pro Val Pro Ser Tyr Gly Ser Val Glu Ile Lys Pro Pro
                645                 650                 655 agt cgg aca aac tcg ata agt cgt gtt ggg tca cct ttc ttg agg ttg          2016
Ser Arg Thr Asn Ser Ile Ser Arg Val Gly Ser Pro Phe Leu Arg Leu
            660                 665                 670 cca cgg tta ccc ctc cca tta gct aga gca gcc aaa cct cct cca aaa          2064
Pro Arg Leu Pro Leu Pro Leu Ala Arg Ala Ala Lys Pro Pro Pro Lys
            675                 680                 685 cct aga tcc tca caa ccc tct act gtg gac ttg gct tct aaa gtt aaa          2112
Pro Arg Ser Ser Gln Pro Ser Thr Val Asp Leu Ala Ser Lys Val Lys
690                 695                 700 cta cct gaa ggt cat tac cgg gta ggg tct cga gcc atc tac acg tgc          2160
Leu Pro Glu Gly His Tyr Arg Val Gly Ser Arg Ala Ile Tyr Thr Cys
705                 710                 715                 720 gag tcg aga tac tac gaa cta ctt gga tct caa ggc aga aga tgt gac          2208
Glu Ser Arg Tyr Tyr Glu Leu Leu Gly Ser Gln Gly Arg Arg Cys Asp
                725                 730                 735 tct aat gga aac tgg agt ggt cgg cca gcg agc tgt att cca gtt tgt          2256
Ser Asn Gly Asn Trp Ser Gly Arg Pro Ala Ser Cys Ile Pro Val Cys
            740                 745                 750 gga cgg tca gac tct cct cgt tct cct ttt atc tgg aat ggg aat tct          2304
Gly Arg Ser Asp Ser Pro Arg Ser Pro Phe Ile Trp Asn Gly Asn Ser
            755                 760                 765 aca gaa ata ggt cag tgg ccg tgg cag gca gga atc tct aga tgg ctt          2352
Thr Glu Ile Gly Gln Trp Pro Trp Gln Ala Gly Ile Ser Arg Trp Leu
770                 775                 780 gca gac cac aat atg tgg ttt ctc cag tgt gga gga tct cta ttg aat          2400
Ala Asp His Asn Met Trp Phe Leu Gln Cys Gly Gly Ser Leu Leu Asn
785                 790                 795                 800
```

| | | |
|---|---|---|
| gag aaa tgg atc gtc act gct gcc cac tgt gtc acc tac tct gct act<br>Glu Lys Trp Ile Val Thr Ala Ala His Cys Val Thr Tyr Ser Ala Thr<br>805 810 815 | | 2448 |
| gct gag att att gac ccc aat cag ttt aaa atg tat ctg ggc aag tac<br>Ala Glu Ile Ile Asp Pro Asn Gln Phe Lys Met Tyr Leu Gly Lys Tyr<br>820 825 830 | | 2496 |
| tac cgt gat gac agt aga gac gat gac tat gta caa gta aga gag gct<br>Tyr Arg Asp Asp Ser Arg Asp Asp Asp Tyr Val Gln Val Arg Glu Ala<br>835 840 845 | | 2544 |
| ctt gag atc cac gtg aat cct aac tac gac ccc ggc aat ctc aac ttt<br>Leu Glu Ile His Val Asn Pro Asn Tyr Asp Pro Gly Asn Leu Asn Phe<br>850 855 860 | | 2592 |
| gac ata gcc cta att caa ctg aaa act cct gtt act ttg aca aca cga<br>Asp Ile Ala Leu Ile Gln Leu Lys Thr Pro Val Thr Leu Thr Thr Arg<br>865 870 875 880 | | 2640 |
| gtc caa cca atc tgt ctg cct act gac atc aca aca aga gaa cac ttg<br>Val Gln Pro Ile Cys Leu Pro Thr Asp Ile Thr Thr Arg Glu His Leu<br>885 890 895 | | 2688 |
| aag gag gga aca tta gca gtg gtg aca ggt tgg ggt ttg aat gaa aac<br>Lys Glu Gly Thr Leu Ala Val Val Thr Gly Trp Gly Leu Asn Glu Asn<br>900 905 910 | | 2736 |
| aac acc tat tca gag acg att caa caa gct gtg cta cct gtt gtt gca<br>Asn Thr Tyr Ser Glu Thr Ile Gln Gln Ala Val Leu Pro Val Val Ala<br>915 920 925 | | 2784 |
| gcc agc acc tgt gaa gag ggg tac aag gaa gca gac tta cca ctg aca<br>Ala Ser Thr Cys Glu Glu Gly Tyr Lys Glu Ala Asp Leu Pro Leu Thr<br>930 935 940 | | 2832 |
| gta aca gag aac atg ttc tgt gca ggt tac aag aag gga cgt tat gat<br>Val Thr Glu Asn Met Phe Cys Ala Gly Tyr Lys Lys Gly Arg Tyr Asp<br>945 950 955 960 | | 2880 |
| gcc tgc agt ggg gac agt gga gga cct tta gtg ttt gct gat gat tcc<br>Ala Cys Ser Gly Asp Ser Gly Gly Pro Leu Val Phe Ala Asp Asp Ser<br>965 970 975 | | 2928 |
| cgt acc gaa agg cgg tgg gtc ttg gaa ggg att gtc agc tgg ggc agt<br>Arg Thr Glu Arg Arg Trp Val Leu Glu Gly Ile Val Ser Trp Gly Ser<br>980 985 990 | | 2976 |
| ccc agt gga tgt ggc aag gcg aac cag tac ggg ggc ttc act aaa gtt<br>Pro Ser Gly Cys Gly Lys Ala Asn Gln Tyr Gly Gly Phe Thr Lys Val<br>995 1000 1005 | | 3024 |
| aac gtt ttc ctg tca tgg att agg cag ttc att tga<br>Asn Val Phe Leu Ser Trp Ile Arg Gln Phe Ile<br>1010 1015 | | 3060 |

<210> SEQ ID NO 4
<211> LENGTH: 1019
<212> TYPE: PRT
<213> ORGANISM: Carcinoscorpius rotundicauda
<400> SEQUENCE: 4

Met Val Leu Ala Ser Phe Leu Val Ser Gly Leu Val Leu Gly Leu Leu
1               5                   10                  15

Ala Gln Lys Met Arg Pro Val Gln Ser Lys Gly Val Asp Leu Gly Leu
            20                  25                  30

Cys Asp Glu Thr Arg Phe Glu Cys Lys Cys Gly Asp Pro Gly Tyr Val
        35                  40                  45

Phe Asn Ile Pro Val Lys Gln Cys Thr Tyr Phe Tyr Arg Trp Arg Pro
    50                  55                  60

Tyr Cys Lys Pro Cys Asp Asp Leu Glu Ala Lys Asp Ile Cys Pro Lys
65                  70                  75                  80

-continued

```
Tyr Lys Arg Cys Gln Glu Cys Lys Ala Gly Leu Asp Ser Cys Val Thr
                85                  90                  95
Cys Pro Pro Asn Lys Tyr Gly Thr Trp Cys Ser Gly Glu Cys Gln Cys
            100                 105                 110
Lys Asn Gly Gly Ile Cys Asp Gln Arg Thr Gly Ala Cys Ala Cys Arg
        115                 120                 125
Asp Arg Tyr Glu Gly Val His Cys Glu Ile Leu Lys Gly Cys Pro Leu
130                 135                 140
Leu Pro Ser Asp Ser Gln Val Gln Glu Val Arg Asn Pro Pro Asp Asn
145                 150                 155                 160
Pro Gln Thr Ile Asp Tyr Ser Cys Ser Pro Gly Phe Lys Leu Lys Gly
                165                 170                 175
Met Ala Arg Ile Ser Cys Leu Pro Asn Gly Gln Trp Ser Asn Phe Pro
            180                 185                 190
Pro Lys Cys Ile Arg Glu Cys Ala Met Val Ser Ser Pro Glu His Gly
        195                 200                 205
Lys Val Asn Ala Leu Ser Gly Asp Met Ile Glu Gly Ala Thr Leu Arg
210                 215                 220
Phe Ser Cys Asp Ser Pro Tyr Tyr Leu Ile Gly Gln Glu Thr Leu Thr
225                 230                 235                 240
Cys Gln Gly Asn Gly Gln Trp Asn Gly Gln Ile Pro Gln Cys Lys Asn
                245                 250                 255
Leu Val Phe Cys Pro Asp Leu Asp Pro Val Asn His Ala Glu His Lys
            260                 265                 270
Val Lys Ile Gly Val Glu Gln Lys Tyr Gly Gln Phe Pro Gln Gly Thr
        275                 280                 285
Glu Val Thr Tyr Thr Cys Ser Gly Asn Tyr Phe Leu Met Gly Phe Asp
290                 295                 300
Thr Leu Lys Cys Asn Pro Asp Gly Ser Trp Ser Gly Ser Gln Pro Ser
305                 310                 315                 320
Cys Val Lys Val Ala Asp Arg Glu Val Asp Cys Asp Ser Lys Ala Val
                325                 330                 335
Asp Phe Leu Asp Asp Val Gly Glu Pro Val Arg Ile His Cys Pro Ala
            340                 345                 350
Gly Cys Ser Leu Thr Ala Gly Thr Val Trp Gly Thr Ala Ile Tyr His
        355                 360                 365
Glu Leu Ser Ser Val Cys Arg Ala Ala Ile His Ala Gly Lys Leu Pro
370                 375                 380
Asn Ser Gly Gly Ala Val His Val Val Asn Asn Gly Pro Tyr Ser Asp
385                 390                 395                 400
Phe Leu Gly Ser Asp Leu Asn Gly Ile Lys Ser Glu Glu Leu Lys Ser
                405                 410                 415
Leu Ala Arg Ser Phe Arg Phe Asp Tyr Val Arg Ser Ser Thr Ala Gly
            420                 425                 430
Lys Ser Gly Cys Pro Asp Gly Trp Phe Glu Val Asp Glu Asn Cys Val
        435                 440                 445
Tyr Val Thr Ser Lys Gln Arg Ala Trp Glu Arg Ala Gln Gly Val Cys
450                 455                 460
Thr Asn Met Ala Ala Arg Leu Ala Val Leu Asp Lys Asp Val Ile Pro
465                 470                 475                 480
Asn Ser Leu Thr Glu Thr Leu Arg Gly Lys Gly Leu Thr Thr Thr Trp
                485                 490                 495
Ile Gly Leu His Arg Leu Asp Ala Glu Lys Pro Phe Ile Trp Glu Leu
```

```
                500             505             510
Met Asp Arg Ser Asn Val Val Leu Asn Asp Asn Leu Thr Phe Trp Ala
            515             520             525

Ser Gly Glu Pro Gly Asn Glu Thr Asn Cys Val Tyr Met Asp Ile Gln
            530             535             540

Asp Gln Leu Gln Ser Val Trp Lys Thr Lys Ser Cys Phe Gln Pro Ser
545             550             555             560

Ser Phe Ala Cys Met Met Asp Leu Ser Asp Arg Asn Lys Ala Lys Cys
                565             570             575

Asp Asp Pro Gly Ser Leu Glu Asn Gly His Ala Thr Leu His Gly Gln
            580             585             590

Ser Ile Asp Gly Phe Tyr Ala Gly Ser Ser Ile Arg Tyr Ser Cys Glu
            595             600             605

Val Leu His Tyr Leu Ser Gly Thr Glu Thr Val Thr Cys Thr Thr Asn
            610             615             620

Gly Thr Trp Ser Ala Pro Lys Pro Arg Cys Ile Lys Val Ile Thr Cys
625             630             635             640

Gln Asn Pro Pro Val Pro Ser Tyr Gly Ser Val Glu Ile Lys Pro Pro
                645             650             655

Ser Arg Thr Asn Ser Ile Ser Arg Val Gly Ser Pro Phe Leu Arg Leu
            660             665             670

Pro Arg Leu Pro Leu Pro Leu Ala Arg Ala Lys Pro Pro Lys
            675             680             685

Pro Arg Ser Ser Gln Pro Ser Thr Val Asp Leu Ala Ser Lys Val Lys
            690             695             700

Leu Pro Glu Gly His Tyr Arg Val Gly Ser Arg Ala Ile Tyr Thr Cys
705             710             715             720

Glu Ser Arg Tyr Tyr Glu Leu Leu Gly Ser Gln Gly Arg Arg Cys Asp
                725             730             735

Ser Asn Gly Asn Trp Ser Gly Arg Pro Ala Ser Cys Ile Pro Val Cys
            740             745             750

Gly Arg Ser Asp Ser Pro Arg Ser Pro Phe Ile Trp Asn Gly Asn Ser
            755             760             765

Thr Glu Ile Gly Gln Trp Pro Trp Gln Ala Gly Ile Ser Arg Trp Leu
            770             775             780

Ala Asp His Asn Met Trp Phe Leu Gln Cys Gly Gly Ser Leu Leu Asn
785             790             795             800

Glu Lys Trp Ile Val Thr Ala Ala His Cys Val Thr Tyr Ser Ala Thr
                805             810             815

Ala Glu Ile Ile Asp Pro Asn Gln Phe Lys Met Tyr Leu Gly Lys Tyr
            820             825             830

Tyr Arg Asp Asp Ser Arg Asp Asp Tyr Val Gln Val Arg Glu Ala
            835             840             845

Leu Glu Ile His Val Asn Pro Asn Tyr Asp Pro Gly Asn Leu Asn Phe
            850             855             860

Asp Ile Ala Leu Ile Gln Leu Lys Thr Pro Val Thr Leu Thr Thr Arg
865             870             875             880

Val Gln Pro Ile Cys Leu Pro Thr Asp Ile Thr Thr Arg Glu His Leu
                885             890             895

Lys Glu Gly Thr Leu Ala Val Val Thr Gly Trp Gly Leu Asn Glu Asn
            900             905             910

Asn Thr Tyr Ser Glu Thr Ile Gln Gln Ala Val Leu Pro Val Val Ala
            915             920             925
```

```
Ala Ser Thr Cys Glu Glu Gly Tyr Lys Glu Ala Asp Leu Pro Leu Thr
    930                 935                 940

Val Thr Glu Asn Met Phe Cys Ala Gly Tyr Lys Lys Gly Arg Tyr Asp
945                 950                 955                 960

Ala Cys Ser Gly Asp Ser Gly Gly Pro Leu Val Phe Ala Asp Asp Ser
                965                 970                 975

Arg Thr Glu Arg Arg Trp Val Leu Glu Gly Ile Val Ser Trp Gly Ser
            980                 985                 990

Pro Ser Gly Cys Gly Lys Ala Asn  Gln Tyr Gly Gly Phe  Thr Lys Val
        995                 1000                1005

Asn Val  Phe Leu Ser Trp Ile  Arg Gln Phe Ile
    1010                 1015
```

```
<210> SEQ ID NO 5
<211> LENGTH: 1203
<212> TYPE: DNA
<213> ORGANISM: Tachypleus tridentatus
<220> FEATURE:
<221> NAME/KEY: CDS
<222> LOCATION: (1)..(1203)

<400> SEQUENCE: 5
```

```
atg acg tgg ata tgt gtg ata acg ttg ttt gct ctg gct tct gct acg      48
Met Thr Trp Ile Cys Val Ile Thr Leu Phe Ala Leu Ala Ser Ala Thr
1               5                   10                  15 ttg ggt aac aaa gtt agt aga gtg ggg gtc ctc ttc ccc aag aca cgg      96
Leu Gly Asn Lys Val Ser Arg Val Gly Val Leu Phe Pro Lys Thr Arg
                20                  25                  30 aac gac aat gag tgt aca gca aga ggg gga ttg aaa gga tcc tgc aaa     144
Asn Asp Asn Glu Cys Thr Ala Arg Gly Gly Leu Lys Gly Ser Cys Lys
            35                  40                  45 tcc ctc ata gac tgt cct agt gtc ttg gct acg ttg aag gac agt ttt     192
Ser Leu Ile Asp Cys Pro Ser Val Leu Ala Thr Leu Lys Asp Ser Phe
        50                  55                  60 cct gtc gtt tgc tct tgg aat ggt cga ttt cag cct att gtc tgc tgt     240
Pro Val Val Cys Ser Trp Asn Gly Arg Phe Gln Pro Ile Val Cys Cys
65                  70                  75                  80 cct gat gca ata gca cca cca cct gta acc aca aca gct gta act gta     288
Pro Asp Ala Ile Ala Pro Pro Pro Val Thr Thr Thr Ala Val Thr Val
                85                  90                  95 ata tct aca aaa gaa cca aag ctt cca aga tta cat ata tca ggt tgt     336
Ile Ser Thr Lys Glu Pro Lys Leu Pro Arg Leu His Ile Ser Gly Cys
                100                 105                 110 gga aaa aga aaa gtc aaa ata gat att aca act gtt gga cgc tct gga     384
Gly Lys Arg Lys Val Lys Ile Asp Ile Thr Thr Val Gly Arg Ser Gly
            115                 120                 125 tca cca ata ctt cct ccg ata tct act cct caa aat tca aca ggt ggg     432
Ser Pro Ile Leu Pro Pro Ile Ser Thr Pro Gln Asn Ser Thr Gly Gly
        130                 135                 140 aga gga att att gct gga ggc gta gaa gcc aaa att ggc gcg tgg cct     480
Arg Gly Ile Ile Ala Gly Gly Val Glu Ala Lys Ile Gly Ala Trp Pro
145                 150                 155                 160 tgg atg gca gct gtt ttt gtg aaa aac ttt ggc att ggc aga ttc cac     528
Trp Met Ala Ala Val Phe Val Lys Asn Phe Gly Ile Gly Arg Phe His
                165                 170                 175 tgt gct ggt agc ata atc agt aac aag tac att ttg tca gct gcc cac     576
Cys Ala Gly Ser Ile Ile Ser Asn Lys Tyr Ile Leu Ser Ala Ala His
                180                 185                 190 gcc ttc ctt atc gga ggt cga aag ttg acc cca act cgc tta gct gtc     624
```

```
                Ala Phe Leu Ile Gly Gly Arg Lys Leu Thr Pro Thr Arg Leu Ala Val
                            195                 200                 205 cgt gtg gga ggc cac tac ata aag agg ggt caa gag tat cca gtg aaa                672
Arg Val Gly Gly His Tyr Ile Lys Arg Gly Gln Glu Tyr Pro Val Lys
210                 215                 220 gac gtg att atc cat cct cat tat gta gaa aag gag aac tac aat gat                720
Asp Val Ile Ile His Pro His Tyr Val Glu Lys Glu Asn Tyr Asn Asp
225                 230                 235                 240 ata gcc ata atc gag tta aaa gag gaa ctg aac ttt acg gac ttg gtc                768
Ile Ala Ile Ile Glu Leu Lys Glu Glu Leu Asn Phe Thr Asp Leu Val
                245                 250                 255 aat cct ata tgt ctc cct gat cca gag aca gta acg gat cca tta aaa                816
Asn Pro Ile Cys Leu Pro Asp Pro Glu Thr Val Thr Asp Pro Leu Lys
            260                 265                 270 gac aga att gtg act gca gcg gga tgg ggc gat ctg gat ttc tcc ggt                864
Asp Arg Ile Val Thr Ala Ala Gly Trp Gly Asp Leu Asp Phe Ser Gly
        275                 280                 285 cca cgg agc caa gtt cta cgt gag gta agc atc cca gtt gtt cca gtt                912
Pro Arg Ser Gln Val Leu Arg Glu Val Ser Ile Pro Val Val Pro Val
290                 295                 300 gat aaa tgt gat caa gcc tat gag aaa ctc aac acc cct tca cta aaa                960
Asp Lys Cys Asp Gln Ala Tyr Glu Lys Leu Asn Thr Pro Ser Leu Lys
305                 310                 315                 320 aat ggg ata acg aat aac ttc ctt tgc gct gga ttg gaa gaa gga ggg                1008
Asn Gly Ile Thr Asn Asn Phe Leu Cys Ala Gly Leu Glu Glu Gly Gly
                325                 330                 335 aaa gac gct tgc caa ggc gat tct ggt gga ccg ttg atg cta gtg aac                1056
Lys Asp Ala Cys Gln Gly Asp Ser Gly Gly Pro Leu Met Leu Val Asn
            340                 345                 350 aac act agg tgg ata gta gta gga gtt gtg tcg ttc ggg cac aag tgt                1104
Asn Thr Arg Trp Ile Val Val Gly Val Val Ser Phe Gly His Lys Cys
        355                 360                 365 gcc gag gaa gga tat cct ggt gtg tac tcg cgc gta gcg agt tac cta                1152
Ala Glu Glu Gly Tyr Pro Gly Val Tyr Ser Arg Val Ala Ser Tyr Leu
370                 375                 380 gac tgg atc gcg aaa gtt acg aac tcg tta gat cat gcc gtc act aac                1200
Asp Trp Ile Ala Lys Val Thr Asn Ser Leu Asp His Ala Val Thr Asn
385                 390                 395                 400 taa                                                                            1203

<210> SEQ ID NO 6
<211> LENGTH: 400
<212> TYPE: PRT
<213> ORGANISM: Tachypleus tridentatus

<400> SEQUENCE: 6

Met Thr Trp Ile Cys Val Ile Thr Leu Phe Ala Leu Ala Ser Ala Thr
1               5                   10                  15

Leu Gly Asn Lys Val Ser Arg Val Gly Val Leu Phe Pro Lys Thr Arg
            20                  25                  30

Asn Asp Asn Glu Cys Thr Ala Arg Gly Gly Leu Lys Gly Ser Cys Lys
        35                  40                  45

Ser Leu Ile Asp Cys Pro Ser Val Leu Ala Thr Leu Lys Asp Ser Phe
    50                  55                  60

Pro Val Val Cys Ser Trp Asn Gly Arg Phe Gln Pro Ile Val Cys Cys
65                  70                  75                  80

Pro Asp Ala Ile Ala Pro Pro Pro Val Thr Thr Thr Ala Val Thr Val
                85                  90                  95
```

```
Ile Ser Thr Lys Glu Pro Lys Leu Pro Arg Leu His Ile Ser Gly Cys
            100                 105                 110

Gly Lys Arg Lys Val Lys Ile Asp Ile Thr Thr Val Gly Arg Ser Gly
        115                 120                 125

Ser Pro Ile Leu Pro Pro Ile Ser Thr Pro Gln Asn Ser Thr Gly Gly
    130                 135                 140

Arg Gly Ile Ile Ala Gly Gly Val Glu Ala Lys Ile Gly Ala Trp Pro
145                 150                 155                 160

Trp Met Ala Ala Val Phe Val Lys Asn Phe Gly Ile Gly Arg Phe His
                165                 170                 175

Cys Ala Gly Ser Ile Ile Ser Asn Lys Tyr Ile Leu Ser Ala Ala His
            180                 185                 190

Ala Phe Leu Ile Gly Gly Arg Lys Leu Thr Pro Thr Arg Leu Ala Val
        195                 200                 205

Arg Val Gly Gly His Tyr Ile Lys Arg Gly Gln Glu Tyr Pro Val Lys
    210                 215                 220

Asp Val Ile Ile His Pro His Tyr Val Glu Lys Glu Asn Tyr Asn Asp
225                 230                 235                 240

Ile Ala Ile Ile Glu Leu Lys Glu Leu Asn Phe Thr Asp Leu Val
                245                 250                 255

Asn Pro Ile Cys Leu Pro Asp Pro Glu Thr Val Thr Asp Pro Leu Lys
            260                 265                 270

Asp Arg Ile Val Thr Ala Ala Gly Trp Gly Asp Leu Asp Phe Ser Gly
        275                 280                 285

Pro Arg Ser Gln Val Leu Arg Glu Val Ser Ile Pro Val Val Pro Val
    290                 295                 300

Asp Lys Cys Asp Gln Ala Tyr Glu Lys Leu Asn Thr Pro Ser Leu Lys
305                 310                 315                 320

Asn Gly Ile Thr Asn Asn Phe Leu Cys Ala Gly Leu Glu Glu Gly Gly
                325                 330                 335

Lys Asp Ala Cys Gln Gly Asp Ser Gly Gly Pro Leu Met Leu Val Asn
            340                 345                 350

Asn Thr Arg Trp Ile Val Val Gly Val Val Ser Phe Gly His Lys Cys
        355                 360                 365

Ala Glu Glu Gly Tyr Pro Gly Val Tyr Ser Arg Val Ala Ser Tyr Leu
    370                 375                 380

Asp Trp Ile Ala Lys Val Thr Asn Ser Leu Asp His Ala Val Thr Asn
385                 390                 395                 400

<210> SEQ ID NO 7
<211> LENGTH: 1128
<212> TYPE: DNA
<213> ORGANISM: Tachypleus tridentatus
<220> FEATURE:
<221> NAME/KEY: CDS
<222> LOCATION: (1)..(1128)

<400> SEQUENCE: 7 atg ttg gtg aat aac gtg ttt tca cta ctg tgt ttc cca ctc ttg atg      48
Met Leu Val Asn Asn Val Phe Ser Leu Leu Cys Phe Pro Leu Leu Met
1               5                   10                  15 tct gtg gtt aga tgc agt act ctc agc aga cag cgt aga cag ttt gtt      96
Ser Val Val Arg Cys Ser Thr Leu Ser Arg Gln Arg Arg Gln Phe Val
                20                  25                  30 ttc cct gac gag gaa gaa ctt tgc tca aac cga ttt act gaa gaa gga     144
Phe Pro Asp Glu Glu Glu Leu Cys Ser Asn Arg Phe Thr Glu Glu Gly
            35                  40                  45
```

```
aca tgc aaa aat gtc ttg gat tgt aga ata ctt tta caa aaa aat gat      192
Thr Cys Lys Asn Val Leu Asp Cys Arg Ile Leu Leu Gln Lys Asn Asp
     50              55                  60 tat aat tta ctc aaa gaa tca ata tgc ggc ttt gaa ggc ata aca ccc      240
Tyr Asn Leu Leu Lys Glu Ser Ile Cys Gly Phe Glu Gly Ile Thr Pro
65              70                  75                  80 aaa gtt tgt tgt ccg aaa tca agc cat gta att tca agt aca cag gca      288
Lys Val Cys Cys Pro Lys Ser Ser His Val Ile Ser Ser Thr Gln Ala
                 85                  90                  95 cct cca gaa acc act acg act gaa cgc cca cca aaa cag ata cca ccc      336
Pro Pro Glu Thr Thr Thr Thr Glu Arg Pro Pro Lys Gln Ile Pro Pro
            100                 105                 110 aat ctt cat gaa gtg tgt gga att cac aat act aca act acc agg att      384
Asn Leu His Glu Val Cys Gly Ile His Asn Thr Thr Thr Thr Arg Ile
        115                 120                 125 att gga ggt cgg gaa gca cct att gga gcc tgg ccg tgg atg act gct      432
Ile Gly Gly Arg Glu Ala Pro Ile Gly Ala Trp Pro Trp Met Thr Ala
130                 135                 140 gtc tac ata aaa caa gga gga atc aga agt gtt cag tgt ggt ggc gca      480
Val Tyr Ile Lys Gln Gly Gly Ile Arg Ser Val Gln Cys Gly Gly Ala
145             150                 155                 160 ctt gtc act aac agg cac gtg att aca gct tcg cac tgt gtt gta aac      528
Leu Val Thr Asn Arg His Val Ile Thr Ala Ser His Cys Val Val Asn
                165                 170                 175 agt gca gga aca gat gtg atg cca gct gat gta ttc tcg gtt cgt ctg      576
Ser Ala Gly Thr Asp Val Met Pro Ala Asp Val Phe Ser Val Arg Leu
            180                 185                 190 ggt gaa cac aat tta tac agt acc gat gac gat tcg aat cca ata gat      624
Gly Glu His Asn Leu Tyr Ser Thr Asp Asp Asp Ser Asn Pro Ile Asp
        195                 200                 205 ttt gca gtt acg tcg gtg aaa cat cac gaa cac ttt gta ctc gcg acg      672
Phe Ala Val Thr Ser Val Lys His His Glu His Phe Val Leu Ala Thr
210                 215                 220 tat ttg aat gac atc gca att cta acg tta aat gac aca gtt acg ttt      720
Tyr Leu Asn Asp Ile Ala Ile Leu Thr Leu Asn Asp Thr Val Thr Phe
225             230                 235                 240 aca gac aga att cga ccc att tgt cta cct tat cgt aag ttg aga tac      768
Thr Asp Arg Ile Arg Pro Ile Cys Leu Pro Tyr Arg Lys Leu Arg Tyr
                245                 250                 255 gat gat cta gca atg aga aaa ccg ttt atc act gga tgg gga aca aca      816
Asp Asp Leu Ala Met Arg Lys Pro Phe Ile Thr Gly Trp Gly Thr Thr
            260                 265                 270 gca ttt aac ggc cca tct agt gca gtg ttg aga gaa gta cag tta cca      864
Ala Phe Asn Gly Pro Ser Ser Ala Val Leu Arg Glu Val Gln Leu Pro
        275                 280                 285 ata tgg gaa cac gag gcc tgt aga cag gcc tac gag aag gat tta aat      912
Ile Trp Glu His Glu Ala Cys Arg Gln Ala Tyr Glu Lys Asp Leu Asn
290                 295                 300 att aca aac gtg tat atg tgt gct ggc ttt gca gat ggc ggg aag gat      960
Ile Thr Asn Val Tyr Met Cys Ala Gly Phe Ala Asp Gly Gly Lys Asp
305             310                 315                 320 gct tgc cag ggt gat tct gga ggt cca atg atg ttg cct gtt aaa acc     1008
Ala Cys Gln Gly Asp Ser Gly Gly Pro Met Met Leu Pro Val Lys Thr
                325                 330                 335 gga gag ttt tat ctc att gga att gtg tct ttc gga aag aaa tgc gca     1056
Gly Glu Phe Tyr Leu Ile Gly Ile Val Ser Phe Gly Lys Lys Cys Ala
            340                 345                 350 ttg cct gga ttt cct ggg gtt tac aca aaa gtg aca gag ttt tta gat     1104
Leu Pro Gly Phe Pro Gly Val Tyr Thr Lys Val Thr Glu Phe Leu Asp
```

```
                355                 360                 365
tgg att gca gaa cat atg gtg tag                                      1128
Trp Ile Ala Glu His Met Val
    370                 375

<210> SEQ ID NO 8
<211> LENGTH: 375
<212> TYPE: PRT
<213> ORGANISM: Tachypleus tridentatus

<400> SEQUENCE: 8

Met Leu Val Asn Asn Val Phe Ser Leu Leu Cys Phe Pro Leu Leu Met
1               5                   10                  15

Ser Val Val Arg Cys Ser Thr Leu Ser Arg Gln Arg Gln Phe Val
            20                  25                  30

Phe Pro Asp Glu Glu Leu Cys Ser Asn Arg Phe Thr Glu Glu Gly
        35                  40                  45

Thr Cys Lys Asn Val Leu Asp Cys Arg Ile Leu Leu Gln Lys Asn Asp
    50                  55                  60

Tyr Asn Leu Leu Lys Glu Ser Ile Cys Gly Phe Glu Gly Ile Thr Pro
65                  70                  75                  80

Lys Val Cys Cys Pro Lys Ser Ser His Val Ile Ser Ser Thr Gln Ala
                85                  90                  95

Pro Pro Glu Thr Thr Thr Thr Glu Arg Pro Pro Lys Gln Ile Pro Pro
            100                 105                 110

Asn Leu His Glu Val Cys Gly Ile His Asn Thr Thr Thr Arg Ile
        115                 120                 125

Ile Gly Gly Arg Glu Ala Pro Ile Gly Ala Trp Pro Trp Met Thr Ala
130                 135                 140

Val Tyr Ile Lys Gln Gly Gly Ile Arg Ser Val Gln Cys Gly Gly Ala
145                 150                 155                 160

Leu Val Thr Asn Arg His Val Ile Thr Ala Ser His Cys Val Val Asn
                165                 170                 175

Ser Ala Gly Thr Asp Val Met Pro Ala Asp Val Phe Ser Val Arg Leu
            180                 185                 190

Gly Glu His Asn Leu Tyr Ser Thr Asp Asp Ser Asn Pro Ile Asp
        195                 200                 205

Phe Ala Val Thr Ser Val Lys His His Glu His Phe Val Leu Ala Thr
210                 215                 220

Tyr Leu Asn Asp Ile Ala Ile Leu Thr Leu Asn Asp Thr Val Thr Phe
225                 230                 235                 240

Thr Asp Arg Ile Arg Pro Ile Cys Leu Pro Tyr Arg Lys Leu Arg Tyr
                245                 250                 255

Asp Asp Leu Ala Met Arg Lys Pro Phe Ile Thr Gly Trp Gly Thr Thr
            260                 265                 270

Ala Phe Asn Gly Pro Ser Ser Ala Val Leu Arg Glu Val Gln Leu Pro
        275                 280                 285

Ile Trp Glu His Glu Ala Cys Arg Gln Ala Tyr Glu Lys Asp Leu Asn
290                 295                 300

Ile Thr Asn Val Tyr Met Cys Ala Gly Phe Ala Asp Gly Gly Lys Asp
305                 310                 315                 320

Ala Cys Gln Gly Asp Ser Gly Gly Pro Met Met Leu Pro Val Lys Thr
                325                 330                 335

Gly Glu Phe Tyr Leu Ile Gly Ile Val Ser Phe Gly Lys Lys Cys Ala
            340                 345                 350
```

Leu Pro Gly Phe Pro Gly Val Tyr Thr Lys Val Thr Glu Phe Leu Asp
    355                 360                 365

Trp Ile Ala Glu His Met Val
    370                 375

<210> SEQ ID NO 9
<211> LENGTH: 1203
<212> TYPE: DNA
<213> ORGANISM: Tachypleus tridentatus

<400> SEQUENCE: 9

| | | | |
|---|---|---|---|
| atgacctgga tctgcgtgat caccctgttc gctctggctt ccgctaccct gggcaacaag | 60 |
| gtgtcccgtg tgggtgtcct gttccccaag acccgtaacg acaacgagtg caccgctcgt | 120 |
| ggtggtctga aggctcctg caagtccctg atcgactgcc cctccgtgct ggctaccctg | 180 |
| aaggactcct tccccgtcgt gtgctcctgg aacggtcgtt ccagcccat cgtgtgctgc | 240 |
| cccgacgcta tcgctccccc ccctgtgacc accaccgctg tgaccgtgat ctccaccaag | 300 |
| gagcccaagc tgccccgtct gcacatctcc ggttgcggca gcgcaaggt caagatcgac | 360 |
| atcaccaccg tgggccgttc cggttccccc atcctgcccc ccatctccac ccccagaac | 420 |
| tccactggtg gtcgtggtat catcgctggc ggtgtcgagg ctaagatcgg tgcttggccc | 480 |
| tggatggctg ctgtgttcgt gaagaacttc ggtatcggtc gcttccactg cgctggttcc | 540 |
| atcatctcca acaagtacat cctgtccgct gctcacgctt tcctcatcgg tggtcgcaag | 600 |
| ctgaccccca cccgtctggc tgtgcgtgtg ggtggtcact acatcaagcg tggccaggag | 660 |
| taccccgtca aggacgtgat catccacccc cactacgtgg agaaggagaa ctacaacgac | 720 |
| atcgccatca tcgagctgaa ggaggagctg aacttcaccg acctggtcaa ccccatctgc | 780 |
| ctgcccgacc ccgagactgt gaccgaccct ctgaaggacc gtatcgtgac cgctgctggc | 840 |
| tggggcgacc tggacttctc cggtcccccgt tcccaggtgc tgcgtgaggt gtccatcccc | 900 |
| gtggtgcccg tggacaagtg cgaccaggct tacgagaagc tgaacacccc ctccctgaag | 960 |
| aacggtatta ccaacaactt cctctgcgcc ggactcgagg agggtggcaa ggacgcttgc | 1020 |
| cagggcgact ccggtggtcc cctgatgctg gtcaacaaca cccgttggat cgtcgtgggt | 1080 |
| gtcgtgtcct tcggtcacaa gtgcgctgag gagggttacc ccggcgtcta ctcccgtgtg | 1140 |
| gcttcctacc tggactggat cgctaaggtc accaactccc tggaccacgc tgtcaccaac | 1200 |
| taa | 1203 |

<210> SEQ ID NO 10
<211> LENGTH: 4
<212> TYPE: PRT
<213> ORGANISM: Artificial Sequence
<220> FEATURE:
<223> OTHER INFORMATION: Synthetic peptide

<400> SEQUENCE: 10

Ile Glu Gly Arg
1

RECOMBINANT FACTOR C AND METHOD FOR PRODUCING THE SAME, AND METHOD FOR MEASURING ENDOTOXIN

CROSS-REFERENCE TO RELATED APPLICATIONS

This is a Continuation of U.S. patent application Ser. No. 15/983,725 filed May 18, 2018; which is a continuation of U.S. patent application Ser. No. 14/650,767 filed Jun. 9, 2015, now U.S. Pat. No. 10,144,923, which is National Stage of International Application No. PCT/JP2013/083082 filed Dec. 10, 2013, claiming priority based on Japanese Patent Application No. 2012-269840 filed Dec. 10, 2012, the contents of all of which are incorporated herein by reference in their entirety.

TECHNICAL FIELD

The present invention relates to a novel recombinant Factor C, to a method for producing the recombinant Factor C, and to a method for measuring endotoxin.

BACKGROUND ART

Endotoxin is a lipopolysaccharide which is present in the outer membrane of Gram-negative bacteria and is known as a strong pyrogen. It is also known that even a very small amount of endotoxin causes various pathological conditions via bacterial infection. Such conditions include not only fever but also release of an inflammatory cytokine concomitant with activation of macrophages, induction of endotoxin shock, and the like. Therefore, detection of endotoxin is essential in pharmaceutical products such as an injection, water, medical devices, and the like. From another aspect, endotoxin is a conceivable main cause for a shock involved in an infection with a Gram-negative bacterium. Thus, the presence of infection and a therapeutic effect can be determined through a blood endotoxin analysis.

Meanwhile, it has been known that the American horseshoe crab (*Limulus polyphemus*) undergoes blood clotting when it is infected with a Gram-negative bacterium. This phenomenon has been conventionally employed for the detection of endotoxin.

Specifically, there is known a method for measuring endotoxin by use of a hematocyte extract of a horseshoe crab (i.e. an amebocyte lysate of a horseshoe crab, hereinafter also referred to simply as a lysate) (see, for example, Non-Patent Document 1). This method is called a "limulus test," which employs a cascade reaction of a variety of proteins present in the lysate, which reaction occurs via contact between endotoxin and the lysate. FIG. 1 shows the scheme of the cascade reaction.

When endotoxin comes into contact with the lysate, Factor C, which is a serine protease zymogen present in the lysate, is activated to thereby form activated Factor C. The thus-formed activated Factor C activates Factor B present in the lysate, to thereby form activated Factor B. The thus-formed activated Factor B activates Pro-clotting enzyme present in the lysate, to thereby form a corresponding Clotting enzyme.

The Clotting enzyme hydrolyzes a specific site of a coagulogen molecule present in the lysate, thereby coagulin gel is formed, and thus the lysate is coagulated. Thus, endotoxin can be measured through measuring the lysate coagulation reaction.

Alternatively, endotoxin may also be measured through coloring reaction between the Clotting enzyme and a synthetic substrate. For example, the Clotting enzyme acts on t-butoxycarbonyl-leucyl-glycyl-arginyl-pNA (Boc-Leu-Gly-Arg-pNA), which is a synthetic substrate, to hydrolyze the amino bonds thereof, and thereby pNA is released. Thus, when the synthetic substrate has been added to the reaction system, endotoxin can be measured through measuring the absorbance (at 405 nm) of the coloring substance (pNA).

Furthermore, it is known that a cascade reaction system can be reconstituted by use of Factor C, Factor B, and Pro-clotting enzyme, which are purified from a lysate of the Japanese horseshoe crab (Non-Patent Document 2).

However, for using such a lysate, or Factor C, Factor B, and Pro-clotting enzyme purified from the lysate, horseshoe crabs must be caught and blood must be recovered there from. Hence, from the viewpoint of protection of biological resources, difficulty is encountered in supply of such ingredients in an inexhaustible manner. Under such circumstances, there is demand for a technique that can produce these ingredients by genetic engineering, to thereby reconstitute a cascade reaction system.

For example, there is known a case where Factor C, Factor B, and Pro-clotting enzyme were expressed in insect cells as host cells, to thereby reconstitute a cascade reaction system (Patent Documents 1 and 2). However, it has been reported that since the reconstituted system contains sodium chloride, magnesium sulfate, or calcium chloride in the reaction system, the cascade reaction is suppressed (Patent Document 1).

Alternatively, there is known a case of using mammalian cells as host cells, wherein Factor C derived from the Singaporean horseshoe crab (*Carcinoscorpius rotundicauda*) was expressed in COS-1, which is a cell line derived from African green monkey kidney cells, as host cells. However, it has been reported that when COS-1 was used as a host, the expressed Factor C was insoluble (Non-Patent Documents 3 and 4). That is, there has never been known a case where functional Factor C is produced using mammalian cells as host cells.

PRIOR ART DOCUMENTS

Patent Documents

Patent Document 1: WO 2008/004674, pamphlet
Patent Document 2: WO 2012/118226, pamphlet Non-Patent Documents Non-Patent Document 1: Iwanaga S., Curr. Opin. Immunol. February; 5(1): 74-82 (1993)
Non-Patent Document 2: Nakamura T., et al., J. Biochem. March; 99(3): 847-57 (1986)
Non-Patent Document 3: Roopashree S. Dwarakanath, et al., Biotechnology letters 19(4): 357-361 (1997)
Non-Patent Document 4: Jing Wang, Bow Ho and Jeak L. Ding, Biotechnology letters 23: 71-76 (2001)

SUMMARY OF THE INVENTION

Problems to be Solved by the Invention

An object of the present invention is to provide a novel recombinant horseshoe crab Factor C, and a method for producing the recombinant Factor C.

Meanwhile, injections to be administered in vivo generally contain a variety of salts (ions). In production of such injections, detection of endotoxin is obligated by the pharmacopoeia of the relevant country. Under such circumstances, in an aspect, another object of the present invention is to provide a reconstituted cascade reaction system which is not susceptible to reaction inhibition even in the presence of a salt (ion).

Means for Solving the Problems

The present inventors have found that a recombinant horseshoe crab Factor C can be produced by use of human cells or Chinese hamster cells as host cells, and that endotoxin can be measured by use of the thus-produced recombinant Factor C while reaction inhibition in the presence of a salt (ion) is mitigated. The present invention has been accomplished on the basis of these findings.

Accordingly, the present invention encompasses the following modes.

[1]
A horseshoe crab Factor C having activity of Factor C.
[1.1.1]
The above-described Factor C, which contains sialic acid.
[1.1.2]
The above-described Factor C, which contains ($\alpha$-2,3) linked terminal sialic acid.
[1.1.3]
The above-described Factor C, which contains ($\alpha$-2,3) linked terminal sialic acid in a greater amount, as compared with a native Factor C.
[1.1.4]
The above-described Factor C, which contains ($\alpha$-2,3) linked terminal sialic acid in a greater amount, as compared with a horseshoe crab Factor C expressed in Sf9 as a host cell.
[1.1.5]
The above-described Factor C, which exhibits a higher reactivity in lectin blotting by use of *Maackia amurensis* agglutinin, as compared with a native Factor C.
[1.1.6]
The above-described Factor C, which exhibits a higher reactivity in lectin blotting by use of *Maackia amurensis* agglutinin, as compared with a horseshoe crab Factor C expressed in Sf9 as a host cell.
[1.2.1]
The above-described Factor C, which exhibits a residual activity of 10% or higher in the presence of 21 mM sodium citrate.
[1.2.2]
The above-described Factor C, which exhibits a residual activity of 20% or higher in the presence of 21 mM sodium citrate.
[1.2.3]
The above-described Factor C, which exhibits a residual activity of 25% or higher in the presence of 52 mM sodium hydrogencarbonate.
[1.2.4]
The above-described Factor C, which exhibits a residual activity of 35% or higher in the presence of 52 mM sodium hydrogencarbonate.
[1.2.5]
The above-described Factor C, which exhibits a residual activity of 25% or higher in the presence of 214 mM sodium chloride.
[1.2.6]
The above-described Factor C, which exhibits a residual activity of 35% or higher in the presence of 214 mM sodium chloride.
[1.2.7]
The above-described Factor C, which exhibits a residual activity of 15% or higher in the presence of 16 mM magnesium sulfate.
[1.2.8]
The above-described Factor C, which exhibits a residual activity of 25% or higher in the presence of 16 mM magnesium sulfate.
[1.2.9]
The above-described Factor C, which exhibits a residual activity of 35% or higher in the presence of 2.5 mM calcium chloride.
[1.2.10]
The above-described Factor C, which exhibits a residual activity of 45% or higher in the presence of 2.5 mM calcium chloride.
[1.2.11]
The above-described Factor C, which exhibits a higher residual activity in the presence of 21 mM sodium citrate, as compared with a horseshoe crab Factor C expressed in Sf9 as a host cell and/or a native Factor C.
[1.2.12]
The above-described Factor C, which exhibits a higher residual activity in the presence of 52 mM sodium hydrogencarbonate, as compared with a horseshoe crab Factor C expressed in Sf9 as a host cell and/or a native Factor C.
[1.2.13]
The above-described Factor C, which exhibits a higher residual activity in the presence of 214 mM sodium chloride, as compared with a horseshoe crab Factor C expressed in Sf9 as a host cell and/or a native Factor C.
[1.2.14]
The above-described Factor C, which exhibits a higher residual activity in the presence of 16 mM magnesium sulfate, as compared with a horseshoe crab Factor C expressed in Sf9 as a host cell and/or a native Factor C.
[1.2.15]
The above-described Factor C, which exhibits a higher residual activity in the presence of 2.5 mM calcium chloride, as compared with a horseshoe crab Factor C expressed in Sf9 as a host cell and/or a native Factor C.
[1.3.1]
The Factor C, which is a protein shown in the following (A), (B), (C), or (D):
(A) a protein comprising the amino acid sequence shown in SEQ ID NO: 2;
(B) a protein comprising the amino acid sequence shown in SEQ ID NO:2 but which includes substitution, deletion, insertion, or addition of one or several amino acid residues, and having activity of Factor C;
(C) a protein comprising the amino acid sequence shown in SEQ ID NO: 4;
(D) a protein comprising the amino acid sequence shown in SEQ ID NO:4 but which includes substitution, deletion, insertion, or addition of one or several amino acid residues, and having activity of Factor C.
[1.3.2]
The Factor C, which is a protein shown in the following (A) or (B):
(A) a protein comprising the amino acid sequence shown in SEQ ID NO: 2;
(B) a protein comprising the amino acid sequence shown in SEQ ID NO:2 but which includes substitution, deletion, insertion, or addition of one or several amino acid residues, and having activity of Factor C.

[1.4]
The above-described Factor C, which is a recombinant protein.

[1.5.1]
The above-described Factor C, which has a molecular weight of 115 kDa to 140 kDa, as measured through SDS-PAGE under a non-reducing condition.

[1.5.2]
The above-described Factor C, which has a molecular weight of 115 kDa to 130 kDa, as measured through SDS-PAGE under a non-reducing condition.

[1.5.3]
The above-described Factor C, which has a molecular weight of 120 kDa to 130 kDa, as measured through SDS-PAGE under a non-reducing condition.

[1.5.4]
The above-described Factor C, which has a molecular weight of 120 kDa to 128 kDa, as measured through SDS-PAGE under a non-reducing condition.

[1.5.5]
The above-described Factor C, which has a molecular weight of 127 kDa±5 kDa, as measured through SDS-PAGE under a non-reducing condition.

[1.5.6]
The above-described Factor C, which has a molecular weight of 128 kDa±2 kDa, as measured through SDS-PAGE under a non-reducing condition.

[1.5.7]
The above-described Factor C, which has a molecular weight of 127 kDa±2 kDa, as measured through SDS-PAGE under a non-reducing condition.

[1.5.8]
The above-described Factor C, which has a molecular weight of 126 kDa±2 kDa, as measured through SDS-PAGE under a non-reducing condition.

[1.5.9]
The above-described Factor C, which has a molecular weight of 127 kDa±1 kDa, as measured through SDS-PAGE under a non-reducing condition.

[1.6]
The above-described Factor C, which is water-soluble.

[1.7]
The above-described Factor C, which is a culture supernatant containing Factor C.

[1.8]
The above-described Factor C, which has the following characteristics (1) to (3):
(1) having activity of Factor C;
(2) having a molecular weight of 115 kDa to 130 kDa, as measured through SDS-PAGE under a non-reducing condition; and
(3) exhibiting a residual activity of 10% or higher in the presence of 21 mM sodium citrate.

[2]
A method for producing a horseshoe crab Factor C, the method comprising expressing the horseshoe crab Factor C in a mammalian cell as a host cell.

[2.1.1]
The above-described method, wherein the mammalian cell is a mammalian cell other than COS-1.

[2.1.2]
The above-described method, wherein the mammalian cell is a cell of a mammal selected from the group consisting of a primate and a rodent.

[2.1.3]
The above-described method, wherein the mammalian cell is a primate cell.

[2.1.4]
The above-described method, wherein the mammalian cell is a rodent cell.

[2.1.5]
The above-described method, wherein the mammalian cell is a cell of a mammal selected from the group consisting of a primate and a rodent, other than monkey.

[2.1.6]
The above-described method, wherein the mammalian cell is a Chinese hamster cell or a human cell.

[2.1.7]
The above-described method, wherein the mammalian cell is a Chinese hamster cell.

[2.1.8]
The above-described method, wherein the mammalian cell is a human cell.

[2.1.9]
The above-described method, wherein the mammalian cell is CHO or HEK.

[2.1.10]
The above-described method, wherein the mammalian cell is CHO.

[2.1.11]
The above-described method, wherein the mammalian cell is HEK.

[2.1.12]
The above-described method, wherein the mammalian cell is CHO DG44 or HEK293.

[2.1.13]
The above-described method, wherein the mammalian cell is CHO DG44.

[2.1.14]
The above-described method, wherein the mammalian cell is HEK293.

[2.2.1]
The above-described method, wherein the Factor C is a protein shown in the following (A), (B), (C), or (D):
(A) a protein comprising the amino acid sequence shown in SEQ ID NO: 2;
(B) a protein comprising the amino acid sequence shown in SEQ ID NO:2 but which includes substitution, deletion, insertion, or addition of one or several amino acid residues, and having activity of Factor C;
(C) a protein comprising the amino acid sequence shown in SEQ ID NO: 4;
(D) a protein comprising the amino acid sequence shown in SEQ ID NO:4 but which includes substitution, deletion, insertion, or addition of one or several amino acid residues, and having activity of Factor C.

[2.2.2]
The above-described method, wherein the Factor C is a protein shown in the following (A) or (B):
(A) a protein comprising the amino acid sequence shown in SEQ ID NO: 2;
(B) a protein comprising the amino acid sequence shown in SEQ ID NO:2 but which includes substitution, deletion, insertion, or addition of one or several amino acid residues, and having activity of Factor C.

[3]
A horseshoe crab Factor C producible by the above-described method.

[3.1]
The above-described Factor C, which has activity of Factor C.

[3.2.1]
The above-described Factor C, which contains sialic acid.

[3.2.2]
The above-described Factor C, which contains (α-2,3) linked terminal sialic acid.

[3.2.3]
The above-described Factor C, which contains (α-2,3) linked terminal sialic acid in a greater amount, as compared with a native Factor C.

[3.2.4]
The above-described Factor C, which contains (α-2,3) linked terminal sialic acid in a greater amount, as compared with a horseshoe crab Factor C expressed in Sf9 as a host cell.

[3.2.5]
The above-described Factor C, which exhibits a higher reactivity in lectin blotting by use of *Maackia amurensis* agglutinin, as compared with a native Factor C.

[3.2.6]
The above-described Factor C, which exhibits a higher reactivity in lectin blotting by use of *Maackia amurensis* agglutinin, as compared with a horseshoe crab Factor C expressed in Sf9 as a host cell.

[3.3.1]
The above-described Factor C, which exhibits a residual activity of 10% or higher in the presence of 21 mM sodium citrate.

[3.3.2]
The above-described Factor C, which exhibits a residual activity of 20% or higher in the presence of 21 mM sodium citrate.

[3.3.3]
The above-described Factor C, which exhibits a residual activity of 25% or higher in the presence of 52 mM sodium hydrogencarbonate.

[3.3.4]
The above-described Factor C, which exhibits a residual activity of 35% or higher in the presence of 52 mM sodium hydrogencarbonate.

[3.3.5]
The above-described Factor C, which exhibits a residual activity of 25% or higher in the presence of 214 mM sodium chloride.

[3.3.6]
The above-described Factor C, which exhibits a residual activity of 35% or higher in the presence of 214 mM sodium chloride.

[3.3.7]
The above-described Factor C, which exhibits a residual activity of 15% or higher in the presence of 16 mM magnesium sulfate.

[3.3.8]
The above-described Factor C, which exhibits a residual activity of 25% or higher in the presence of 16 mM magnesium sulfate.

[3.3.9]
The above-described Factor C, which exhibits a residual activity of 35% or higher in the presence of 2.5 mM calcium chloride.

[3.3.10]
The above-described Factor C, which exhibits a residual activity of 45% or higher in the presence of 2.5 mM calcium chloride.

[3.3.11]
The above-described Factor C, which exhibits a higher residual activity in the presence of 21 mM sodium citrate, as compared with a horseshoe crab Factor C expressed in Sf9 as a host cell and/or a native Factor C.

[3.3.12]
The above-described Factor C, which exhibits a higher residual activity in the presence of 52 mM sodium hydrogencarbonate, as compared with a horseshoe crab Factor C expressed in Sf9 as a host cell and/or a native Factor C.

[3.3.13]
The above-described Factor C, which exhibits a higher residual activity in the presence of 214 mM sodium chloride, as compared with a horseshoe crab Factor C expressed in Sf9 as a host cell and/or a native Factor C.

[3.3.14]
The above-described Factor C, which exhibits a higher residual activity in the presence of 16 mM magnesium sulfate, as compared with a horseshoe crab Factor C expressed in Sf9 as a host cell and/or a native Factor C.

[3.3.15]
The above-described Factor C, which exhibits a higher residual activity in the presence of 2.5 mM calcium chloride, as compared with a horseshoe crab Factor C expressed in Sf9 as a host cell and/or a native Factor C.

[3.4]
The above-described Factor C, which is a recombinant protein.

[3.5.1]
The above-described Factor C, which has a molecular weight of 115 kDa to 140 kDa, as measured through SDS-PAGE under a non-reducing condition.

[3.5.2]
The above-described Factor C, which has a molecular weight of 115 kDa to 130 kDa, as measured through SDS-PAGE under a non-reducing condition.

[3.5.3]
The above-described Factor C, which has a molecular weight of 120 kDa to 130 kDa, as measured through SDS-PAGE under a non-reducing condition.

[3.5.4]
The above-described Factor C, which has a molecular weight of 120 kDa to 128 kDa, as measured through SDS-PAGE under a non-reducing condition.

[3.5.5]
The above-described Factor C, which has a molecular weight of 127 kDa±5 kDa, as measured through SDS-PAGE under a non-reducing condition.

[3.5.6]
The above-described Factor C, which has a molecular weight of 128 kDa±2 kDa, as measured through SDS-PAGE under a non-reducing condition.

[3.5.7]
The above-described Factor C, which has a molecular weight of 127 kDa±2 kDa, as measured through SDS-PAGE under a non-reducing condition.

[3.5.8]
The above-described Factor C, which has a molecular weight of 126 kDa±2 kDa, as measured through SDS-PAGE under a non-reducing condition.

[3.5.9]
The above-described Factor C, which has a molecular weight of 127 kDa±1 kDa, as measured through SDS-PAGE under a non-reducing condition.

[3.6]
The above-described Factor C, which is water-soluble.

[3.7]
The above-described Factor C, which is a culture supernatant containing Factor C.

[4]
An endotoxin assay agent containing the above-described Factor C.
[4.1]
The above-described assay agent, which further contains a horseshoe crab Factor B and a horseshoe crab Pro-clotting enzyme.
[4.2]
The above-described assay agent, wherein the Factor B is a protein shown in the following (E) or (F) and the Pro-clotting enzyme is a protein shown in the following (G) or (H):
(E) a protein comprising the amino acid sequence shown in SEQ ID NO: 6;
(F) a protein comprising the amino acid sequence shown in SEQ ID NO:6 but which includes substitution, deletion, insertion, or addition of one or several amino acid residues, and having activity of Factor B;
(G) a protein comprising the amino acid sequence shown in SEQ ID NO: 8;
(H) a protein comprising the amino acid sequence shown in SEQ ID NO:8 but which includes substitution, deletion, insertion, or addition of one or several amino acid residues, and having activity of Pro-clotting enzyme.
[5]
An endotoxin assay kit comprising the above-described assay agent.
[6]
A method for measuring endotoxin in a test specimen, the method comprising a step of mixing the above-described assay agent and the test specimen, and a step of measuring the progress of a cascade reaction.
[6.1.1]
The above-described method, wherein the test specimen contains an ion.
[6.1.2]
The above-described method, wherein the test specimen contains a cation.
[6.1.3]
The above-described method, wherein the test specimen contains a metal ion.
[6.1.4]
The above-described method, wherein the test specimen contains an alkali metal ion or an alkaline earth metal ion.
[6.1.5]
The above-described method, wherein the test specimen contains an alkali metal ion.
[6.1.6]
The above-described method, wherein the test specimen contains an alkaline earth metal ion.
[6.2.1]
The above-described method, wherein the test specimen contains one or more kinds of ions selected from the group consisting of sodium ion, potassium ion, calcium ion, and magnesium ion.
[6.2.2]
The above-described method, wherein the test specimen contains sodium ion.
[6.2.3]
The above-described method, wherein the test specimen contains potassium ion.
[6.2.4]
The above-described method, wherein the test specimen contains calcium ion.
[6.2.5]
The above-described method, wherein the test specimen contains magnesium ion.

[6.3.1]
The above-described method, wherein the contained amount of the ion in the test specimen is such an amount that the concentration of the cation derived from the test specimen becomes 1 mM or higher, as a final concentration in the reaction system after mixing the test specimen with the assay agent.
[6.3.2]
The above-described method, wherein the contained amount of the ion in the test specimen is such an amount that the concentration of the cation derived from the test specimen becomes 2 mM or higher, as a final concentration in the reaction system after mixing the test specimen with the assay agent.
[6.3.3]
The above-described method, wherein the contained amount of the ion in the test specimen is such an amount that the concentration of the cation derived from the test specimen becomes 5 mM or higher, as a final concentration in the reaction system after mixing the test specimen with the assay agent.
[6.3.4]
The above-described method, wherein the contained amount of the ion in the test specimen is such an amount that the concentration of the cation derived from the test specimen becomes 10 mM or higher, as a final concentration in the reaction system after mixing the test specimen with the assay agent.
[6.3.5]
The above-described method, wherein the contained amount of the ion in the test specimen is such an amount that the concentration of the cation derived from the test specimen becomes 20 mM or higher, as a final concentration in the reaction system after mixing the test specimen with the assay agent.
[6.3.6]
The above-described method, wherein the contained amount of the ion in the test specimen is such an amount that the concentration of the cation derived from the test specimen becomes 50 mM or higher, as a final concentration in the reaction system after mixing the test specimen with the assay agent.
[6.3.7]
The above-described method, wherein the contained amount of the ion in the test specimen is such an amount that the concentration of the cation derived from the test specimen becomes 100 mM or higher, as a final concentration in the reaction system after mixing the test specimen with the assay agent.
[6.4]
The above-described method, wherein the test specimen is an injection.
[6.5.1]
The above-described method, wherein the test specimen contains one or more kinds of salts selected from the group consisting of sodium chloride, magnesium sulfate, sodium hydrogencarbonate, sodium citrate, calcium chloride, potassium chloride, sodium iothalamate, calcium disodium edetate, and dihydrogen sodium phosphate.
[6.5.2]
The above-described method, wherein the test specimen contains sodium chloride.
[6.5.3]
The above-described method, wherein the test specimen contains magnesium sulfate.

[6.5.4]
The above-described method, wherein the test specimen contains sodium hydrogencarbonate.
[6.5.5]
The above-described method, wherein the test specimen contains sodium citrate.
[6.5.6]
The above-described method, wherein the test specimen contains calcium chloride.
[6.5.7]
The above-described method, wherein the test specimen contains potassium chloride.
[6.5.8]
The above-described method, wherein the test specimen contains sodium iothalamate.
[6.5.9]
The above-described method, wherein the test specimen contains calcium disodium edetate.
[6.5.10]
The above-described method, wherein the test specimen contains dihydrogen sodium phosphate.
[6.6.1]
The above-described method, wherein the contained amount of the salt in the test specimen is such an amount that the concentration of the salt derived from the test specimen becomes 1 mM or higher, as a final concentration in the reaction system after mixing the test specimen with the assay agent.
[6.6.2]
The above-described method, wherein the contained amount of the salt in the test specimen is such an amount that the concentration of the salt derived from the test specimen becomes 2 mM or higher, as a final concentration in the reaction system after mixing the test specimen with the assay agent.
[6.6.3]
The above-described method, wherein the contained amount of the salt in the test specimen is such an amount that the concentration of the salt derived from the test specimen becomes 5 mM or higher, as a final concentration in the reaction system after mixing the test specimen with the assay agent.
[6.6.4]
The above-described method, wherein the contained amount of the salt in the test specimen is such an amount that the concentration of the salt derived from the test specimen becomes 10 mM or higher, as a final concentration in the reaction system after mixing the test specimen with the assay agent.
[6.6.5]
The above-described method, wherein the contained amount of the salt in the test specimen is such an amount that the concentration of the salt derived from the test specimen becomes 20 mM or higher, as a final concentration in the reaction system after mixing the test specimen with the assay agent.
[6.6.6]
The above-described method, wherein the contained amount of the salt in the test specimen is such an amount that the concentration of the salt derived from the test specimen becomes 50 mM or higher, as a final concentration in the reaction system after mixing the test specimen with the assay agent.
[6.6.7]
The above-described method, wherein the contained amount of the salt in the test specimen is such an amount that the concentration of the salt derived from the test specimen becomes 100 mM or higher, as a final concentration in the reaction system after mixing the test specimen with the assay agent.
[6.7]
The above-described method, which further comprises a step of adding, to the reaction system, a substrate for detecting the progress of the cascade reaction.
[6.8]
The above-described method, which further comprises a step of calculating the amount of endotoxin in the test specimen.

BRIEF DESCRIPTION OF THE DRAWINGS

FIG. 1 A chart showing a cascade reaction system of the limulus test.

FIG. 2 A photograph showing the results of western blotting of four types of Factor C (Sf9, CHO, HEK, and TAL) derived from Japanese horseshoe crab (*Tachypleus tridentatus*), under non-reducing conditions.

FIG. 3 A photograph (SDS-PAGE) showing the molecular weight of each of a native Factor C (TAL) derived from Japanese horseshoe crab (*Tachypleus tridentatus*) and a recombinant Factor C (CHO).

FIG. 4 A scheme of measuring the activity of Factor C.

FIG. 5 A chart showing a reconstituted cascade reaction system.

FIG. 6 A table and a graph showing the activity of the four types of Factor C (Sf9, CHO, HEK, and TAL) derived from Japanese horseshoe crab (*Tachypleus tridentatus*).

FIG. 7 A table and a graph showing the activity inhibition by injections of the four types of Factor C (Sf9, CHO, HEK, and TAL) derived from Japanese horseshoe crab (*Tachypleus tridentatus*).

FIG. 8 Alignment of Factor C of *Tachypleus tridentatus* (TtFC; SEQ ID NO: 2) and Factor C of *Carcinoscorpius rotundicauda* (834CrID4; SEQ ID NO: 4) (continued to FIG. 9). Consensus sequences which can undergo N-type sugar chain (N-linked sugar chain) modification are underlined.

FIG. 9 Alignment of Factor C of *Tachypleus tridentatus* (TtFC; SEQ ID NO: 2) and Factor C of *Carcinoscorpius rotundicauda* (834CrID4; SEQ ID NO: 4) (continued from FIG. 8). Consensus sequences which can undergo N-type sugar chain (N-linked sugar chain) modification are underlined.

FIG. 10 A schematic representation of reaction sites between Factor C and specific antibodies under reducing and non-reducing conditions.

FIG. 11 A photograph (SDS-PAGE) showing the molecular weight of the four types of purified Factor C derived from Japanese horseshoe crab (*Tachypleus tridentatus*).

FIG. 12 A photograph (western blotting) showing the molecular weight of the four types of purified Factor C derived from Japanese horseshoe crab (*Tachypleus tridentatus*).

FIG. 13 A photograph (western blotting) showing the results of removal of N-type sugar chain, by glycopeptidase F, from the four types of purified Factor C derived from Japanese horseshoe crab (*Tachypleus tridentatus*).

FIG. 14 (a) A photograph (lectin blotting) showing the results of detection of N-type sugar chain of the four types of purified Factor C derived from Japanese horseshoe crab (*Tachypleus tridentatus*); (b) a table showing the biding specificity of lectin; and (c) a schematic representation of N-type sugar chain structures of a recombinant Factor C, assumed by the experimental results and reports by documents.

MODES FOR CARRYING OUT THE INVENTION

In the present invention, a series of reactions wherein endotoxin activates Factor C to generate active-type Factor C; the active-type Factor C activates Factor B to generate active-type Factor B; and the active-type Factor B activates Pro-clotting enzyme to generate a corresponding Clotting enzyme; may be referred to as "cascade reaction". In the present invention, Factor C, Factor B, and Pro-clotting enzyme may be collectively referred to as "factor". In the present invention, a cascade reaction system constituted by combining the factors may be referred to as "reconstituted system". In such a reconstituted system, an effect of a contaminant contained in an amebocyte lysate of a horseshoe crab, e.g. Factor G, on the cascade reaction can be eliminated.

(1) Factor C of the Present Invention

The Factor C of the present invention is a Factor C derived from a horseshoe crab. The Factor C of the present invention is a recombinant protein. The term "recombinant protein" refers to a protein obtained through introduction of a gene encoding the protein into a host cell and heterologous expression of the gene. The Factor C of the present invention has activity of Factor C.

Examples of the horseshoe crab include *Tachypleus tridentatus* (Japanese horseshoe crab), *Limulus polyphemus* (American horseshoe crab), *Carcinoscorpius rotundicauda* (Southeast Asian (Singaporean) horseshoe crab), and *Tachypleus gigas* (Southeast Asian horseshoe crab). Among them, *Tachypleus tridentatus* (Japanese horseshoe crab) and *Carcinoscorpius rotundicauda* (Southeast Asian (Singaporean) horseshoe crab) are preferred as a Factor C source. Furthermore, among them, *Tachypleus tridentatus* (Japanese horseshoe crab) is more preferred as a Factor C source. The amino acid sequence of the Factor C derived from *Tachypleus tridentatus* is shown in SEQ ID NO: 2. The nucleotide sequence of a gene encoding the Factor C derived from *Tachypleus tridentatus* is shown in SEQ ID NO: 1. The amino acid sequence of the Factor C derived from *Carcinoscorpius rotundicauda* is shown in SEQ ID NO: 4. The nucleotide sequence of a gene encoding the Factor C derived from *Carcinoscorpius rotundicauda* is shown in SEQ ID NO: 3.

The Factor C of the present invention may undergo N-type sugar chain (N-linked sugar chain) modification. The term "N-type sugar chain" refers to a sugar chain which is linked to an asparagine residue of a protein. In the Factor C derived from *Tachypleus tridentatus* and the Factor C derived from *Carcinoscorpius rotundicauda*, the amino acid residues which can undergo N-type sugar chain modification are conserved. FIGS. 8 and 9 show alignments and consensus sequences (Asn-Xaa-Ser/Thr, wherein Xaa represents any amino acid residue) which can undergo N-type sugar chain modification of both types of Factor C. Thus, in particular, the Factor C derived from *Carcinoscorpius rotundicauda* is thought to be a suitable Factor C as with the Factor C derived from *Tachypleus tridentatus*.

The Factor C of the present invention may contain a sialic acid. Examples of the sialic acid include N-acetylneuraminic acid (Neu5Ac) and N-glycolylneuraminic acid (Neu5Gc). The expression "containing a sialic acid" refers to the state that a sialic acid is linked to the Factor C of the present invention. The sialic acid may be linked to Factor C directly or indirectly. In one case, a sugar chain containing a sialic acid may be linked to Factor C, whereby the sialic acid may be indirectly linked to Factor C. The sialic acid may be, for example, an ($\alpha$-2,3)-linked sialic acid, more specifically, an ($\alpha$-2,3)-linked terminal sialic acid. The term "($\alpha$-2,3)-linked sialic acid" refers to a sialic acid linked to a sugar via ($\alpha$-2,3) glycoside linkage. The term "($\alpha$-2,3)-linked terminal sialic acid" refers to a sialic acid which is linked to a sugar via ($\alpha$-2,3) glycoside linkage and which is located at a terminus of the sugar chain. An example of the sugar chain is an N-type sugar chain (N-linked sugar chain). The sialic acid may be added to Factor C through, for example, expression of Factor C in a host cell which can add a sialic-acid-containing sugar chain to a protein through modification after translation. Examples of such a host cell include mammalian cells. Sialic acid may be detected through, for example, sugar chain analysis. Sugar chain analysis may be carried out through a known technique. For example, sugar chain analysis can be carried out by using lectin or a sugar-chain-recognizing antibody. Specifically, for example, an ($\alpha$-2,3)-linked terminal sialic acid can be specifically detected through lectin blotting using *Maackia amurensis* agglutinin (MAM).

The Factor C of the present invention may contain sialic acid in a greater amount, as compared with a control Factor C. The expression "containing sialic acid in a greater amount, as compared with a control Factor C" refers to the state that the amount of sialic acid linked to the Factor C of the present invention is greater than the amount of sialic acid linked to the control Factor C, in terms of the amount by mole of sialic acid per molecule of Factor C. For example, the amount of sialic acid linked to the Factor C of the present invention may be 1.1 times or greater, 1.2 times or greater, 1.3 times or greater, 1.5 times or greater, 2.0 times or greater, 2.5 times or greater, or 3.0 times or greater than the amount of sialic acid linked to the control Factor C, in terms of the amount by mole of sialic acid per molecule of Factor C.

Examples of the control Factor C include a recombinant Factor C expressed in insect cell Sf9, and a native Factor C. The expression "Factor C expressed in Sf9 as a host cell" refers to Factor C obtainable through expression of a gene encoding Factor C consisting of the same amino acid sequence as that of the Factor C of the present invention, in SF9 as a host cell. The term "native Factor C" refers to Factor C isolated and purified from a horseshoe crab lysate. The native Factor C may be Factor C isolated and purified from a lysate of a horseshoe crab from which the Factor C of the present invention is derived. That is, specifically, for example, when the Factor C of the present invention is a recombinant Factor C of *Tachypleus tridentatus* or a variant thereof, the native Factor C may be Factor C isolated and purified from a lysate of *Tachypleus tridentatus*.

Whether or not "the Factor C of the present invention contains sialic acid in a greater amount, as compared with a control Factor C" may be determined through comparison between the sialic acid amount of the Factor C of the present invention and that of the control Factor C. The amount of sialic acid may be determined through, for example, sugar chain analysis. Sugar chain analysis may be carried out through a known technique. For example, sugar chain analysis can be carried out by using lectin or a sugar-chain-recognizing antibody. Specifically, for example, an ($\alpha$-2,3)-linked terminal sialic acid can be specifically quantitated through lectin blotting using *Maackia amurensis* agglutinin (MAM). It can be confirmed that the higher the reactivity in lectin blotting using MAM, the greater the amount of (α-2,3)-linked terminal sialic acid, and that is, the greater amount of (α-2,3)-linked terminal sialic acid the Factor C contains. In other words, the Factor C of the present invention may exhibit higher reactivity, as compared with the control Factor C, in lectin blotting using MAM. The expression "exhibit higher reactivity, as compared with the control Factor C, in lectin blotting using MAM" refers to the state that, when the equiamount of the Factor C of the present invention and the control Factor C are subjected to lectin blotting using MAM, the detection intensity (such as the extent of coloring) of the spot attributed to the Factor C of the present invention is higher than that of the spot attributed to the control Factor C.

The Factor C of the present invention may have no His-tag added to the C-terminus. Also, the Factor C of the present invention may have no V5-tag added to the C-terminus. Also, the Factor C of the present invention may have no peptide added to the C-terminus. Also, the Factor C of the present invention may have no peptide added to the N-terminus. Also, the Factor C of the present invention may have no peptide added to any of the N-terminus and the C-terminus.

So long as the Factor C of the present invention has activity of Factor C, the Factor C may be a variant of any of the aforementioned horseshoe crab Factor C proteins (e.g., a protein having the amino acid sequence shown in SEQ ID NO: 2 or 4). Such a variant includes, for example, a homologue and an artificially modified product of the aforementioned Factor C. Notably, the amino acid sequence of the variant is not necessarily found in an actual horseshoe crab. That is, the Factor C "of a horseshoe crab or derived from a horseshoe crab" includes a variant of Factor C found in a horseshoe crab and having an amino acid sequence which is not found in any horseshoe crab.

The activity of Factor C refers to such an activity that the Factor C is activated in the presence of endotoxin to convert Factor B into activated Factor B. Whether "the Factor C of the present invention has activity of Factor C" can be confirmed, for example, by combining the Factor C of the present invention with a suitable Factor B and a suitable Pro-clotting enzyme in the presence of endotoxin, and detecting the progress of the cascade reaction. Specifically, the protein of SEQ ID NO: 6 and the protein of SEQ ID NO: 8 may be used as a suitable Factor B and a suitable Pro-clotting enzyme, respectively. The progress of the cascade reaction may be determined by use of the below-mentioned substrate for detection.

So long as the Factor C of the present invention has activity of Factor C, the Factor C of the present invention may be a protein having the amino acid sequence of the above-mentioned Factor C such as the amino acid sequence shown in SEQ ID NO:2 or 4, but which includes substitution, deletion, insertion, or addition of one or several amino acid residues. Although the meaning of the term "one or several" varies depending on the positions of the amino acid residues in the three-dimensional structure of the protein and the types of the amino acid residues, the term specifically refers to preferably 1 to 20, more preferably 1 to 10, still more preferably 1 to 5, particularly preferably 1 to 3. The substitution, deletion, insertion, or addition of one or several amino acid residues is a conservative variation where the function of the protein is appropriately maintained. A typical conservative variation is conservative substitution. Conservative substitution is a variation among Phe, Trp, and Tyr, in the case where the substitution occurs at an aromatic amino acid residue; a variation among Leu, Ile, and Val, in the case where the substitution occurs at a hydrophobic amino acid residue; a variation between Gln and Asn, in the case where the substitution occurs at a polar amino acid residue; a variation among Lys, Arg, and His, in the case where the substitution occurs at a basic amino acid residue; a variation between Asp and Glu, in the case where the substitution occurs at an acidic amino acid residue; or a variation between Ser and Thr, in the case where the substitution occurs at an amino acid residue having a hydroxyl group. Specific examples of the substitution which can be recognized as conservative substitution include a substitution of Ala by Ser or Thr; a substitution of Arg by Gln, His, or Lys; a substitution of Asn by Glu, Gln, Lys, His, or Asp; a substitution of Asp by Asn, Glu, or Gln; a substitution of Cys by Ser or Ala; a substitution of Gln by Asn, Glu, Lys, His, Asp, or Arg; a substitution of Glu by Gly, Asn, Gln, Lys, or Asp; a substitution of Gly by Pro; a substitution of His by Asn, Lys, Gln, Arg, or Tyr; a substitution of Ile by Leu, Met, Val, or Phe; a substitution of Leu by Ile, Met, Val, or Phe; a substitution of Lys by Asn, Glu, Gln, His, or Arg; a substitution of Met by Ile, Leu, Val, or Phe; a substitution of Phe by Trp, Tyr, Met, Ile, or Leu; a substitution of Ser by Thr or Ala; a substitution of Thr by Ser or Ala; a substitution of Trp by Phe or Tyr; a substitution of Tyr by His, Phe, or Trp; and a substitution of Val by Met, Ile, or Leu. The aforementioned substitution, deletion, insertion, addition, or the like of an amino acid residue(s) also encompasses naturally occurring variations such as those based on individual differences between horseshoe crabs and the strain and species of the horseshoe crabs, from which the gene is derived.

The Factor C of the present invention may also be a protein which has a homology or identity of 80% or higher, preferably 90% or higher, more preferably 95% or higher, still more preferably 97% or higher, particularly preferably 99% or higher with respect to the entire amino acid sequence of Factor C (e.g., the entire amino acid sequence shown in SEQ ID NO: 2 or 4) and which has activity of Factor C.

The gene encoding the Factor C of the present invention is not particularly limited, so long as the gene codes for the aforementioned Factor C of the present invention. The gene encoding the Factor C of the present invention may be a DNA encoding a protein having activity of Factor C, wherein the DNA fragment is hybridized with a probe prepared from a known gene sequence, e.g., with the complementary sequence to the entirety or a part of the nucleotide sequence shown SEQ ID NO: 1 or 3, under stringent conditions. As used herein, the term "stringent conditions" generally refer to the conditions under which a specific hybrid is formed but a non-specific hybrid is not formed. An example of such conditions is conditions under which DNAs having a high homology, e.g., a homology of 80% or higher, preferably 90% or higher, more preferably 95% or higher, still more preferably 97% or higher, particularly preferably 99% or higher, are hybridized with each other, and DNAs having a homology lower than the above level are not hybridized with each other. Another example of the conditions is conditions generally employed in washing of southern hybridization; i.e., washing once, preferably 2 to 3 times, at temperature and salt concentration corresponding to 60° C., 1×SSC, 0.1% SDS, preferably 60° C., 0.1×SSC, 0.1% SDS, more preferably 68° C., 0.1×SSC, 0.1% SDS.

In the gene encoding the Factor C of the present invention, any codon may be substituted by its equivalent codon. For example, the codon combination of the gene encoding the Factor C of the present invention may be modified such that the codon combination is optimized for expression in a mammalian cell. The optimization may be performed through employment of, for example, a conventional contract service. Notably, the gene encoding the Factor C of the present invention may be a variant of a DNA in which the codon combination is optimized for expression in a mammalian cell.

The above descriptions about the variants of genes and proteins may also be applied mutatis mutandis to Factor B, Pro-clotting enzyme, and gene encoding the same.

The Factor C of the present invention may have a molecular weight of 115 kDa to 140 kDa, 115 kDa to 130 kDa, 120 kDa to 130 kDa, or 120 kDa to 128 kDa, as measured through SDS-PAGE under a non-reducing condition. Also, the Factor C of the present invention may have a molecular weight of 127 kDa±5 kDa, 128 kDa±2 kDa, 127 kDa±2 kDa, 126 kDa±2 kDa, or 127 kDa±1 kDa, as measured through SDS-PAGE under a non-reducing condition. Also, the Factor C of the present invention may have a molecular weight of 128 kDa or 126 kDa, as measured through SDS-PAGE under a non-reducing condition.

The Factor C of the present invention may have low susceptibility to inhibition of activity by an ion. The expression "low susceptibility to inhibition of activity by an ion" refers to the state that the Factor C of the present invention exhibits a high residual activity in the presence of an ion, as compared with a control Factor C. Examples of the control Factor C include a recombinant Factor C expressed in insect cell Sf9 and a native Factor C. The meaning of the expression "exhibiting a high residual activity" is not particularly limited, so long as the residual activity of the Factor C of the present invention is higher than that of the control Factor C. The expression "exhibiting a high residual activity" may refer to, for example, the state that the residual activity of the Factor C of the present invention is 1.1 times or higher, 1.2 times or higher, 1.3 times or higher, 1.5 times or higher, 2.0 times or higher, 2.5 times or higher, or 3.0 times or higher than the residual activity of the control Factor C. Specific examples of "low susceptibility to inhibition of activity by an ion" include such a property that the Factor C of the present invention exhibits a higher residual activity in the presence of 21 mM sodium citrate, as compared with the control Factor C; such a property that the Factor C of the present invention exhibits a higher residual activity in the presence of 52 mM sodium hydrogencarbonate, as compared with the control Factor C; such a property that the Factor C of the present invention exhibits a higher residual activity in the presence of 214 mM sodium chloride, as compared with the control Factor C; such a property that the Factor C of the present invention exhibits a higher residual activity in the presence of 16 mM magnesium sulfate, as compared with the control Factor C; and such a property that the Factor C of the present invention exhibits a higher residual activity in the presence of 2.5 mM calcium chloride, as compared with the control Factor C. Specific examples of "low susceptibility to inhibition of activity by an ion" further include such a property that the Factor C of the present invention exhibits a residual activity of 10% or higher or 20% or higher in the presence of 21 mM sodium citrate, as compared with the control Factor C; such a property that the Factor C of the present invention exhibits a residual activity of 25% or higher or 35% or higher in the presence of 52 mM sodium hydrogencarbonate, as compared with the control Factor C; such a property that the Factor C of the present invention exhibits a residual activity of 25% or higher or 35% or higher in the presence of 214 mM sodium chloride, as compared with the control Factor C; such a property that the Factor C of the present invention exhibits a residual activity of 15% or higher or 25% or higher in the presence of 16 mM magnesium sulfate, as compared with the control Factor C; and such a property that the Factor C of the present invention exhibits a residual activity of 35% or higher or 45% or higher in the presence of 2.5 mM calcium chloride, as compared with the control Factor C. The Factor C of the present invention may have any one of the above properties singly or two or more of the above properties in combination. The "residual activity" is defined as a relative reactivity (%) observed for a measurement specimen (endotoxin concentration: 0.05 EU/mL) prepared by adding endotoxin to an ion-containing test specimen, with respect to the reactivity observed for another measurement specimen (endotoxin concentration: 0.05 EU/mL) prepared by adding endotoxin to injection water as 100%, in the assay system shown in FIG. 4.

The Factor C of the present invention may be water-soluble. As used herein, the term "water-soluble" refers to the state that, when the Factor C of the present invention is expressed in an appropriate host cell, the thus-expressed Factor C is detected in a soluble fraction. The expression "detected in a soluble fraction" may refer to the state that 20% or more, 50% or more, 80% or more, 90% or more, or 95% or more of the expressed Factor C is detected in a soluble fraction.

(2) Method for Producing the Factor C of the Present Invention

The Factor C of the present invention may be produced through, for example, expression in a mammalian cell as a host. That is, the present invention provides a method for producing a horseshoe crab Factor C, the method comprising expressing the horseshoe crab Factor C in a mammalian cell as a host cell. This method may also be referred to as "the production method of the present invention." The Factor C producible through production method of the present invention is an embodiment of the Factor C of the present invention.

The mammalian cell is not particularly limited, so long as the cell can functionally express a horseshoe crab Factor C. The term "functional expression" refers to the state that the expressed Factor C exhibits activity of Factor C. Specifically, the mammalian cell may be a cell other than COS-1 cell. The mammalian cell is preferably a cell of a mammal selected from the group consisting of a rodent and a primate. Examples of the rodent include, but are not particularly limited to, Chinese hamster, hamster, mouse, rat, and guinea pig. Of these, Chinese hamster is preferred. Examples of the Chinese hamster cell include Chinese hamster ovary (CHO) cell line. Examples of CHO include CHO DG44 and CHO K1. Examples of the primate include, but are not particularly limited to, human, monkey, and chimpanzee. The primate may be a primate other than monkey. Of these, human is preferred. Examples of the human cell include human embryo kidney (HEK) cell line. Examples of HEK include HEK293.

When the mammalian cell retains a gene encoding Factor C, the cell can express Factor C. The gene encoding Factor C may be retained in the mammalian cell, such that it can be expressed under the control of a promoter which functions in the cell. In the mammalian cell, the gene encoding Factor C, for example, may be present on a vector such as a plasmid which undergoes autonomous replication outside a chromosome, or may be introduced to a chromosome. The technique of introducing the gene encoding Factor C into a mammalian cell is not particularly limited. Examples of the vector which undergoes autonomous replication outside a chromosome include pCA7 (Makoto Takeda, et al., J. Viol. 79(22): 14346-54 (2005)). Alternatively, the gene encoding Factor C may be introduced to a chromosome of a mammalian cell by use of pCI-Neo Vector (product of Promega). The mammalian cell may retain one copy of, or two or more copies of the gene encoding Factor C.

The culture conditions under which a mammalian cell is cultured are not particularly limited, so long as the mammalian cell can proliferate. Conditions generally employed in culturing mammalian cells may be employed, after appropriate modification has been performed, if needed. A culture medium which is generally employed in culturing mammalian cells may be employed as the culture medium in the invention. Specifically, an RPMI 1640 medium (product of Sigma) or a DMEM medium (product of Sigma) may be used. Culturing can be performed, for example, as static culture at 36° C. to 38° C. under feeding of 5% $CO_2$.

Whether or not Factor C has been functionally expressed can be confirmed by measuring activity of Factor C. Expression of Factor C may also be confirmed by measuring the amount of mRNA formed via transcription of a gene encoding Factor C, or detecting Factor C through western blotting by use of an antibody.

The expressed Factor C can be recovered as a solution containing Factor C, and can be used as a component of the endotoxin assay agent of the present invention. The solution containing Factor C may be, for example, a culture broth, a culture supernatant, a disrupted cell extract, a mixture thereof, or the like. Factor C may be used after being purified to a desired extent, or may be used without any purification. In the present invention, even when a cell culture supernatant containing expressed Factor C is used as it is without any purification, satisfactory endotoxin assay performance can be attained. Purification of Factor C may be performed through, for example, a known protein purification technique. Examples of such a technique include ammonium sulfate precipitation, gel filtration chromatography, ion exchange chromatography, hydrophobic interaction chromatography, hydroxyapatite chromatography, and so forth. In the case where a tag such as His-tag has been added to Factor C, the Factor C may be purified through affinity chromatography based on affinity to the tag. A solution containing Factor C may be used after being filtered by means of a filter. For example, a 0.22-μm filter can be used as the filter.

(3) Endotoxin Assay Agent of the Present Invention

The Factor C of the present invention may be used in endotoxin assay. That is, the present invention provides an endotoxin assay agent containing the Factor C of the present invention. This endotoxin assay agent may also be referred to as an "endotoxin assay agent of the present invention." The endotoxin assay agent of the present invention may further contain a factor or factors other than Factor C, depending on the mode of endotoxin assay.

For example, the Factor C of the present invention may be used in combination with Factor B and Pro-clotting enzyme, for endotoxin assay. In other words, an embodiment of the endotoxin assay agent of the present invention is an endotoxin assay agent containing the Factor C of the present invention, Factor B, and Pro-clotting enzyme. In this case, endotoxin can be measured by detecting Clotting enzyme, which is the final product of the cascade reaction. The Factor B and the Pro-clotting enzyme contained in the embodiment of the endotoxin assay agent of the present invention may also be referred to as the "Factor B of the present invention" and the "Pro-clotting enzyme of the present invention", respectively.

Alternatively, endotoxin can be measured by detecting an intermediate stage of the cascade reaction. In this case, it is sufficient that the endotoxin assay agent of the present invention contains a factor or factors involved in from the start of the cascade reaction to the relevant intermediate stage. Specifically, for example, when endotoxin is measured by detecting the activated Factor C, which is an intermediate of the cascade reaction, it is sufficient that the endotoxin assay agent of the present invention contains Factor C.

The Factor B of the present invention is a Factor B derived from a horseshoe crab. The Pro-clotting enzyme of the present invention is a Pro-clotting enzyme derived from a horseshoe crab. Examples of the horseshoe crab include *Tachypleus tridentatus* (Japanese horseshoe crab), *Limulus polyphemus* (American horseshoe crab), *Carcinoscorpius rotundicauda* (Southeast Asian (Singaporean) horseshoe crab), and *Tachypleus gigas* (Southeast Asian horseshoe crab). Among them, *Tachypleus tridentatus* (Japanese horseshoe crab) is preferred as a source of Factor B and Pro-clotting enzyme.

The amino acid sequence of the Factor B of *Tachypleus tridentatus* and that of the Pro-clotting enzyme of *Tachypleus tridentatus* are shown in SEQ ID NOs: 6 and 8, respectively. The nucleotide sequence of a gene encoding the Factor B of *Tachypleus tridentatus* and that of a gene encoding the Pro-clotting enzyme of *Tachypleus tridentatus* are shown in SEQ ID NOs: 5 and 7, respectively.

The Factor B of the present invention may be a variant of any of the aforementioned horseshoe crab Factor B proteins (e.g., a protein having the amino acid sequence shown in SEQ ID NO: 6), so long as the variant has activity of Factor B. Such a variant includes, for example, a homologue and an artificially modified product of the aforementioned Factor B. The gene encoding the Factor B of the present invention is not particularly limited, so long as the gene codes for the Factor B of the present invention. The above descriptions about the variants of Factor C and the gene encoding Factor C may also be applied mutatis mutandis to the variants of Factor B and the gene encoding Factor B.

The activity of Factor B refers to such an activity that the Factor B is activated in the presence of activated Factor C to convert Pro-clotting enzyme into the activated form thereof, i.e. the corresponding Clotting enzyme. Whether "the Factor B of the present invention has activity of Factor B" can be confirmed, for example, by combining the Factor B of the present invention with a suitable Factor C and a suitable Pro-clotting enzyme in the presence of endotoxin, and detecting the progress of the cascade reaction. Specifically, the protein of SEQ ID NO: 2 and the protein of SEQ ID NO: 8 may be used as a suitable Factor C and a suitable Pro-clotting enzyme, respectively. The progress of the cascade reaction may be determined by use of the below-mentioned substrate for detection.

The Pro-clotting enzyme of the present invention may be a variant of any of the aforementioned horseshoe crab Pro-clotting enzymes (e.g., a protein having the amino acid sequence shown in SEQ ID NO: 8), so long as the variant has activity of Pro-clotting enzyme. Such a variant includes, for example, a homologue and an artificially modified product of the aforementioned Pro-clotting enzyme. The gene encoding the Pro-clotting enzyme of the present invention is not particularly limited, so long as the gene codes for the Pro-clotting enzyme of the present invention. The above descriptions about the variants of Factor C and the gene encoding Factor C may also be applied mutatis mutandis to the variants of Pro-clotting enzyme and the gene encoding Pro-clotting enzyme.

The activity of Pro-clotting enzyme is such an activity that the Pro-clotting enzyme is converted into the activated form thereof, i.e. the corresponding Clotting enzyme, in the presence of activated Factor B, to react with the below-mentioned substrate for detection. The activity of reacting with the detection substrate refers to, for example, an activity of reacting with a coagulogen to induce coagulation, or an activity of reacting with the below-described substrate represented by X-Y-Z (wherein X represents a protection group, Y represents a peptide, and Z represents a dye linked to Y via amide bond), to thereby release dye Z (e.g., an activity of reacting with Boc-Leu-Gly-Arg-pNA, to thereby release pNA). Whether "the Pro-clotting enzyme of the present invention has the activity of Pro-clotting enzyme" can be confirmed, for example, by combining the Pro-clotting enzyme of the present invention with a suitable Factor C and a suitable Factor B in the presence of endotoxin, and detecting the progress of the cascade reaction. Specifically, the protein of SEQ ID NO: 2 and the protein of SEQ ID NO: 6 may be used as a suitable Factor C and a suitable Factor B, respectively. The progress of the cascade reaction may be measured by use of the below-mentioned substrate for detection.

So long as the Factor B of the present invention and the Pro-clotting enzyme of the present invention has activity of Factor B and activity of Pro-clotting enzyme, respectively, the Factor B of the present invention and/or the Pro-clotting enzyme of the present invention may have any peptide or the like added thereto. Examples of such a peptide include tag sequences such as His-tag and V5-tag. Similar to Factor C of the present invention, the Factor B of the present invention and/or the Pro-clotting enzyme of the present invention may have no His-tag added to the C-terminus; may have no V5-tag added to the C-terminus; may have no peptide added to the C-terminus; may have no peptide added to the N-terminus; or may have no peptide added to any of the N-terminus and the C-terminus.

In the gene encoding the Factor B of the present invention and/or the gene encoding the Pro-clotting enzyme of the present invention, any codon may be substituted by its equivalent codon. For example, the codon combination of the gene encoding the Factor B of the present invention and/or the gene encoding the Pro-clotting enzyme of the present invention may be modified such that the codon combination is optimized for expression in a host cell. An example of DNA which code for Factor B of SEQ ID NO: 6 and whose codon combination is optimized for expression in an insect cell is a DNA of SEQ ID NO: 9. Notably, the gene encoding the Factor B of the present invention and/or the gene encoding the Pro-clotting enzyme of the present invention may be a variant of a DNA in which the codon combination is optimized for expression in a host cell.

The Factor B of the present invention and the Pro-clotting enzyme of the present invention may each be a native protein or a recombinant protein.

A native Factor B and a native Pro-clotting enzyme may each be obtained from the hematocyte extract of the aforementioned various horseshoe crabs. These factors may be used after being purified to a desired extent. Purification may be performed through, for example, a known technique (Nakamura T. et al., J. Biochem. 1986 March; 99(3): 847-57).

The recombinant Factor B and the recombinant Pro-clotting enzyme may each be obtained through expression in a host cell. The host cell is not particularly limited, so long as a factor of interest can be expressed. For example, a host cell generally employed for heterologous protein expression may be used. Examples of the host cell include insect cells, animal cells, plant cells, yeast cells, and bacterial cells. Among them, an eukaryotic cell is preferred from the viewpoint of modification after translation. Specifically, an insect cell and an animal cell are more preferred.

Examples of the animal cells include mammalian cells. In the case where an animal cell such as a mammalian cell is used, the above descriptions about production of the Factor C of the present invention may also be applied mutatis mutandis to production of the Factor B and the Pro-clotting enzyme.

Examples of the insect cells include Sf9, Sf21, SF+, and High-Five. Of these, Sf9 is preferred as the insect cell.

The technique for expressing a factor of interest in an insect cell as a host is not particularly limited, so long as the factor can be expressed. For example, techniques generally employed for heterologous protein expression may be suitably used. For example, a factor of interest can be expressed by infecting an insect cell with a virus into which a gene encoding the factor has been incorporated (the technique being called a "virus method"). Also, for example, a factor of interest can be expressed by incorporating into an insect cell a vector into which a gene encoding the factor has been incorporated, to thereby incorporate the gene into a chromosome of the host cell (the technique being called a "stably expressing cell line method").

<Virus Method>

The virus employed in the virus method is not particularly limited, so long as an insect cell can be infected with the virus, to thereby express a factor of interest. A virus generally employed for protein expression in insect cells may be suitably used. Examples of such viruses include Baculovirus. Baculovirus is preferably Nucleopolyhedrovirus (NPV). Examples of NPV include *Autographa californica* NPV (AcNPV) and *Bombyx mori* NPV (BmNPV). NPV is preferably AcNPV.

Incorporation of a nucleic acid into a virus may be performed through a conventional method. For example, incorporation of a nucleic acid into a virus may be performed through homologous recombination by use of a transfer vector. Examples of the transfer vector include pPSC8 (product of Protein Sciences), pFastBac (product of Life technologies corporation), and pVL1393 (product of Pharmingen). Among them, pPSC8 is a preferable transfer vector.

An insect cell can be infected, through a conventional technique, with the virus into which a gene encoding a factor of interest has been incorporated, to thereby obtain the insect cell which retain the virus and express the factor.

<Stably Expressing Cell Line Method>

Through incorporation of a gene encoding a factor of interest into a chromosome of an insect cell, a stably expressing cell line which stably expresses the factor can be established. The method of establishing the stably expressing cell line is not particularly limited, and a conventional technique may be employed. For example, a stably expressing cell line can be established by use of pIZ-V5 (product of Life Technologies Corporation), according to a user's instruction attached thereto.

The conditions under which an insect cell is cultured are not particularly limited, so long as the insect cell can proliferate. Conditions generally employed in culturing insect cells may be employed, after appropriate modification has been performed, if needed. A culture medium which is generally employed in culturing insect cells may be employed as the culture medium in the invention. Examples of such a culture medium include a commercially available serum-free medium for culturing insect cells. Specifically, an Sf900III serum-free medium (product of Life Technologies Corporation) or the like may be suitably used. Culturing can be performed, for example, as shaking culture at 27° C. to 28° C.

Whether or not a factor of interest has been expressed can be confirmed by measuring activity of the factor. Expression of a factor of interest may also be confirmed by measuring the amount of mRNA formed via transcription of a gene encoding the factor, or detecting the factor through western blotting by use of an antibody.

The expressed factor can be recovered as a solution containing the factor, and can be used as a component of the endotoxin assay agent of the present invention. The solution containing the factor may be, for example, a culture broth, a culture supernatant, a disrupted cell extract, a mixture thereof, or the like. The factor may be used after being purified to a desired extent, or may be used without any purification. In the present invention, even when a cell culture supernatant containing the expressed factor is used as it is without any purification, satisfactory endotoxin assay performance can be attained. Purification of the factor may be performed through, for example, a known protein purification technique. Examples of such a technique include ammonium sulfate precipitation, gel filtration chromatography, ion exchange chromatography, hydrophobic interaction chromatography, hydroxyapatite chromatography, and so forth. In the case where a tag such as His-tag has been added to the factor, the factor may be purified through affinity chromatography based on affinity to the tag. A solution containing the factor may be used after being filtered by means of a filter. For example, a 0.22-μm filter can be used as the filter.

In the case each factor is produced through the virus method, the virus is preferably removed. The method of removing virus is not particularly limited, and a conventional technique may be employed. For example, the virus may be removed by means of a hollow fiber filtration membrane having a pore size of 500 kDa.

In the present invention, the Factor C of the present invention, the Factor B of the present invention, and the Pro-clotting enzyme of the present invention may be separately expressed in individually established expression cells.

The endotoxin assay agent of the present invention may contain, for example, only the Factor C of the present invention. Alternatively, the agent may contain, for example, only the Factor C of the present invention, the Factor B of the present invention, and the Pro-clotting enzyme of the present invention.

The endotoxin assay agent of the present invention may further contain a substrate for detecting the progress of the cascade reaction. As used herein, such a substrate may be referred to as a detection substrate.

Examples of the detection substrate include coagulogen. Coagulogen is a detection substrate with respect to Clotting enzyme, which is the final product of the cascade reaction. When coagulogen comes into contact with Clotting enzyme, a coagulated product, coagulin, is formed. The progress of the coagulation reaction can be determined by measuring the turbidity of the reaction mixture. Coagulogen can be recovered from a hematocyte extract of a horseshoe crab (i.e., lysate). Since the nucleotide sequence of the gene encoding coagulogen has been determined (Miyata et al, Protein Nucleic acid Enzyme, extra issue, No. 29; p. 30-43; 1986), coagulogen can also be produced genetically according to a conventional technique.

The detection substrate may be a synthetic substrate. The synthetic substrate is not particularly limited, so long as it has a property suitable for detection of the cascade reaction. Examples of the "property suitable for detection of the cascade reaction" include a property for detecting the presence of Clotting enzyme and a property for detecting an intermediate stage of the cascade reaction. Examples of the "property for detecting the presence of Clotting enzyme" include a property of coloring by catalytic reaction with the Clotting enzyme and a property of generating fluorescence by catalytic reaction with the Clotting enzyme. Examples of the "property for detecting an intermediate stage of the cascade reaction" include a property of coloring by catalytic reaction of a cascade reaction intermediate such as activated Factor C and a property of generating fluorescence by catalytic reaction of a cascade reaction intermediate such as activated Factor C. Examples of the synthetic substrate include a substrate represented by formula X-Y-Z (wherein X represents a protection group, Y represents a peptide, and Z represents a dye linked to Y via amide bond). When endotoxin is present in the reaction system, an amide linkage Y-Z is cleaved by the catalytic reaction of Clotting enzyme or an intermediate, which is yielded by the cascade reaction, to release the dye Z, whereby coloring occurs or fluorescence is generated. The protective group X is not particularly limited, and a known protective group for peptide may be suitably used. Examples of such a protective group include a t-butoxycarbonyl group and a benzoyl group. The dye Z is not particularly limited, and it may be a dye detectable under visible light or may be a fluorescent dye. Examples of the dye Z include p-nitroaniline (pNA), 7-methoxycoumarin-4-acetic acid (MCA), 2,4-dinitroaniline (DNP), and Dansyl dyes. Examples of the peptide Y include Leu-Gly-Arg (LGR), Ile-Glu-Gly-Arg (IEGR) (SEQ ID NO: 10), Val-Pro-Arg (VPR), and Asp-Pro-Arg (DPR). A synthetic substrate which reacts with the Clotting enzyme or the intermediate may be appropriately selected as the synthetic substrate in accordance with the mode of endotoxin assay. For example, from the viewpoint of substrate specificity, a substrate comprising LGR as peptide Y can be suitably used for detecting the Clotting enzyme, and a substrate comprising VPR or DPR as peptide Y can be suitably used for detecting activated Factor C. The released dye Z may be determined through a technique in accordance with the property of the target dye.

The endotoxin assay agent of the present invention may further contain an additional component other than the relevant factors and a detection substrate, so long as the assay agent can be used for endotoxin assay. The additional component is not particularly limited, and it may be selected in consideration of storage stability, handling easiness, stability of the factors and detection substrate, and so forth.

The endotoxin assay agent of the present invention may be formulated into any preparation such as solid, liquid, or gel. In the formulation process, additives such as an excipient, a binder, a disintegrant, a lubricant, a flavor/corrigent, a diluent, and a solvent, which are generally used in formulation, may be used. The endotoxin assay agent of the present invention as is may be used for endotoxin assay. Alternatively, the assay agent may be used for endotoxin assay after being diluted with or dispersed or dissolved in water, physiological saline, buffer, etc. Needless to say, the endotoxin assay agent of the present invention also encompasses such diluted, dispersed, dissolved, or similarly processed form of the agent.

In the endotoxin assay agent of the present invention, the factors and other components may be present as a mixture or present separately. For example, the factors may be mixed at any proportions in formulation, or individual factors may be formulated separately.

The concentrations of the factors and other components contained in the endotoxin assay agent of the present invention are not particularly limited. However, each concentration is preferably adjusted so as to fall within the below-mentioned suitable concentration range for assaying endotoxin. The concentration of each factor in the endotoxin assay agent of the present invention (as a solution prepared before contact with a test specimen) may be, for example, 5 to 200 µg/mL, and is preferably 20 to 100 µg/mL, more preferably 40 to 80 µg/mL, particularly preferably about 60 µg/mL. Also, the concentration of each factor in the endotoxin assay agent of the present invention may be adjusted in accordance with the method of producing the factor. When Factor C is produced with a rodent cell as a host, the concentration of Factor C in the endotoxin assay agent of the present invention (as a solution prepared before contact with a test specimen) can also be, for example, 5 to 200 µg/mL, 10 to 50 µg/mL, or 15 to 40 µg/mL. When Factor C is produced with a primate cell as a host, the concentration of Factor C in the endotoxin assay agent of the present invention (as a solution prepared before contact with a test specimen) can also be, for example, 5 to 200 µg/mL, 50 to 150 µg/mL, or 80 to 120 µg/mL. The above-exemplified concentrations may be calculated, for example, on the assumption that all the protein species present in the filtrate of a culture supernatant which has been obtained through expression of a factor of interest via the above-exemplified technique consists of the factor of interest.

The endotoxin assay agent of the present invention may be provided as an endotoxin assay kit. The endotoxin assay kit is not particularly limited, so long as the kit comprises the endotoxin assay agent of the present invention. The endotoxin assay kit may further comprise, for example, one or more elements selected from an endotoxin standard, a reaction container (e.g., a tube or a microplate), an instruction, and the like.

(4) Endotoxin Assay Method of the Present Invention

When a test specimen contains endotoxin, the cascade reaction proceeds by mixing the endotoxin assay agent of the present invention with the test specimen. Through measuring the progress of the cascade reaction, endotoxin contained in the test specimen can be measured. That is, the present invention provides a method for measuring endotoxin present in a test specimen, the method comprising a step of mixing the endotoxin assay agent of the present invention and the test specimen, and a step of measuring the progress of a cascade reaction. The method is also referred to as the "endotoxin assay method of the present invention."

In an embodiment of the endotoxin assay method of the present invention (hereinafter may be referred to as the "first embodiment"), all the factors are mixed with the test specimen. In the first embodiment, the factors contained the endotoxin assay agent of the present invention may be contained in the reaction system from the start of the step of mixing the endotoxin assay agent of the present invention with the test specimen, or may be successively added to the reaction system.

For example, the step of mixing the endotoxin assay agent of the present invention with the test specimen may comprise the following steps (A) to (C):

(A) a step of adding the Factor C of the present invention to the reaction system;

(B) a step of adding the Factor B of the present invention to the reaction system; and (C) a step of adding the Pro-clotting enzyme to the reaction system.

The steps (A) to (C) may be performed separately, partially simultaneously, or totally simultaneously. The steps (A) to (C) may be performed in any order. For example, the step (B) may be performed after the step (A), and the step (C) may be performed after the step (B).

In the first embodiment, the progress of the cascade reaction can be measured by adding a detection substrate to the reaction system and measuring the response (coloring, coagulation, etc.) of the substrate. The detection substrate may be contained in the reaction system from the start of the step of mixing the endotoxin assay agent of the present invention with the test specimen, or may be added to the reaction system during the progress of the step or after completion of the step. Needless to say, the first embodiment also encompasses an endotoxin assay method employing the endotoxin assay agent of the present invention which contains a detection substrate in advance.

In the endotoxin assay method of the present invention, so long as the cascade reaction proceeds when the test specimen contains endotoxin, the Factor B and the Pro-clotting enzyme of the present invention per se are not need to be in contact with the test specimen. That is, another embodiment of the endotoxin assay method of the present invention (hereinafter may be referred to as a "second embodiment") is a method for measuring endotoxin present in a test specimen, the method comprising the following steps (A) to (D):

(A) a step of mixing the Factor C of the present invention with the test specimen;

(B) a step of mixing the Factor B of the present invention with the Factor C after mixing of step (A);

(C) a step of mixing the Pro-clotting enzyme of the present invention with the Factor B after mixing of step (B); and (D) a step of measuring the progress of a cascade reaction.

In the second embodiment, the steps (A) to (D) may be performed separately, partially simultaneously, or totally simultaneously. For example, step A may be initiated, and then the Factor B and the Pro-clotting enzyme may be added to the reaction system during the progress of the step A or after completion of step A. Also, step B may be initiated, and then the Pro-clotting enzyme may be added to the reaction system during the progress of the step B or after completion of step B. Alternatively, all three factors may be incorporated into the reaction system from the start of step A. Still alternatively, the Factor C after the contact of step A may be recovered and used in step B, or the Factor B after the contact of step B may be recovered and used in step C.

In the second embodiment, the progress of the cascade may be measured by adding a detection substrate to the reaction system and measuring the response (coloring, coagulation, etc.) of the substrate. The detection substrate may be contained in the reaction system from the start of step A, or may be added to the reaction system during the progress of any step or after completion of any step.

Alternatively, endotoxin can be measured by detecting an intermediate stage of the cascade reaction. Specifically, endotoxin can be measured by detecting activated Factor C, which is an intermediate of the cascade reaction. That is, still another embodiment of the endotoxin assay method of the present invention (hereinafter may be referred to as a "third embodiment") may be a method for measuring endotoxin present in a test specimen, the method comprising a step of mixing the Factor C of the present invention with the test specimen and a step of detecting activated Factor C. In the third embodiment, the activated Factor C can be detected by adding a detection substrate to the reaction system and measuring the response (coloring, etc.) of the substrate. The detection substrate may be contained in the reaction system from the start of the step of mixing the Factor C of the present invention with a test specimen, or may be added to the reaction system during the progress of the step or after completion of the step.

The endotoxin assay method of the present invention, so long as the cascade reaction proceeds when the test specimen contains endotoxin, may further comprise any other arbitrary step. For example, the endotoxin assay method of the present invention may comprise a step of adding a detection substrate to the reaction system, or a step of mixing Clotting enzyme or an intermediate, which was yielded by the cascade reaction, with the detection substrate. Also, for example, the endotoxin assay method of the present invention may comprise a step of calculating the endotoxin level of the test specimen based on the reaction of the detection substrate.

In the endotoxin assay method of the present invention, reaction is preferably carried out in an aqueous medium such as water or a buffer.

In the assay method of the present invention, the concentration of each factor in the reaction mixture is not particularly limited, so long as the cascade reaction proceeds when the test specimen contains endotoxin. The concentration of each factor may be appropriately tuned in accordance with properties of the factor and so forth. For example, the concentration of each factor, as a final concentration, may be, for example, 2.5 to 100 µg/mL, and is preferably 10 to 50 µg/mL, more preferably 20 to 40 µg/mL, particularly preferably about 30 µg/mL. Also, the concentration of each factor in the reaction mixture may be adjusted in accordance with the method of producing the factor. When Factor C is produced with a rodent cell as a host, the concentration of Factor C in the reaction mixture, as a final concentration, may also be, for example, 2.5 to 100 µg/mL, 5 to 25 µg/mL, or 7.5 to 20 µg/mL. When Factor C is produced with a primate cell as a host, the concentration of Factor C in the reaction mixture, as a final concentration, may also be, for example, 2.5 to 100 µg/mL, 25 to 75 µg/mL, or 40 to 60 µg/mL. The above-exemplified concentrations may be calculated, for example, on the assumption that all the protein species present in the filtrate of a culture supernatant which has been obtained through expression of a factor of interest via the above-exemplified technique consists of the factor of interest.

In the assay method of the present invention, the concentration of the detection substrate in the reaction mixture is not particularly limited, so long as the cascade reaction proceeds when the test specimen contains endotoxin. The concentration of the detection substrate may be appropriately tuned in accordance with properties of the detection substrate and so forth. In the case where the detection substrate is a synthetic substrate, the concentration of the detection substrate is, for example, generally 0.001 mM to 100 mM, preferably 0.01 mM to 10 mM, as a final concentration.

In any embodiment, so long as the cascade reaction proceeds when the test specimen contains endotoxin, the reaction system may further contain any other arbitrary component, in addition to the factors, the detection substrate, and the test specimen.

The pH of the reaction mixture is not particularly limited, so long as the cascade reaction proceeds when the test specimen contains endotoxin. The pH of the reaction mixture may be appropriately tuned in accordance with properties of the factors. The pH of the reaction mixture is, for example, generally 5 to 10, preferably 7 to 8.5.

The reaction temperature is not particularly limited, so long as the cascade reaction proceeds when the test specimen contains endotoxin. The reaction temperature may be appropriately tuned in accordance with properties of the factors. The reaction temperature is, for example, generally 10° C. to 80° C., preferably 20° C. to 50° C. For example, the reaction temperature may be 37° C.

The reaction time is not particularly limited. The reaction time may be appropriately tuned in accordance with various conditions such as properties of the factors and reaction temperature. The reaction time is, for example, generally 5 minutes to 2 hours, preferably 15 minutes to 90 minutes. The reaction time may be, for example, 30 minutes to 40 minutes.

In any embodiment, the test specimen, the factors, and other components may be further added singly or in any combination to the reaction system during the course of reaction. These components may be added once or a plurality of times, or in a continuous manner. The reaction conditions may be constant from the start to the end of the reaction, or may be varied in the course of the reaction.

The progress of the cascade reaction attributable to the presence of endotoxin can be measured by measuring the response (coloring, coagulation, etc.) of the detection substrate, whereby endotoxin in the test specimen can be measured. The response (coloring, coagulation, etc.) of the detection substrate may be measured through a technique in accordance with the property of the detection substrate employed.

In the case of quantitatively measuring endotoxin, correlation data between endotoxin level and the extent of response (coloring, coagulation, etc.) of the detection substrate are obtained by use of an endotoxin standard sample with known concentration, and then the amount of endotoxin present in the specimen can be quantitatively determined on the basis of the obtained correlation data. The correlation data is, for example, a calibration curve. The quantitation may be carried out through a kinetic method or an end-point method.

The test specimen which can be subjected to endotoxin assay is not particularly limited. Examples of the specimen include water for medical use, pharmaceutical products, infusion solutions, blood products, medical apparatuses, medical instruments, cosmetics, foods and beverages, environmental specimens (e.g., air, river water, and soil), biological specimens (e.g., blood, body fluid, and tissue), native proteins, recombinant proteins, nucleic acids, and saccharides. The test specimen may be, for example, an injection. An injection refers to an agent that can be administered to the biological body via injection. Such an injection is not necessarily fluid during commercial distribution, and may be a lyophilized product. The test specimen itself, or an extract or wash liquid thereof may be mixed, dispersed, or dissolved in the reaction system, to thereby be subjected to endotoxin assay.

As described above, the Factor C of the present invention may have low susceptibility to inhibition of activity by an ion. Thus, in an embodiment of the present invention, endotoxin present in a test specimen containing an ion can be suitably measured.

In other words, the test specimen of the invention may be a test specimen containing an ion. The expression "containing an ion" refers to the state that the test specimen contains a substance which is present in the form of an ion during endotoxin assay. That is, "ion" referred to in the present invention may be species which are present inherently in an ionized form in the test specimen, or may be species which are present inherently in a salt form in the test specimen but are ionized during endotoxin assay. The type of ions is not particularly limited. An example of the ion is a cation, and an example of the cation is a metal ion. Examples of the metal ion include an alkali metal ion and an alkaline earth metal ion. Specific examples of the alkali metal ion and the alkaline earth metal ion include sodium ion, potassium ion, calcium ion, and magnesium ion. The contained amount of the ion in the test specimen may be such an amount that, for example, the concentration of the cation derived from the test specimen becomes 1 mM or higher, 2 mM or higher, 5 mM or higher, 10 mM or higher, 20 mM or higher, 50 mM or higher, or 100 mM or higher, as a final concentration in the reaction system after mixing the test specimen with the endotoxin assay agent. Specific examples of the salt include sodium chloride, magnesium sulfate, sodium hydrogencarbonate, sodium citrate, calcium chloride, potassium chloride, sodium iothalamate, calcium disodium edetate, and dihydrogen sodium phosphate. The contained amount of the salt in the test specimen may be such an amount that, for example, the concentration of the salt derived from the test specimen becomes 1 mM or higher, 2 mM or higher, 5 mM or higher, 10 mM or higher, 20 mM or higher, 50 mM or higher, or 100 mM or higher, as a final concentration in the reaction system after mixing the test specimen with the endotoxin assay agent. The test specimen may contain one kind of ion (or salt) or two or more kinds of ions (or salts).

EXAMPLES

The present invention will next be described more particularly by way of examples. However, these are merely examples of the present invention, and the scope of the present invention is not limited to these.
1. Preparation of Factor C Proteins
(1) Expression of Factor C in Insect Cells (Sf9)
In this section, Factor C was prepared by use of insect cell Sf9 as a host in the following manner.
A DNA encoding Factor C of Japanese horseshoe crab, *Tachypleus tridentatus*, was inserted between the EcoRV recognition site and the MluI recognition site of pIZ-V5 (product of Life Technologies Corporation), which is a vector for expression in insect cells, to thereby construct a Factor C expression plasmid. The nucleotide sequence of the DNA is shown in SEQ ID NO: 1, and the amino acid sequence of Factor C encoded by the DNA is shown in SEQ ID NO: 2 (the same applies throughout the Example).
The Factor C expression plasmid was introduced into cultured Sf9 cells through transfection by use of Celfectin reagent (product of Life Technologies Corporation). The Sf9 cells were statically cultured at 28° C. in an Sf900 III serum-free medium (product of Life Technologies Corporation) containing 300 to 600 µg/mL Zeocin (product of Life Technologies Corporation), whereby Sf9 strains into which the genome the expression plasmid had been incorporated were selected.
Candidates for Sf9 in which the Factor C gene had been stably expressed were isolated through the cloning cylinder technique, and a plurality of Sf9 cell lines was cloned. The thus-obtained clones were individually cultured, to thereby obtain culture supernatants. Secretion of the recombinant Factor C protein in each culture supernatant was confirmed through western blotting by use of an anti-Factor C antibody (2C12 antibody; Yoshiki Miura, et al., J. Biochem. 112: 476-481 (1992)). Also, activity of Factor C (property of being activated by endotoxin) in the culture supernatant was confirmed through activity measurement by use of a synthetic substrate Boc-LGR-pNA. Notably, the procedure of activity measurement is described in "4. Activity measurement" below (the same applies throughout the Example). Based on the results of western blotting and activity measurement, an Sf9 cell line highly expressing Factor C was selected.
The Sf9 cell line highly expressing Factor C was suspension-cultured (28° C.) in an Sf900 III medium containing 1x penicillin/streptomycin (product of Life Technologies Corporation) and 50 µg/mL Zeocin to a later phase of the logarithmic growth phase (6 to $8\times10^6$ cells/mL). Then, the culture was centrifuged (3,000×g, 30 minutes, 4° C.), to thereby recover a culture supernatant. The supernatant was filtered through a 0.22-µm filter, and the thus-recovered fraction (i.e. filtrate) was employed as recombinant Factor C (Sf9).
(2) Expression of Factor C in Mammalian Cells (CHO DG44)
In this section, Factor C was prepared by use of CHO DG44, which is a Chinese hamster ovary cell line, as a host through the following procedure.
A DNA encoding Factor C of Japanese horseshoe crab, *Tachypleus tridentatus*, was inserted between the EcoRI recognition site and the XbaI recognition site of pCI-neo (product of Promega), which is a vector for expression in mammalian cells, to thereby construct a Factor C expression plasmid. A kozak sequence (GCCACC) was added just before the start codon of Factor C.
The Factor C expression plasmid and a dhfr expression plasmid were incorporated into cultured CHO DG44 cells through simultaneous transfection using a lipofection reagent (Lipofectamine LTX) (product of Life Technologies Corporation). The CHO DG44 cells were statically cultured at 37° C. under feeding of 5% $CO_2$ in an RPMI 1640 medium (5% dialyzed serum, containing 1×penicillin/streptomycin) (product of Sigma) added with 1 mg/mL Geneticin (product of Life Technologies Corporation), whereby CHO DG44 strains into which the genome the expression plasmids had been incorporated were selected.
Fifteen days after the simultaneous transfection, MTX (methotrexate) (product of Wako Pure Chemical Industries, Ltd.) was added to the culture medium. The MTX concentration was elevated stepwise from 50 nM to 5,000 nM over three months, and CHO DG44 cell lines highly expressing Factor C were selected as polyclones. Effective amplification of the incorporated Factor C gene by virtue of MTX was confirmed by detecting Factor C in a culture supernatant through western blotting using a 2C12 antibody, and quantitating the transcriptional amount of mRNA of Factor C through real-time PCR.
The group of polyclonal CHO DG44 cell lines highly expressing Factor C was diluted by the medium to obtain a cell concentration of 0.5 cells/well, and the dilute was inoculated to a 96-well plate. From about 10 to 20 days after inoculation, the formed cell colonies were successively subjected to expansion culture, whereby CHO DG44 cell lines highly expressing Factor C were cloned. The transcriptional amount of mRNA of Factor C was confirmed through real-time PCR. The amount of Factor C protein secreted to the medium was confirmed through western blotting using a 2C12 antibody. The Factor C activity (property of being activated by endotoxin) in the culture supernatant was confirmed through activity measurement using a synthetic substrate Boc-LGR-pNA. Based on these results, a monoclonal CHO DG44 cell line highly expressing Factor C was selected.

The CHO DG44 cell line highly expressing Factor C (monoclonal) was conditioned in a serum-free complete synthetic medium containing 5 μM MTX and thus floated. The cell line was grown at 37° C. under feeding of 5% $CO_2$ to a later phase of the logarithmic growth phase. The thus-obtained floating culture broth was centrifuged (3,000× g, 30 minutes, 4° C.), to thereby recover a culture supernatant. The supernatant was filtered through a 0.22-μm filter, and the thus-recovered fraction (i.e. filtrate) was employed as recombinant Factor C (CHO).

(3) Expression of Factor C in Mammalian Cells (HEK293)

In this section, Factor C was prepared by use of HEK293, which is a human embryo kidney cell line, as a host through the following procedure.

A DNA encoding Factor C of a Japanese horseshoe crab, Tachypleus tridentatus, was inserted between the EcoRI recognition site and the XhoI recognition site of pCA7 (Makoto Takeda, et al., J. Viol. 79 (22): 14346-54 (2005)), which is a vector for expression in mammalian cells, to thereby construct a Factor C expression plasmid. A kozak sequence (GCCACC) was added just before the start codon of Factor C.

The Factor C expression plasmid was incorporated into cultured HEK293 cells through transfection using polyethylenimine (product of Sigma) (Hashiguti et al., Expression of Recombinant Protein Using Cultured Human Cells—Standard Protocol by 293-type cells-, PSSJ Archives, 1, e017 (2008); available on the world wide web at pssj.jp/archives/Protocol/Expression/293_01/293_01_01.html.

HEK293 cells were statically cultured in a DMEM medium (containing 10% fetal bovine serum and 2 mM L-glutamine) (product of Sigma) at 37° C. under feeding of 5% $CO_2$ without replacement of the medium. Four days after transfection, the culture broth was recovered, and was centrifuged (3,300×g, 30 minutes, 4° C.), to thereby recover a culture supernatant. The supernatant was filtered through a 0.22-μm filter, and the thus-recovered fraction (i.e. filtrate) was employed as recombinant Factor C (HEK).

(4) Preparation of Native Factor C (Derived from Amebocyte of Tachypleus tridentatus)

A fraction containing Factor B and Factor C was recovered from an amebocyte extract of Japanese horseshoe crab, Tachypleus tridentatus, through column chromatography by use of dextran sulfate resin (Takanori Nakamura, et al., Eur. J. Biochem. 154: 511-521 (1986)). The fraction (5 mL) was subjected to gel filtration by means of a column (φ2.2 cm×97 cm) filled with Sepharose CL6B gel (product of GE Healthcare). Gel filtration was performed under almost the same conditions as employed in a known technique (Jeak Ling Ding and Bow Ho, U.S. Pat. No. 5,712,144; Jeak L. Ding, et al., Biochem. Biophys. Acta 1202: 149-156). The flow rate was adjusted to 15 mL/h, and 50 mM Tris buffer (pH 8.0) containing 154 mM NaCl, 1 mM EDTA, and 5% DMSO was employed as a solvent.

Gel filtration eluted fractions (3.7 mL/tube, 150 tubes) were subjected to SDS-PAGE followed by CBB staining and western blotting using a 2C12 antibody, and activity measurement using a synthetic substrate Boc-LGR-pNA, whereby fractions containing Factor C protein were identified. These fractions containing the purified Factor C protein were employed as native Factor C (TAL).

2. Preparation of Recombinant Factor B and Recombinant Pro-Clotting Enzyme

A DNA encoding Factor B of Japanese horseshoe crab, Tachypleus tridentatus, was inserted between the EcoRV recognition site and the MluI recognition site of pIZ-V5 (product of Life Technologies Corporation), which is a vector for expression in insect cells, to thereby construct a Factor B expression plasmid. The nucleotide sequence of the DNA is shown in SEQ ID NO: 9, and the amino acid sequence of Factor B encoded by the DNA is shown in SEQ ID NO: 6. Notably, the nucleotide sequence shown in SEQ ID NO: 9 is a nucleotide sequence optimized for expression in insect cells.

A DNA encoding Pro-clotting enzyme of Japanese horseshoe crab, Tachypleus tridentatus, was inserted between the EcoRV recognition site and the MluI recognition site of pIZ-V5 (product of Life Technologies Corporation), which is a vector for expression in insect cells, to thereby construct a Pro-clotting enzyme expression plasmid. The nucleotide sequence of the DNA is shown in SEQ ID NO: 7, and the amino acid sequence of Pro-clotting enzyme encoded by the DNA is shown in SEQ ID NO: 8.

Through the same method as employed in the case of Factor C, the expression plasmids were each incorporated into Sf9 cells, high-expression clones were selected, and culture supernatants thereof were prepared. The culture supernatants were individually filtered through a 0.22-μm filter, and the obtained fractions (i.e. filtrates) were employed as a recombinant Factor B and a recombinant Pro-clotting enzyme. Recovery of the factors was confirmed through western blotting employing an antibody specific to each factor and activity measurement.

3. Comparison of Molecular Weights of Factor C Proteins (1)

The molecular weights of the above-prepared four types of Factor C proteins were compared with one another through SDS-PAGE and western blotting.

Firstly, each Factor C in an amount shown in FIG. 2 was subjected to SDS-PAGE under a non-reducing condition employing a 5 to 20% gradient gel. In FIG. 2, Sf9, CHO, and HEK denote the Factor C expressed in Sf9 cells, CHO DG44 cells, and HEK293 cells, respectively, and TAL refers to native Factor C (hereinafter the same applies). Notably, Factor C is cleaved into an H chain and an L chain under reducing conditions. In the present Example, SDS-PAGE was carried out under a non-reducing condition in order to compare the molecular weights of Factor C in an intact state.

After SDS-PAGE, proteins were transferred to a PVDF membrane (product of Bio RAD) by means of a semi-dry blotter. The PVDF membrane was recovered and blocked with 5% skim milk, and then sequentially treated with a primary antibody (2C12 antibody) and a secondary antibody (HRP-labeled anti-mouse goat antibody) (product of Dako). Bands attributed to Factor C were made to emit light with a detection reagent, SuperSignal West Dura (product of Thermo Scientific), and the light emission was recorded by a CCD camera.

The four types of Factor C were found to have different molecular weights, and the molecular weight was the greatest in the case of CHO, followed by TAL, HEK, and Sf9 in the descending order (FIG. 2).

Regarding Singaporean horseshoe crab, Carcinoscorpius rotundicauda, it has been reported that all of the native Factor C protein purified from an amebocyte extract, and recombinant Factor C proteins produced in insect cells Sf9 and S2, and in African green monkey kidney cell line COS-1 as a host cell have the same molecular weight of 132 kDa (Jeak Ling Ding and Bow Ho, U.S. Pat. No. 5,712,144, and Jeak L. Ding, et al., Biochem. Biophys. Acta 1202: 149-156 (1993) (for native Factor C protein); Jing Wang, et al., J. Biol. Chem. 277(39): 36363-72 (2002) (for Sf9 and S2); and Roopashree S. Dwarakanath, et al., Biotechnology letters 19(4): 357-361 (1997) (for COS-1)).

Thus, among the above-prepared four types of Factor C, the molecular weight of each of CHO and TAL was correctly measured. Firstly, recombinant Factor C (CHO) was purified in a manner similar to that employed in the case of native Factor C (TAL). Then, electrophoresis (15% gel, LMW Marker kit (product of GE Healthcare)) was performed under the same conditions as employed in a known technique (Jeak Ling Ding and Bow Ho, U.S. Pat. No. 5,712, 144; and Jeak L. Ding, et al., Biochem. Biophys. Acta 1202: 149-156), and the molecular weight of each Factor C was then determined through Ferguson plotting. As a result, recombinant Factor C (CHO) was found to have a molecular weight of 126 kDa, and native Factor C (TAL) was found to have a molecular weight of 123 kDa (FIG. 3). Thus, native Factor C (TAL) and recombinant Factor C (CHO) derived from Japanese horseshoe crab, *Tachypleus tridentatus*, were found to have a molecular weight smaller than that of the Factor C derived from Singaporean horseshoe crab, *Carcinoscorpius rotundicauda* (132 kDa).

The difference in molecular weight among the above-prepared four types of Factor C is conceived to be attributed to the difference in post-translation modification (sugar chain modification) depending on the type of host cells employed. For example, it has been known that sialic acid is linked to the N-type sugar chain after translation in mammalian cells, whereby a recombinant protein produced in mammalian cells has dimensions larger than those of a recombinant protein produced in insect cells (Robert L. Harrison and Donald L. Jarvis, Methods in Molecular Biology 338: 341-356 (2007)). This supports the results of the present Example (FIG. 2).

4. Activity Measurement

Each of the above-prepared four types of Factor C was combined with other factors, and activity measurement was carried out through the following procedure. FIG. 4 shows the scheme of activity measurement.

As shown in FIG. 4, common materials other than Factor C (a recombinant Factor B, a recombinant Pro-clotting enzyme, a synthetic substrate Boc-LGR-pNA, and Tris buffer) were mixed together, to thereby prepare a common liquid mixture. To the common liquid mixture, Factor C in an amount specified in FIG. 6 was added, and the total volume was adjusted to 50 µL. The thus-obtained mixture was mixed with 50 µL of a specimen (water containing United States Pharmacopoeia standard endotoxin (USP-RSE) (product of Seikagaku corporation)), and the resultant mixture was heated at 37° C. for 30 minutes. In this assay system, Factor C is activated by endotoxin, to thereby form activated Factor C; Factor B is activated by the activated Factor C, to thereby form activated Factor B; Pro-clotting enzyme was activated by the activated Factor B, to thereby form a corresponding Clotting enzyme; and the Clotting enzyme cleaves a synthetic substrate Boc-LGR-pNA, whereby p-nitroaniline is released (FIG. 5). The change in absorbance (A 405 nm) attributed to formation of p-nitroaniline was measured in a time-dependent manner, and the absorbance change rate per unit time (mAbs/min) was calculated and employed as Factor C activity. The Measurement was conducted thrice for each sample.

In the above assay system, the final concentration of each factor was as follows: recombinant Factor B 30 µg/mL, recombinant Pro-clotting enzyme 30 µg/mL, recombinant Factor C (Sf9) 11.3 µg/mL, recombinant Factor C (CHO) 12 µg/mL, recombinant Factor C (HEK) 51.5 µg/mL, and Factor C (TAL) 0.25 µg/mL. The above-exemplified concentrations (except for the case of TAL) were calculated, on the assumption that all the protein species present in the sample (i.e. filtrate) prepared through expression of a factor of interest consisted of the factor of interest. The Factor C (TAL) concentration was measured after purification of Factor C (TAL).

As a result, reconstituted systems each exhibiting almost equivalent activity were successfully constituted for the four types of Factor C (FIG. 6). In each reconstituted system, the activity was increased with an increase in endotoxin concentration (0.05 and 0.1 EU/mL) of a specimen.

The recombinant Factor C derived from *Carcinoscorpius rotundicauda* and produced in mammalian cell COS-1 (132 kDa) is reported to be recovered in an insoluble fraction (Roopashree S. Dwarakanath, et al., Biotechnology letters 19(4): 357-361 (1997); and Jing Wang, Bow Ho and Jeak L. Ding, Biotechnology letters 23: 71-76 (2001)). Also, the recombinant Factor C derived from *Carcinoscorpius rotundicauda* and produced in insect cell S2 (132 kDa) is reported to exhibit no protease activity in response to endotoxin (Jing Wang, et al., J. Biol. Chem. 277(39): 36363-72 (2002)). Lack of activity of the latter Factor C (produced in S2) is thought to be attributed to the difference in sugar chain structure from the native Factor C derived from *Carcinoscorpius rotundicauda* and the recombinant Factor C produced in insect cell Sf9, due to difference in reactivity to lectin.

Meanwhile, in the present Example, it was found that the recombinant Factor C derived from *Tachypleus tridentatus* (Sf9, CHO, and HEK) exhibited an endotoxin-dependent activity, even though the molecular weight thereof differs from that of native Factor C (TAL); i.e., even though the sugar chain structure thereof differs from that of native Factor C (TAL).

5. Inhibition of Activity by Injection

Endotoxin is a strong immune reaction-inducing substance. Thus, when an injection contaminated with endotoxin is administered to the body, a grave side effect occurs. Therefore, in production of injections, detection of endotoxin by use of a limulus amebocyte lysate reagent is obligated by the pharmacopoeia of the relevant country, to thereby confirm no endotoxin contamination.

Thus, the above-prepared four types of Factor C were compared in terms of reactivity to endotoxin in various injections.

As a control specimen, injection water containing endotoxin (endotoxin concentration: 0.05 EU/mL) was used. Measurement specimens used were as follows: 4-fold dilute of 10 w/v % sodium chloride injection (10% sodium chloride injection, product of Otsuka Pharmaceutical Co., Ltd.); 16-fold dilute of 0.5 M magnesium sulfate injection (Mg sulfate corrective injection 1 mEq/mL, product of Otsuka Pharmaceutical Co. Ltd.); undiluted solution of physiological saline (Otsuka isotonic sodium chloride solution, product of Otsuka Pharmaceutical Co., Ltd.); 8-fold dilute of 7 w/v % sodium hydrogencarbonate injection (Meylon injection 7%, product of Otsuka Pharmaceutical Co., Ltd.); 8-fold dilute of 10 w/v % sodium citrate injection (sodium citrate injection for transfusion, product of Fuso Pharmaceutical Industries, Ltd.); 100-fold dilute of 0.5 M calcium chloride injection (Ca chloride corrective injection 1 mEq/mL, product of Otsuka Pharmaceutical Co., Ltd.); undiluted solution of Ringer's solution (Ringer's solution "Fuso", product of Fuso Pharmaceutical Industries, Ltd.); and 16-fold dilute of sodium iothalamate injection (Conray 400 injection, product of Daiichi Sankyo Co., Ltd.), each spiked with endotoxin (endotoxin concentration: 0.05 EU/mL). When the measurement specimen was 8-fold dilute of 10 w/v % sodium citrate injection, the final sodium citrate concentration was about 21 mM. When the measurement specimen was 8-fold dilute of 7 w/v % sodium hydrogencarbonate injection, the final sodium hydrogencarbonate concentration was about 52 mM. When the measurement specimen was 4-fold dilute of 10 w/v % sodium chloride injection, the final sodium chloride concentration was about 214 mM. When the measurement specimen was undiluted solution of physiological saline, the final sodium chloride concentration was about 77 mM. When the measurement specimen was 16-fold dilute of 0.5 M magnesium sulfate injection, the final magnesium sulfate concentration was about 16 mM. When the measurement specimen was 100-fold dilute of 0.5 M calcium chloride injection, the final calcium chloride concentration was about 2.5 mM. Activity of Factor C was measured through the procedure shown in FIG. 4. A residual activity was defined as a relative reactivity (%) for endotoxin in an injection specimen, with respect to the reactivity for endotoxin in the corresponding control specimen as 100%. The measurement was carried out four times for each injection specimen.

FIG. 7 shows the results. When a typical injection was employed as a measurement specimen, reaction with endotoxin was inhibited, as compared with the case in which injection water was used. The degree of inhibition varied in accordance with the type of injection and the type of host for expressing Factor C. Recombinant Factor C (CHO) and recombinant Factor C (HEK) showed a tendency to have low susceptibility to reaction inhibition to all the tested injections, as compared with native Factor C (TAL). Particularly, recombinant Factor C (CHO) exhibited the highest residual activity in many cases. In contrast, recombinant Factor C (Sf9) was most susceptible to reaction inhibition in many injections (7 injections except sample No. 6).

The test results indicate that Factor C expressed in mammalian cells can have low susceptibility to activity inhibition by ions. Such a property is particularly advantageous for detection of endotoxin contamination in production of injections.

6. Preparation of L Chain-Specific Factor C Protein Antibody

A Factor C protein is known to be present as a single chain (Full chain) under non-reducing conditions, and to be cleaved into two chains (H chain and L chain) under reducing conditions. The anti-Factor C monoclonal antibody (2C12 antibody) is reported to recognize the Full chain and the H chain (Yoshiki Miura, et al., J. Biochem. 112: 476-481(1992)). Thus, a peptide antigen present in the L chain was produced. A rabbit was immunized with the peptide antigen through a conventional method, whereby a polyclonal antibody which can recognize the L chain and the Full chain (FCL antibody) was produced (FIG. 10).

7. Purification of Recombinant Factor C Proteins

According to the method employed in "(4) Preparation of native Factor C (derived from *Tachypleus tridentatus*)" of "1. Preparation of Factor C proteins", three types of recombinant Factor C proteins were purified from culture supernatants of mammalian cells (CHO DG44, and HEK293) and insect cells (Sf9). Briefly, each supernatant (100 to 300 mL) was subjected to column chromatography by use of dextran sulfate resin, and elution fractions containing the corresponding recombinant Factor C were isolated through gel filtration. Purification of the recombinant Factor C proteins was confirmed through SDS-PAGE and CBB staining, western blotting employing the 2C12 antibody, and activity measurement.

8. Comparison of Molecular Weights of Factor C Proteins (2)

The molecular weights of the above-purified four types of Factor C proteins were compared again with one another through SDS-PAGE and western blotting.

The four types of purified Factor C proteins, derived from a native horseshoe crab (TAL), a culture supernatant of CHO DG44 (CHO), a culture supernatant of HEK293 (HEK), and a culture supernatant of Sf9 (Sf9), were applied to a single gel (15% gel) for SDS-PAGE, and subjected to CBB staining (FIG. 11). Each of the four types of purified Factor C proteins presented as a single chain (Full chain) under non-reducing conditions, and was cleaved into two chains (H chain and L chain) under reducing conditions. After transfer to the PVDF membrane, western blotting was performed by use of the 2C12 antibody and the FCL antibody (FIG. 12). In relation to antibody recognition sites (FIG. 10), the 2C12 antibody specifically recognized the Full chain and the H chain, and the FCL antibody specifically recognized the Full chain and the L chain. The CBB-stained bands shown in FIG. 11 were identified to bands derived from Factor C. Regarding molecular weight of Factor C, CHO had the largest molecular weight; TAL and HEK had almost the same molecular weight; and Sf9 has the smallest molecular weight, in all cases of the Full chain under non-reducing conditions and of the H-chain and L chain under reducing conditions.

In order to more precisely compare the molecular weights of the four types of purified Factor C, electrophoresis (15% gel, LMW marker (product of GE Healthcare)) was performed under the same conditions as employed in a known technique (Jeak Ling Ding and Bow Ho, U.S. Pat. No. 5,712,144; and Jeak L. Ding, et al., Biochem. Biophys. Acta 1202: 149-156), followed by CBB staining, and the molecular weights were then determined through Ferguson plotting.

Table 1 shows the results. Under non-reducing conditions, TAL had a molecular weight of 124 kDa, which is almost equivalent to 123 kDa reported by the reference. The molecular weight of CHO was higher, 128 kDa, and that of HEK was 124 kDa, which is equivalent to that of TAL. The molecular weight of Sf9 was 109 kDa, which is smaller than that of TAL. As a result, when recombinant Factor C was expressed in insect cells (Sf9), the molecular weight thereof was found to be smaller than that of native Factor C (TAL), whereas when recombinant Factor C was expressed in mammalian cells (CHO, HEK), the molecular weight thereof was found to be equivalent to or larger than that of native Factor C (TAL). This tendency was also confirmed in the case of the H chain or the L chain under reducing conditions.

The molecular weight of native Factor C derived from *Carcinoscorpius rotundicauda* (Singaporean horseshoe crab) and that of recombinant Factor C thereof obtained via gene expression in insect cells have been reported to be the same value, 132 kDa, under non-reducing conditions. The four types of purified Factor C derived from *Tachypleus tridentatus* (Japanese horseshoe crab) and obtained in the present Example were found to have a molecular weight smaller than 132 kDa (Table 1).

TABLE 1

| Species of horseshoe crab | Source | Mol. wt. (kDa) Full | H | L | Reference |
|---|---|---|---|---|---|
| Tachypleus tridentatus | Natural lysate | 124 | 85 | 42 | Present Example |
| Tachypleus tridentatus | CHO DG44 | 128 | 88 | 43 | Present Example |
| Tachypleus tridentatus | HEK293 | 124 | 85 | 42 | Present Example |
| Tachypleus tridentatus | Sf9 | 109 | 75 | 39 | Present Example |
| Tachypleus tridentatus | Natural lysate | 123 | 80 | 43 | Takanori Nakamura, et al., Eur. J. Biochem. 154: 511-521 (1986) |
| Carcinoscorpius rotundicauda | Natural lysate | 132 | 80 | 52 | Jeak L. Ding, et al., Biochem. Biophys. Acta 1202: 149-156 (1993) |
| Carcinoscorpius rotundicauda | Sf9 (+baculo virus) | 132 | No data | No data | Jing Wang, et al., J. Biol. Chem. 277 (39): 36363-72 (2002) |
| Carcinoscorpius rotundicauda | S2 | 132 | No data | No data | Jing Wang, et al., J. Biol. Chem. 277 (39): 36363-72 (2002) |

9. Confirmation of N-Type Sugar Chain Modification

The genes employed in the present Example for expressing the recombinant Factor C were sequences all derived from *Tachypleus tridentatus*, and the expression plasmids were designed so that no tag was added to any terminus of each sequence. Therefore, the translated amino acid sequences of the four types of Factor C obtained in the present Example are thought to be the same one. In addition, the partial sequences of the N-terminal amino acid residues of the recombinant Factor C (HEK, Sf9) were determined. These amino acid sequences are identical to the sequence of the native Factor C of *Tachypleus tridentatus*, reported by the reference (data not shown).

Generally, the molecular weight of protein is thought to vary considerably by modification after translation. In addition, it has also been reported that the structure of an N-type sugar chain added to protein through modification after translation differs between the case of insect cells and the case of mammalian cells. Thus, in order to confirm whether the above-observed difference in molecular weight among the purified Factor C proteins is attributed to the difference in N-type sugar chain structure, the Factor C proteins each were treated with glycopeptidase F. This enzyme is known to cleave and remove an N-type sugar chain added to protein. Therefore, when the purified Factor C proteins have the same molecular weight after treatment with the enzyme, N-type sugar chain is conceived to induce the difference in molecular weight among the Factor C proteins.

According to an attached instruction, each purified Factor C protein (1 µg) was treated with 1 mU glycopeptidase F (product of Takara) under modification conditions in the presence of SDS and a reducing agent. The thus-treated samples were separated through SDS-PAGE, and then analyzed through western blotting. FIG. 13 shows the results. In all cases of the four types of Factor C, the molecular weight of H chain decreased by the glycopeptidase treatment and became the same value. By contrast, although the molecular weight of L chain decreased after the glycopeptidase treatment in all cases of the four types of Factor C, the molecular weight became the same value only in the cases of CHO, HEK, and TAL. Specifically, among four types of L chains, the L chain of the Factor C derived from Sf9 was found to have a molecular weight larger than that of the other three cases, after the glycopeptidase treatment. Therefore, in the L chain of the Factor C derived from Sf9, a certain modification other than N-type sugar chain modification was conceived to occur, after translation.

Thus, the aforementioned analysis indicates that the difference in mode of N-type sugar chain after translation plays a main role in providing the difference in molecular weight of Factor C.

10. Analysis of N-Type Sugar Chain of Factor C

In N-type sugar chain modification of a protein in mammalian cells, sugar molecules are stepwise added to an asparagine residue of the protein, and eventually, a sugar chain containing terminal sialic acid (i.e., complex-type) is formed. In contrast, in insect cells, sialic acid is not generally added, and a sugar chain having a mannose terminus (i.e., paucimannose-type) is formed (Robert L. Harrison and Donald L. Jarvis, Methods in Molecular Biology 338: 341-356 (2007)). In order to confirm the difference in N-type sugar chain structure among the four types of purified Factor C proteins, lectin blotting was performed by use of various lectins such as terminal sialic acid-specific lectins (e.g., *Maackia amurensis* agglutinin (MAM) and *Sambucus sieboldiana* agglutinin (SSA)).

Dilution series (100, 25, and 6 ng) samples of each of the four types of purified Factor C and bovine fetuin protein as a positive control were dot-blotted onto a nitrocellulose membrane, and the membrane was blocked with 3% BSA. Then, the membrane was sequentially reacted with biotin-labeled lectin (product of J-Oil Mills, Inc.) and streptavidin-labeled HRP (product of Thermo Scientific). Light emission attributed to decomposition of the HRP substrate (product of Thermo Scientific) was detected. Instead of lectin, a 2C12 anti-Factor C antibody was used as a control, to thereby confirm that the same amounts of four types of Factor C were blotted.

FIG. 14(a) shows the results of lectin blotting, and FIG. 14(b) shows the binding specificity of lectins employed. *Lens culinaris* agglutinin (LCA) (fucose-specific lectin) and *Canavalia ensiformis* agglutinin (Con A) (bi-antenna-type, high-mannose-type, and complex-type sugar chain-specific lectin) were bonded to all the samples; i.e., four types of Factor C and fetuin. In contrast, MAM (($\alpha$-2,3)-linked terminal sialic acid-specific lectin) was strongly bonded to CHO and less strongly bonded to HEK. TAL and fetuin have almost the same weak reactivity, but did not react with Sf9. SSA ((α-2,6)-linked terminal sialic acid-specific lectin) reacted with HEK, TAL, and fetuin, but did not react with CHO and Sf9.

The above analysis indicates that the N-type sugar chain of recombinant Factor C expressed in mammalian cells (CHO and HEK) contains (α-2,3)-linked terminal sialic acid, and that the N-type sugar chain of recombinant Factor C expressed in insect cells (Sf9) contains no (α-2,3)-linked terminal sialic acid. FIG. 14(c) shows schematic structures of the N-type sugar chain of recombinant Factor C, estimated by the results of the above experiments and reports by the reference. The results of the above experiments support that the difference in mode of N-type sugar chain modification after translation is mainly attributed to the difference in molecular weight of Factor C.

INDUSTRIAL APPLICABILITY

According to the present invention, a recombinant horseshoe crab Factor C can be efficiently produced. In an embodiment of the present invention, endotoxin present in a test specimen containing an ion can be measured, while inhibition of reaction is reduced.

SEQUENCE LISTING

SEQ ID NO: 1: DNA sequence of the Factor C gene of Japanese horseshoe crab
SEQ ID NO: 2: Amino acid sequence of the Factor C of Japanese horseshoe crab
SEQ ID NO: 3: DNA sequence of the Factor C gene of Southeast Asian (Singaporean) horseshoe crab
SEQ ID NO: 4: Amino acid sequence of the Factor C of Southeast Asian (Singaporean) horseshoe crab
SEQ ID NO: 5: DNA sequence of the Factor B gene of Japanese horseshoe crab
SEQ ID NO: 6: Amino acid sequence of the Factor B of Japanese horseshoe crab
SEQ ID NO: 7: DNA sequence of the Pro-clotting enzyme gene of Japanese horseshoe crab
SEQ ID NO: 8: Amino acid sequence of the Pro-clotting enzyme of Japanese horseshoe crab
SEQ ID NO: 9: DNA sequence of a Factor B gene of Japanese horseshoe crab, the gene having a codon optimized for expression in insect cells
SEQ ID NO: 10: Peptide sequence

What is claimed is:

1. A horseshoe crab Factor C protein having activity of Factor C,
wherein the horseshoe crab is selected from the group consisting of *Tachypleus tridentatus*, and *Limulus polyphemus*, and wherein the horseshoe crab Factor C protein is produced through being recombinantly expressed from a Chinese Hamster Ovary (CHO) DG44 cell or Human Embryonic Kidney (HEK) 293 cell, and
wherein the Factor C protein contains ($\alpha$-2,3)-linked terminal sialic acid in a greater amount, as compared with a corresponding native horseshoe crab Factor C and/or a corresponding Factor C protein recombinantly expressed using Sf9 as a host cell.

2. A Factor C protein having activity of Factor C,
wherein the Factor C protein is produced through being recombinantly expressed from a Chinese Hamster Ovary (CHO) DG44 cell or Human Embryonic Kidney (HEK) 293 cell, and
wherein the expressed Factor C protein comprises an amino acid sequence selected from the group consisting of:
(A) the amino acid sequence of SEQ ID NO: 2, and the Factor C protein contains ($\alpha$-2,3)-linked terminal sialic acid in a greater amount, as compared with a native horseshoe crab Factor C of *Tachypleus tridentatus* and/or a corresponding Factor C protein recombinantly expressed using Sf9 as a host cell; and
(B) an amino acid sequence having 90% or higher sequence identity to the amino acid sequence of SEQ ID NO:2, and having activity of Factor C, and the Factor C protein contains ($\alpha$-2,3)-linked terminal sialic acid in a greater amount, as compared with a native horseshoe crab Factor C of *Tachypleus tridentatus* and/or a corresponding Factor C protein recombinantly expressed using Sf9 as a host cell; and
wherein the Factor C protein exhibits a residual activity of at least one selected from the group consisting of:
(1) 10% or higher in the presence of 21 mM sodium citrate; and
(2) 15% or higher in the presence of 16 mM magnesium sulfate.

3. The Factor C protein according to claim 2, which is water soluble.

4. The Factor C protein according to claim 2, which has a molecular weight of 115 kDa to 140 kDa as measured by SDS-PAGE under non-reducing condition.

5. The Factor C protein according to claim 4, which has a molecular weight of 127 kDa±5 kDa.

6. The Factor C protein according to claim 2, which exhibits a residual Factor C activity of 35% or higher in the presence of 52 mM sodium hydrogen carbonate.

7. The Factor C protein according to claim 2, which exhibits a residual Factor C activity of 35% or higher in the presence of 214 mM sodium chloride.

8. The Factor C protein according to claim 2, which exhibits a residual Factor C activity of 25% or higher in the presence of 16 mM magnesium sulfate.

9. The Factor C protein according to claim 2, which exhibits a residual Factor C activity of 35% or higher in the presence of 2.5 mM calcium chloride.

10. A method for producing the Factor C protein of claim 2, the method comprising culturing a Chinese Hamster Ovary (CHO) DG44 cell or Human Embryonic Kidney (HEK) 293 cell recombinantly expressing said Factor C protein under conditions suitable for the expression of the Factor C protein to produce the Factor C protein.

11. An endotoxin assay kit comprising the Factor C protein according to claim 2 and one or more elements.

12. A method for measuring endotoxin in a test specimen, the method comprising
a step of mixing the Factor C protein according to claim 2, Factor B, Pro-clotting enzyme, and t-butoxycarbonyl-leucyl-glycyl-arginyl-pNA (Boc-Leu-Gly-Arg-pNA), and the test specimen, and
a step of measuring the release of pNA, thereby measuring endotoxin in the test specimen.

13. The method according to claim 12, wherein the test specimen comprises at least one of:
(A) an ion;
(B) a cation;
(C) a metal ion;
(D) an alkali metal ion or an alkaline earth metal ion; and
(E) one or more kinds of ions selected from the group consisting of sodium ion, potassium ion, calcium ion, and magnesium ion.

14. The method according to claim 13, wherein the test specimen comprises a cation and the final concentration of the cation after mixing the test specimen with the assay agent is 1 mM or higher.

15. The method according to claim 12, wherein the test specimen is an injection.

16. The Factor C protein according to claim 2, which exhibits a residual activity of 20% or higher in the presence of 21 mM sodium citrate.

17. The Factor C protein according to claim 2, which exhibits a residual activity of 25% or higher in the presence of 52 mM sodium hydrogen carbonate.

18. The Factor C protein according to claim 2, which exhibits a residual activity of 25% or higher in the presence of 214 mM sodium chloride.

19. The Factor C protein according to claim 1, wherein the Factor C protein contains ($\alpha$-2,3)-linked terminal sialic acid in a greater amount, as compared with a corresponding native horseshoe crab Factor C and a corresponding Factor C protein recombinantly expressed using Sf9 as a host cell.

20. The Factor C protein according to claim 2, wherein the Factor C protein contains ($\alpha$-2,3)-linked terminal sialic acid in a greater amount, as compared with a corresponding native horseshoe crab Factor C and a corresponding Factor C protein recombinantly expressed using Sf9 as a host cell.

21. A horseshoe crab Factor C protein having activity of Factor C,
wherein the horseshoe crab is *Limulus polyphemus*, and wherein the horseshoe crab Factor C protein is produced through being recombinantly expressed from a Human Embryonic Kidney (HEK) 293 cell, and
wherein the Factor C protein exhibits a residual activity of at least one selected from the group consisting of:
(1) 10% or higher in the presence of 21 mM sodium citrate; and
(2) 15% or higher in the presence of 16 mM magnesium sulfate.

\* \* \* \* \*

UNITED STATES PATENT AND TRADEMARK OFFICE
CERTIFICATE OF CORRECTION

PATENT NO. : 11,236,318 B2
APPLICATION NO. : 16/399386
DATED : February 1, 2022
INVENTOR(S) : Hikaru Mizumura, Toshio Oda and Shun-ichiro Kawabata It is certified that error appears in the above-identified patent and that said Letters Patent is hereby corrected as shown below:

On the Title Page

(56) References Cited

Page 2, Under OTHER PUBLICATIONS, left column, Line 29, delete "espress" and insert --express-- therefor.

Page 2, Under OTHER PUBLICATIONS, left column, Line 47, delete "[online],Retrived" and insert --[online], Retrieved-- therefor.

Page 2, Under OTHER PUBLICATIONS, right column, Line 23, delete "*Ganssia*" and insert --*Gaussia*-- therefor.

Page 2, Under OTHER PUBLICATIONS, right column, Line 43, delete "Tepidopteran" and insert --lepidopteran-- therefor.

Page 2, Under OTHER PUBLICATIONS, right column, Line 56, delete "Gycobiol" and insert --Glycobiol-- therefor.

In the Specification

Column 29, Line 51, delete "Celfectin" and insert --Cellfectin-- therefor.

Signed and Sealed this
Nineteenth Day of April, 2022

Katherine Kelly Vidal
*Director of the United States Patent and Trademark Office*